US008048621B2

(12) United States Patent
Haley et al.

(10) Patent No.: US 8,048,621 B2
(45) Date of Patent: Nov. 1, 2011

(54) BIOLOGICAL MARKERS PREDICTIVE OF ANTI-CANCER RESPONSE TO INSULIN-LIKE GROWTH FACTOR-1 RECEPTOR KINASE INHIBITORS

(75) Inventors: John D. Haley, Sea Cliff, NY (US); Elizabeth A. Buck, Huntington, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 193 days.

(21) Appl. No.: 12/286,291

(22) Filed: Sep. 29, 2008

(65) Prior Publication Data
US 2009/0092596 A1   Apr. 9, 2009

Related U.S. Application Data

(60) Provisional application No. 60/997,514, filed on Oct. 3, 2007.

(51) Int. Cl.
  *C12Q 1/00*   (2006.01)
  *G01N 33/574*   (2006.01)
(52) U.S. Cl. .......................................... 435/4; 435/7.23
(58) Field of Classification Search .................. None
See application file for complete search history.

(56) References Cited

U.S. PATENT DOCUMENTS

| | | | |
|---|---|---|---|
| 6,448,086 | B1 | 9/2002 | Khosravi |
| 6,617,121 | B1 | 9/2003 | Garcia |
| 7,081,340 | B2 | 7/2006 | Baker |
| 7,241,444 | B2 | 7/2007 | Goetsch |
| 2004/0018191 | A1 | 1/2004 | Wang |
| 2004/0106605 | A1 | 6/2004 | Carboni |
| 2004/0132097 | A1 | 7/2004 | Bacus |
| 2004/0209930 | A1 | 10/2004 | Carboni |
| 2005/0019785 | A1 | 1/2005 | Baker |
| 2005/0136063 | A1 | 6/2005 | Wang |
| 2005/0249730 | A1 | 11/2005 | Goetsch |
| 2005/0266496 | A1 | 12/2005 | Gilon |
| 2006/0018910 | A1 | 1/2006 | Gualberto |
| 2006/0046249 | A1 | 3/2006 | Huang |
| 2006/0140960 | A1 | 6/2006 | Wang |
| 2006/0211060 | A1 | 9/2006 | Haley |
| 2007/0059785 | A1 | 3/2007 | Bacus |
| 2007/0065858 | A1 | 3/2007 | Haley |
| 2007/0141621 | A1 | 6/2007 | Agus |
| 2007/0212738 | A1 | 9/2007 | Haley |
| 2007/0243194 | A1 | 10/2007 | Hariharan |
| 2007/0265185 | A1 | 11/2007 | Bouamrani |
| 2007/0270505 | A1 | 11/2007 | Bunn |
| 2008/0085519 | A1 | 4/2008 | Gabrin |
| 2008/0090233 | A1 | 4/2008 | Garcia |
| 2008/0312260 | A1 | 12/2008 | Haley |

FOREIGN PATENT DOCUMENTS

| | | |
|---|---|---|
| WO | 03078662 A1 | 9/2003 |
| WO | 2004046386 A1 | 6/2004 |
| WO | 2004063709 A2 | 7/2004 |
| WO | 2004065602 A1 | 8/2004 |
| WO | 2004071572 A2 | 8/2004 |
| WO | 2004111273 A2 | 12/2004 |
| WO | 2005017493 A2 | 2/2005 |
| WO | 2005037836 A2 | 4/2005 |
| WO | 2005052005 A1 | 6/2005 |
| WO | 2005061541 A1 | 7/2005 |
| WO | 2005067667 A2 | 7/2005 |
| WO | 2005070020 A2 | 8/2005 |
| WO | 2005094332 A2 | 10/2005 |
| WO | 2005097800 A1 | 10/2005 |
| WO | 2005099363 A2 | 10/2005 |
| WO | 2005107803 A2 | 11/2005 |
| WO | 2005117553 A2 | 12/2005 |
| WO | 2006099396 A2 | 9/2006 |
| WO | 2006101925 A2 | 9/2006 |
| WO | 2007028146 A | 3/2007 |
| WO | 2007035744 A | 3/2007 |
| WO | 2007075554 A2 | 7/2007 |
| WO | 2007141626 A1 | 12/2007 |
| WO | 2008104344 A1 | 9/2008 |
| WO | 2008115470 A2 | 9/2008 |
| WO | 2008144345 A2 | 11/2008 |

(Continued)

OTHER PUBLICATIONS

Glinsky et al, 2004, J Clin Invest, 113: 913-923.* Oesterreich, S et al, 1996 (Clin Cancer Res, 2: 1199-1206.*
Vandesompele J et al, 2003 (Oncogene, 22(3): 456-60).*
Tockman et al (Cancer Res., 1992, 52:2711s-2718s).*
Ritchie et al, 2001, Am J Hum Genet, 69: 138-147.*
Laasko, M. et al. (2006) Clinical Cancer Research: An official Journal of the American Association for Cancer Research 12: 14 part 1, 4185-4191.
Lan, M. et al. (2004) Carcinogenesis 25(12): 2385-2395.
Larrson, O. et al. (2005) British Journal of Cancer 92, 2097-2101.
Lee, J. M. et al. (2006) Journal of Cell Biology 172:7, 973-981.
Lemoine, N.R. et al. (1992) Br. J. Cancer 66:1116-11121.

(Continued)

*Primary Examiner* — Misook Yu
*Assistant Examiner* — Lei Yao
(74) *Attorney, Agent, or Firm* — Alexander A. Stewart; OSI Pharmaceuticals, LLC

(57) ABSTRACT

The present invention provides diagnostic and prognostic methods for predicting the effectiveness of treatment of a cancer patient with an IGF-1R kinase inhibitor. Methods are provided for predicting the sensitivity of tumor cell growth to inhibition by an IGF-1R kinase inhibitor, comprising assessing whether the tumor cell has undergone an epithelial to mesenchymal transition (EMT), by determining the expression level of epithelial and/or mesenchymal biomarkers, wherein tumor cells that have undergone an EMT are substantially less sensitive to inhibition by IGF-1R kinase inhibitors. Improved methods for treating cancer patients with IGF-1R kinase inhibitors that incorporate the above methodology are also provided. Additionally, methods are provided for the identification of new biomarkers that are predictive of responsiveness of tumors to IGF-1R kinase inhibitors. Furthermore, methods for the identification of agents that restore the sensitivity of tumor cells that have undergone EMT to inhibition by IGF-1R kinase inhibitors are also provided. pErk, HER3 and pHER are also demonstrated to be effective biomarkers for predicting sensitivity of tumor cells to IGF-1R kinase inhibitors.

2 Claims, 30 Drawing Sheets

FOREIGN PATENT DOCUMENTS

WO  2010120966 A1  10/2010

OTHER PUBLICATIONS

Letters to Journal (2005) J of Clin. Onco. 23, No. 4, Feb. 1, 2005; pp. 923-924.
Lippman, S.M. et al. (2005) Clin. Cancer Res. 11(17):6097-6099.
Locascio, A. et al. (2002) The Journal of Biological Chemistry 277(41): 38803-38809.
Lu, Z., et al., (2003) Cancer Cell. 4(6):499-515.
Markl, J. (1991) Journal of Cell Science 98: 261-264.
Matar, P. et al. (2004) Clin. Cancer Res. 10:6487-6501.
Matei, D. et al. (2006) Oncogene 25: 2060-2069.
Mitsiades, C.S., et al. (2006) Cancer Cell 5, 231-230.
Modern Pharmacology, 1990, Eds. Craig and Stitzel, Publishers, Little, Brown and Company, Chapter 60, pp. 776-778.
Moll, R. et al. (1982) Cell 31: 11-24.
Moody, S.E. (2005) Cancer Cell vol. 8, Sep. 2005, pp. 197-209.
Moon, H. et al (2001) Gynecologic Oncology 81:355-359.
Mulvihill, M.J. et al. (2009) Future Med. Chem. 1(6): 1153-1171.
Natalwala, A. et al. (2008) World J. Gastroenterol 14(24): 3792-3797.
Nolan, G.P. (2007) Nature Chemical Biology 3(4): 187-191.
Nunes, M. et al; (2004) Molecular Cancer Therapeutics, 3(1):21-27.
Ohira, T. et al. (2003) PNAS 100(18):10429-10434.
Osbourne, R. (2008) Nature Biotechnology 26(7):719-720.
Oshima, RG (2002) Cell Death and Differentiation 9: 486-492.
Pece, S. et al. (275) J Biol Chem 275 (52): 41227-41233.
Perez-Solar, R. et al. (2003) Lung Cancer 41 (Suppl. 2), p. S72, Abstract O247.
Peinado, H. et al, (2007) Nature Rev. Cancer, 7:415-428.
Pena, C. et al. (2005) Human Molecular Genetics 4(22).
Pollack, M.N., et al. (2004) Nature Reviews/Cancer 4, 505-518.
Pollack, M. (2009) Nature Reviews Cancer 8: 915-928.
Qian, X. et al (2004) EMBO 23:1739-1748.
Ramaekers, F.C.S. et al. (1987) Acta Histochemica Suppl. 34: 45-56.
Ramaekers, F.C.S. et al. (1983) Proc. Natl. Acad. Sci. USA 80: 2618-2622, May 1983, Cell Biology.
Ransohoff, D.F. (2003) Science 299, 1679-1680, downloaded from www.Sciencemag.org on Mar. 11, 2009.
Rasmussen, A., et al. (1998) Breast Cancer Research and Treatment 47(3): 219-233.
Richardson, F. et al. (2009) International Association for the Study of Lung Cancer, 13th World Conference on Lung Cancer, Jul. 31-Aug. 4, 2009, Moscone West, San Francisco, USA. "Comparison of E-cadherin IHC Status with Clinical Outcomes from Erlotinib in the Non Small Cell Lung Cancer (NSCLC) Clinical Trial NCIC CTG BR.21" e-Poster: PD7.2.5. Congress: WCLC 2009; 29 pages.
Riedemann, J. et al. (2006) Endocrine-Related Cancer 13, s33-s43.
Rosivatz, E. et al. (2002) American Journal of Pathology 161(5): 1881-1891.
Rukstalis, J.M. et al. (2006) Endocrinology 147(6): 2997-3006.
Ryan, P.D., et al. (2008) The Oncologist 13, 16-24 *downloaded from www.TheOncologist.com on May 29, 2008.
Sabatini, P. et al. (2009) Clin Cancer Res 15(9): 3058-3067.
Sakurai, H. et al.; (1997) Proc. Natl. Acad. Sci. USA, 94:6279-6284.
Samani, A.A. et al. (2007) Endocrine Reviews 28(1): 20-47.
Sarrio, D. et al. (2008) Cancer Research 68:4, 989-997.
Savagner, P. (2001) Bioessays 23:912-923.
Schaafsma, HE (May 1993) J. Pathol. 170(1): 77-86.
Schlessinger, K. et al. (2004) Nature Cell Biology 6(10):913-915.
Schussler, M.H. et al. (Mar. 1992) Am. J. Pathol. 140(3): 559-568.
Shrader, M. et al. (2007) Mol Cancer Ther 6(1): 277-285.
Shen, X. et al. (2004) Amer J Path 165 (4): 1315-1329.
Spaderna, S. et al. (2008) Cancer Res 68(2): 537-544.
"Sternberg, D., TAT Meeting, 8th International Symposium on Targeted Anticancer Therapies, Mar. 4-6, 2010. Bethesda, MD, USA, "The Development and Application of EMT Biomarkers in the Therapy of Solid Tumors"; 37 slides."
Struz, F. et al. (2002) Kidney Interantional 61:1714-1728.
Suggitt, M. et al. (2005) Clinical Cancer Res 11: 971-981.
Sun, T.T. (1984) Cancer Cell 1, The Transformed Phenotype vol. 1; 169-176, Levine, A. et al. eds.; Cold Spring Harbor Laboratory.
Suto, K. et al. (1999) J. Can.Res.Clin. Oncol. 125:83-88.
Takenaka, K. et al. (2005) Cancer Epidemiology Biomakers & Prevention 14(8):1972-1975.
Takkunen, M. (2006) Journal of Histochemistry & Cytochemistry 54(11): 1263-1275.
Tejeda, M.L. et al. (2006) Clinical Cancer Research 12(9): 2676-2688, May 1, 2006.
Thiery, J.P. (2002) Nat. Rev. Cancer 2:442-454.
Thomas, P.A. et al. (1999) Clinical Cancer Research 5: 2698-2703, Oct. 1999.
Thomson, S. et al. (2005) Cancer Res. 65(20):9455-9462.
Tockman, M.S. et al. (1992) Cancer Res 52:2711s-2718s.
Tsutsumi, S. et al. (2004) Clin Cancer Res 10: 7775-7784.
Tuma, R.S. et al. (2007) AACR-NCI-EORTC Molecular Targets Conference, Dec. 25, 2007.
Tuma, R.S. et al. (2005) J. Natl. Cancer Institute, 97(14):1028-1029.
Turley, E.A. et al. (2008) Nature Clinical Practice 5(5): 280-290.
Umemoto, M. et al. (2001) Brit. J. Can. 85:1032-1036.
Valdes, F. et al. (2002) Molecular Cancer Research, 1:68-78.
Valles, A. M. et al. (1990) Proc. Natl. Acad. Sci. USA 87:1124-1128, Feb. 1990, Cell Biology.
Van Roy, F. et al. (2008) Cell. Mol. Life Sci. 65: 3756-3788.
Warshamana-Greene, G. S., et al. (2003) Molecular Cancer Therapeutics, pp. 527-535.
Wellner, U. et al. (2010) Cancers 2: 1617-1628.
Wilding, J. et al. (1996) Cancer Res 56: 5285-5292.
Winter, J.M. et al. Clin Cancer Res 14(2): 412-418.
Witta S.E. et al. (2004) Proc. Amer. Assoc. Cancer Res. vol. 45 Abst. #3671, pp. 1-2.
Witta S.E. et al. (2005) J. Clin. Oncol. vol. 23, No. 165 (Jun. 1 Suppl.) Abst. #7083 (ASCO Proceedings).
Witta, S.E. et al. (2006) Cancer Res. 66(2):944-950.
Written Opinion of the International Search Authority in PCT/US2008/011299.
Xie, L. et al. (2004) Neoplasia 6(5): 603-610.
Yang, L. et al. (2006) Cell 127:139-155.
Yang, J. et al. (2008) Developmental Cell 14: 818-829.
Yano, S. et al. (2003) AntiCancer Res. 23(5A):3639-3650.
Yausch, R. L. et al. (2005) Clin. Cancer Res. 11:8686-8698.
Yin, T. et al. (2007) Journal of Surgical Research 141: 196-203.
Younes, M. (2005) J. Clinical Oncology 23(4): 923-924.
Zavadil, J. et al. (2005) Oncogene 24:5764-5774.
Aigner, K. et al. (2007) Oncogene pp. 1-10, Nature Publishing Group.
Alberts, B. et al. (1994) Molecular Biology of the Cell, 3rd edition, p. 465.
Amman, J. et al. (2005) Cancer Res. 65(1):226-235.
Andl, C. D., et al (2005) Cancer Biology and Therapy 4(1): 28-31.
Andl, C. D., et al (2003) J Biol Chem, 278 (No. 3):1824-1830.
Answers.com definition for "tumor", p. 1 (Apr. 17, 2009).
Armugam, T. et al. (2009) Cancer Res 2009; 69(14): 5820-5828.
ATTCC search Calu 6 (pp. 1-3; Mar. 10, 2010).
ATCC search H1703 (pp. 1-3; Mar. 10, 2010).
ATCC search H292 (pp. 1-3; Mar. 10, 2010).
ATCC search H358 (pp. 1-3; Mar. 10, 2010).
Auersberg, N. et al (1999) Proc Natl Acad Sci 96:6249-6254.
Babiychuk, E B et al. (2002) Bichimica ET Biophysica ACTA (BBA)—Proteins & Proteomics, Elsevier 1600, No. 1-2: 154-161.
Bailey, L.R. et al. (2003) Proc. Am. Assoc. Res. 44:1362. abst. LB-170.
Bankfalvi, Agnes, et al (2002) J Oral Pathol Med 31: 450-457.
Barrallo-Gimeno, A. et al. (2005) Development 132:3151-3161.
Baserga, R. (1999) Experimental Cell Research 253:1-6.
Bates, R.C. et al. (2003) Current Biology 13.1721-1727.
Batlle, E. et al. (2000) Nature Cell Biology 2:84-89.
Bergh, J. (1984) "Expression of intermediate filaments in established human lung cancer cell lines. An indicator of differentiation and derivation" Lab Invest 51(3): 307-316.
Berx, G. et al. (2009) Cold Spring Harb Perspect Biol 2009; 1: a003129 *published online Sep. 23, 2009.
Blanco, M.J. (2002) Oncogene 21: 3241-3246.
Bianco, R. et al. (2005) Endocrine-related cancer 12:S159-S171.
Biowww.net; "BRK gene" definition; pp. 1-3; Mar. 9, 2010.

Bolos, V. et al. (2003) Journal of Cell 116:499-511.
Brehmer, D. et al; (2005) Cancer Res. 65(2):379-382.
Broers, J.L.V. et al. (1988) Journal of Cell Science 83: 37-60.
Broers, J.L.V. et al. (1988) Journal of Cell Science 91: 91-108.
Buck, E. et al. (2007) Molecular Cancer Therapeutics 6(2): 532-541.
Buck, E. et al. (2006) Molecular Cancer Therapeutics 5(8): 2051-2059.
Buck, E. et al. (2008) Cancer Res 68(20): 8322-8332.
Burtrum, et al. (2003) American Association for Cancer Research 53(24): 8912-8921.
Camirand, A., et al. (2005) Breast Cancer Research 7:R570-R579.
Camp, E.R. et al; (2005) Clinical Cancer Research (1):397-405.
Cano, A. et al; (2000) Nature Cell Biology 2: 76-83.
Castillo, L. et al. (2004) Annals of Oncology 15:1007-1012.
Chaffer, C. L. et al. (2006) Cancer Research 66(23): 11271-11278.
Chandler, L.A. (1999) Int. J. Cancer 82: 451-458.
Christofori, G. (2006) Nature 441(7092): 444-450.
Chung, L.W.K. et al. (2005) The Journal of Urology 173:10-20.
Ciruna, B. et al. (2001) Developmental Cell 1: 37-49.
Clara, et al. (2007) European Journal of Cancer Supplement 5:4, 366-367.
Clark, D M et al. (1991) Histochemistry 96:5, 405-412.
Coltrera, M.D. (1995) Cancer Research 55: 2703-2708.
D'Souza, B et al (1994) Proc Natl Acad Sci 91:7202-7206.
Dai, Q. et al: (2005) Clinical Cancer Research 11:1572-1578.
Dancey, J. et al. (2003) Nature Rev. Drug Discovery 2:296-313.
Dandachi, N. et al. (2001) J. Pathology; 193:181-189.
De Bono, J.S. and Rowinsky, E.K. (2002) Trends in Mol. Medicine 8:S19-S26.
De Craene, B. et al. (2005) Cancer Res. 65(14): 6237-6244.
Derwent/ Delphion record for WO 2004065602.
Dumstrei, Karin et al (2002) Development 129: 3983-3994.
Ei-Deiry, W.S. et al. (2005) Cancer Res. 65(11):4475-4484.
Fedor-Chaiken, M et al (2003) Cell Communication and Adhesion 10:105-118.
Feng, Y., et al. (2008) Current Opinion in Drug Discovery & Development 11(2):178-185.
Frederick, B.A. et al. (2007) Mol Cancer Ther 6(6): 1683-1691.
Garber, K. (2009) JNCI 101(1): 6-8 *downloaded from http://jnci.oxfordjournals.org at OSI Pharmaceuticals, Inc. on Apr. 28, 2010.
Garcia-Echeverri, C., et al. (2004) Cancer Cell 5:231-239.
Giaccone, G. (2005) Annals of Oncology 16: 538-548.
Gotlieb, W.H., et al. (2000) Gynecologic Oncology 100, 389-396.
Grande, M. el al. (2202) J. Cell Science 115:4227-4236.
Greenbaum, D. et al. (2003) Genome Biology 4(9): 117.1-117.8.
Grille, S.J. et al. (2003) Cancer Res. 63: 2172-2178.
Gualberto, A. et al. (2009) Current Drug Targets 10: 923-936.
Gualberto, A. et al. (2009) Oncogene 28: 3009-3021.
Gura, T. (1997) Science 278: 1041-1042.
Hajra, K.M. (2002) Cancer Research 62: 1613-1618.
Haluska, P., et al. (2006) Cancer Research 66(1): 362-371.
Hazan, R. B. (1998) J Biol Chem 273 (15), 9078-9084.
Hirsch, F.R. (2005) Curr. Opin. Oncol. 17:118-122.
Hong, R. et al. (2008) The Korean Journal of Pathology 42: 351-357.
Hoorens, A. et al. (May 1998) J. Pathol. 185(1): 53-60.
Hopfner, M., et al. (2006) Endocrine-Related Cancer 13, 135-149.
Hotz,B. et al. (2007) Clin cancer Res 13(16):4769-4776.
Huang, F. et al. (2009) Cancer Res 69(1):161-170 with 9 page supplement.
Huber, M. et al. (2005) Current Opinion in Cell Biology 17:548-558.
Ibrahim, Y.H., et al. (2005) Clinical cancer Research 11, 944s-950s.
Imamichi, Y.(2007) Oncogene 26: 2381-2385.
International Search Report of the International Search Authority in PCT/US2008/011299.
International Preliminary Report on Patentability in PCT/US2008/011299.
Jain, A. et al. (2005) PNAS 102(33): 11858-11863.
Janda, E. et al; (2002) J. Cell Biology 156(2):299-313.
Janne, P.A. et al. (2009) Nature Reviews: Drug Discovery Sep. 2009, vol. 8:709-723.
Jawhari, Aida U. et al (1999) J Pathol 187: 155-157.
Jechlinger, M. et al. (2006) The Journal of Clinical Investigation, http: www.jci.org, vol. 16(6): 1561-1570.
Jechlinger, M. et al. (2003) Oncogene 22: 7155-7169.
Ji, Q. et al. (2007) Molecular Cancer Therapeutics 6(8):2158-2167.
Ji, Q. et al. (2007) Proceeding of the Annual Meeting of the American Association for Cancer Research vol. 48, Apr. 14, 2007, Abstract #2373.
Ji, Q., et al. (2007) Poster—Proceeding of the Annual Meeting of the American Association for Cancer Research vol. 48, Apr. 14, 2007—Abstract #2373.
Jiao, W. et al. (2002) British of Journal Cancer 86: 98-101.
Kamalati, T. et al. (2000) Oncogene 19:5471-5476.
Kamalati, T. et al. (1996) J. Biol. Chemistry 271(48):30956-30963.
Kang, Y. et al. (2004) Cell 118(3):277-279.
Kassouf, W. et al. (2005) Cancer Res. 65(2):10524-10535.
Kiermer,A.K. et al. (2001) Oncogene 20:6679-6688.
Kim, K.S. et al. (2005) Clinical Cancer Research, 11:2244-2251.
Kobayashi, S. et al; (2005) New England Journal of Medicine 352:786-792.
Kokubo, Y. et al. (2005) British J. Cancer 92:1711-1719.
Kris, M. et al. (2003) JAMA 290 (16):2149-2158.

* cited by examiner

Figure 7-A

| Name | Fraction | Acc | Protein Name | Calu6 vs H292 | H1703 vs H292 | Calu6 vs H358 | H1703 vs H358 |
|---|---|---|---|---|---|---|---|
| *Decreased in mesenchymal-like cells* | | | | | | | |
| 1433E | pY-S | P62258 | 14-3-3 epsilon | -0.38 | -1.38 | -0.38 | -1.38 |
| 1433G | Mem | P61981 | 14-3-3 gamma (KCIP-1) | -0.67 | 0.12 | -0.79 | 0.00 |
| 1433G | pY-B | P61981 | 14-3-3 gamma (KCIP-1) | -0.84 | -0.68 | -1.22 | -1.06 |
| 1433S | Cyto | P31947 | 14-3-3 sigma (Stratifin) | -1.58 | -2.06 | -1.83 | -2.37 |
| 1433S | Mem | P31947 | 14-3-3 sigma (Stratifin) | -1.13 | -1.55 | -1.33 | -1.77 |
| 1433S | pY-B | P31947 | 14-3-3 sigma (Stratifin) | -0.40 | -2.37 | -0.35 | -1.04 |
| 1433Z | Mem | P63104 | 14-3-3 zeta/delta | -0.76 | 0.15 | -1.26 | -0.42 |
| 1433Z | pY-B | P63104 | 14-3-3 zeta/delta | -0.52 | -0.53 | -0.48 | -0.47 |
| 1433Z | pY-E8P | P63104 | 14-3-3 zeta/delta | -1.25 | -0.62 | -0.89 | -0.35 |
| 1433Z | pY-S | P63104 | 14-3-3 zeta/delta | -0.67 | -0.90 | -1.05 | -1.18 |
| 2AAA | pY-B | P30153 | Serine/threonine phosphatase 2A | -0.52 | -0.91 | -0.54 | -0.82 |
| 2AAA | pY-S | P30153 | Serine/threonine phosphatase 2A | -0.63 | 0.28 | -1.22 | -0.52 |
| 4F2 | CS | P08195 | 4F2hc(CD98 antigen) | -1.60 | -1.12 | -1.72 | -1.21 |
| 4F2 | Mem | P08195 | 4F2hc(CD98 antigen) | -1.79 | -1.94 | -0.51 | -0.60 |
| ADT3 | Mem | P12236 | Adenine nucleotide translocator 2 | -0.44 | -0.57 | -0.78 | -0.91 |
| ANXA3 | Cyto | P12429 | Annexin A3 | -2.44 | -2.63 | -0.93 | -1.12 |
| ATPB | pY-B | P06576 | ATP synthase beta chain | -0.55 | -0.39 | -1.00 | -0.84 |
| BAIP2 | pY-B | Q9UQB8 | Insulin receptor substrate p53/p54 | -0.76 | -0.32 | -0.96 | -0.46 |
| BAIP2 | pY-S | Q9UQB8 | Insulin receptor substrate p53/p54 | -0.97 | -0.83 | -1.06 | -1.10 |
| BASI | Mem | P35613 | Basigin (CD147 antigen) | -0.56 | -0.92 | -0.26 | -0.59 |
| BASI | pY-B | P35613 | Basigin (CD147 antigen) | 0.10 | -0.46 | -0.32 | -0.79 |
| BCA1 | pY-B | P56945 | CRK-associated substrate (p130Cas) | -0.51 | -0.89 | -0.29 | -0.66 |
| BCA1 | pY-S | P56945 | CRK-associated substrate (p130Cas) | -0.47 | -1.05 | -0.41 | -0.99 |
| BCLX | Cyto | Q07817 | Bcl-X | -1.01 | -0.99 | -0.37 | -0.36 |
| BCLX | Mem | Q07817 | Bcl-X | -0.68 | -0.73 | -0.70 | -0.76 |
| CADH1 | CS | P12830 | E-cadherin | -0.14 | -0.50 | -0.92 | -0.64 |
| CADH1 | pY-B | P12830 | E-cadherin | -1.50 | -1.42 | -1.00 | -0.86 |
| CADH3 | pY-B | P22223 | P-cadherin | -2.52 | -1.28 | -1.98 | -0.74 |
| CALM | pY-B | P62158 | Calmodulin (CaM) | -0.55 | -0.63 | -1.39 | -1.47 |

Figure 7-B

Decreased in mesenchymal-like cells

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |
| CALM | pY-S | P62158 | Calmodulin (CaM) | -0.84 | -0.76 | -0.27 | -0.19 |
| CAN1 | Cyto | P07384 | Calpain-1 catalytic subunit | -0.38 | -0.62 | -0.34 | -0.61 |
| CAN2 | Cyto | P17655 | Calpain-2 catalytic subunit | -0.30 | -0.47 | -0.38 | -1.97 |
| CATD | Cyto | P07339 | Cathepsin D | -0.81 | -1.98 | -0.70 | -1.88 |
| CATD | Mem | P07339 | Cathepsin D | -0.17 | -0.74 | -0.60 | -1.29 |
| CATD | pY-B | P07339 | Cathepsin D | 0.07 | -0.64 | -1.06 | -1.39 |
| COF1 | Cyto | P23528 | Cofilin-1 | -0.30 | -0.40 | -0.56 | -0.70 |
| COF1 | Mem | P23528 | Cofilin-1 | -0.71 | -0.14 | -0.71 | -0.13 |
| CPNS1 | Cyto | P04632 | Calpain small subunit 1 | -0.86 | -0.76 | -0.87 | -0.77 |
| CTN1 | CS | P35221 | Catenin alpha-1 | -0.72 | -0.60 | -2.26 | -2.22 |
| CTN1 | Cyto | P35221 | Catenin alpha-1 | -0.85 | 0.06 | -0.89 | -0.10 |
| CTN1 | Mem | P35221 | Catenin alpha-1 | -1.22 | -1.21 | -1.40 | -1.52 |
| CTN1 | pY-B | P35221 | Catenin alpha-1 | -1.57 | -1.73 | -0.99 | -1.18 |
| CTN1 | pY-S | P35221 | Catenin alpha-1 | -0.82 | -0.59 | -0.89 | -0.72 |
| CTNB1 | CS | P35222 | Catenin beta-1 | -0.23 | -0.59 | -1.29 | -1.86 |
| CTNB1 | Mem | P35222 | Catenin beta-1 | -0.84 | -1.43 | -0.97 | -1.59 |
| CTNB1 | pY-B | P35222 | Catenin beta-1 | -0.99 | -0.86 | -0.52 | -0.44 |
| CTNB1 | pY-S | P35222 | Catenin beta-1 | -0.59 | -0.65 | -0.51 | -0.63 |
| CTND1 | CS | O60716 | Catenin delta-1 (p120 catenin) | -0.48 | -0.71 | -1.36 | -1.70 |
| CTND1 | Mem | O60716 | Catenin delta-1 (p120 catenin) | -0.66 | -1.20 | -0.73 | -1.32 |
| CTND1 | pY-B | O60716 | Catenin delta-1 (p120 catenin) | -1.44 | -1.68 | -0.79 | -1.05 |
| CTND1 | pY-E8P | O60716 | Catenin delta-1 (p120 catenin) | -1.22 | -0.75 | -0.67 | -0.36 |
| CTND1 | pY-S | O60716 | Catenin delta-1 (p120 catenin) | -0.95 | -1.19 | -1.27 | -1.50 |
| CYTB | Cyto | P04080 | Cystatin B | -0.04 | -0.35 | -1.02 | -1.35 |
| CYTB | Mem | P04080 | Cystatin B | -0.75 | -1.95 | -1.33 | -2.73 |
| DAZP1 | pY-B | Q96EP5 | DAZ-associated protein 1 | -0.31 | -0.64 | -0.93 | -1.02 |
| DAZP1 | pY-S | Q96EP5 | DAZ-associated protein 1 | -0.06 | -0.46 | -0.83 | -1.02 |
| DHCA | Cyto | P16152 | Carbonyl reductase [NADPH] | -1.47 | -0.42 | -1.20 | -0.15 |
| DIAP1 | Cyto | O60610 | Diaphanous-related formin 1 (DRF1) | -0.27 | -0.29 | -0.36 | -0.38 |

Figure 7-C

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| DIAP1 | Mem | O60610 | Diaphanous-related formin 1 (DRF1) | -0.48 | -0.57 | -0.19 | -0.40 |
| DSG2 | Mem | Q14126 | Desmoglein-2 | -0.75 | -0.90 | -0.66 | -0.81 |
| DSG2 | pY-B | Q14126 | Desmoglein-2 | -0.75 | -0.64 | -0.92 | -0.75 |
| EF1D | Cyto | P29692 | Elongation factor 1-delta | -0.65 | -0.12 | -0.66 | -0.15 |
| EF1D | Mem | P29692 | Elongation factor 1-delta | -0.78 | -0.21 | -0.94 | -0.31 |
| ERBB2 | pY-B | P04626 | p185erbB2 | -0.87 | -0.57 | -1.40 | -1.10 |
| ERBB2 | pY-E8P | P04626 | p185erbB2 | -1.29 | -0.13 | -0.47 | 0.74 |
| ERBB2 | pY-S | P04626 | p185erbB2 | -0.37 | -0.20 | -1.21 | -1.08 |
| EZRI | Cyto | P15311 | Ezrin (p81) | -0.99 | -0.79 | -0.68 | -0.60 |
| EZRI | Mem | P15311 | Ezrin (p81) | -0.80 | -0.27 | -1.17 | -0.68 |
| EZRI | pY-B | P15311 | Ezrin (p81) | -0.85 | -0.77 | -0.54 | -0.46 |
| EZRI | pY-S | P15311 | Ezrin (p81) | -0.25 | -0.74 | -0.23 | -0.71 |
| FAK1 | pY-S | Q05397 | Focal adhesion kinase 1 | -0.34 | -0.60 | -0.22 | -0.49 |
| FER | pY-B | P16591 | p94-FER (c-FER) | -0.60 | -0.47 | -0.97 | -0.84 |
| FER | pY-S | P16591 | p94-FER (c-FER) | -0.24 | 0.04 | -0.81 | -0.52 |
| FLNB | CS | O75369 | Filamin B | -0.97 | -0.09 | -0.46 | 0.42 |
| FLNB | Cyto | O75369 | Filamin B | -1.08 | -0.42 | -0.76 | -0.13 |
| FLNB | Mem | O75369 | Filamin B | -0.83 | -0.26 | -0.52 | 0.12 |
| GAB1 | pY-B | Q13480 | GRB2-associated binding protein 1 | -0.76 | -0.72 | -0.63 | -0.61 |
| GDIR | Cyto | P52565 | Rho-GDI alpha | -0.53 | -0.35 | -0.99 | -0.81 |
| GDIR | Mem | P52565 | Rho-GDI alpha | -0.56 | 0.05 | -0.82 | -0.18 |
| GRB2 | pY-B | P62993 | GRB2 | -1.08 | -0.78 | -0.89 | -0.57 |
| GRB2 | pY-E8P | P62993 | GRB2 | -0.84 | -0.55 | -0.62 | -0.57 |
| GRB2 | pY-S | P62993 | GRB2 | -0.89 | -0.70 | -1.50 | -1.57 |
| GRP78 | Cyto | P11021 | GRP 78 | -0.80 | -0.23 | -0.92 | -0.45 |
| GRP78 | Mem | P11021 | GRP 78 | -0.20 | -0.21 | -0.45 | -0.49 |
| GSTP1 | Cyto | P09211 | Glutathione S-transferase P | -0.87 | -0.97 | -0.68 | -0.82 |
| GSTP1 | Mem | P09211 | Glutathione S-transferase P | -1.20 | -0.71 | -1.01 | -0.52 |
| HCDH | Mem | Q16836 | 3-hydroxyacyl-CoA dehydrogenase | -0.30 | -0.61 | -0.19 | -0.50 |

Figure 7-D

| Name | Fraction | Acc | Protein Name | Protein Ratios (log2) Calu6 vs H292 | H1703 vs H292 | Calu6 vs H358 | H1703 vs H358 |
|---|---|---|---|---|---|---|---|
| *Decreased in mesenchymal-like cells* | | | | | | | |
| HS90A | Mem | P07900 | HSP 90-alpha | -0.37 | 0.17 | -0.79 | -0.25 |
| HS90A | pY-B | P07900 | HSP 90-alpha | -0.63 | -1.18 | -0.95 | -1.50 |
| HSP71 | Cyto | P08107 | HSP70.1 | -0.35 | -0.07 | -0.67 | -0.42 |
| HSP71 | Mem | P08107 | HSP70.1 | -0.58 | 0.00 | -0.82 | -0.24 |
| HSP71 | pY-E8P | P08107 | HSP70.1 | -0.54 | -0.54 | -0.49 | -0.51 |
| HSP71 | pY-S | P08107 | HSP70.1 | -0.51 | -0.31 | -0.74 | -0.54 |
| IF38 | Mem | Q99613 | eIF3 p110 | -0.61 | -0.31 | -0.62 | -0.35 |
| IF38 | pY-S | Q99613 | eIF3 p110 | -0.47 | -0.23 | -0.34 | -0.58 |
| IF4E | Mem | P06730 | eIF-4E | -0.88 | 0.08 | -1.35 | -0.35 |
| IF4E | pY-B | P06730 | eIF-4E | -0.73 | -0.46 | -0.79 | -0.60 |
| ILEU | Cyto | P30740 | Leukocyte elastase inhibitor | -1.15 | -0.84 | -1.42 | -1.10 |
| ILEU | Mem | P30740 | Leukocyte elastase inhibitor | -0.47 | -0.79 | -0.43 | -0.72 |
| IPO4 | Mem | Q8TEX9 | Importin-4 | -1.17 | -1.89 | -1.54 | -3.14 |
| ITA6 | CS | P23229 | Integrin alpha-6 | -0.46 | -0.04 | -1.20 | -1.01 |
| ITA6 | Mem | P23229 | Integrin alpha-6 | -0.14 | -0.76 | -0.07 | -0.69 |
| ITA6 | pY-B | P23229 | Integrin alpha-6 | 0.01 | -0.61 | -0.19 | -0.68 |
| ITB4 | CS | P16144 | Integrin beta-4 | -0.47 | -0.55 | -1.46 | -1.47 |
| ITB4 | Mem | P16144 | Integrin beta-4 | -0.95 | -1.42 | -0.95 | -1.33 |
| K1C17 | pY-E8P | Q04695 | Cytokeratin 17 | -3.48 | -4.28 | -2.51 | -3.31 |
| K1C17 | pY-S | Q04695 | Cytokeratin 17 | -2.23 | -1.93 | -0.30 | 0.00 |
| K1C18 | CS | P05783 | Cytokeratin 18 | 0.36 | -1.03 | -0.75 | -2.15 |
| K1C18 | Cyto | P05783 | Cytokeratin 18 | -0.79 | -1.69 | -1.18 | -2.01 |
| K1C18 | Mem | P05783 | Cytokeratin 18 | -0.84 | -2.17 | -0.68 | -1.89 |
| K1C18 | pY-B | P05783 | Cytokeratin 18 | -0.10 | -1.25 | 0.23 | -0.88 |
| K1C18 | pY-E8P | P05783 | Cytokeratin 18 | -0.86 | -1.38 | -1.00 | -1.55 |
| K1C18 | pY-S | P05783 | Cytokeratin 18 | -0.36 | -1.30 | -0.46 | -1.35 |
| K1C19 | CS | P08727 | Cytokeratin 19 | -0.04 | -0.24 | -2.33 | -2.72 |
| K1C19 | Mem | P08727 | Cytokeratin 19 | -0.39 | -0.82 | -1.95 | -2.44 |
| K1C19 | pY-B | P08727 | Cytokeratin 19 | -0.39 | -0.66 | -1.57 | -1.94 |

Figure 7-E

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| K1C19 | pY-S | P08727 | Cytokeratin 19 | -0.38 | -0.73 | -2.16 | -2.51 |
| K2C7 | CS | P08729 | Cytokeratin 7 | 0.70 | -0.33 | -1.01 | -1.92 |
| K2C7 | Cyto | P08729 | Cytokeratin 7 | -1.54 | -0.02 | -3.91 | -2.48 |
| K2C7 | Mem | P08729 | Cytokeratin 7 | -1.11 | -1.59 | -1.51 | -2.03 |
| K2C7 | pY-B | P08729 | Cytokeratin 7 | -0.65 | -1.47 | -0.75 | -1.54 |
| K2C7 | pY-E8P | P08729 | Cytokeratin 7 | -1.15 | -1.23 | -1.42 | -1.58 |
| K2C7 | pY-S | P08729 | Cytokeratin 7 | -1.04 | -1.44 | -1.74 | -2.13 |
| K2C8 | CS | P05787 | Cytokeratin 8 | 0.48 | -0.55 | -1.10 | -2.13 |
| K2C8 | Cyto | P05787 | Cytokeratin 8 | -0.59 | -0.91 | -0.97 | -1.44 |
| K2C8 | Mem | P05787 | Cytokeratin 8 | -0.86 | -1.27 | -0.92 | -1.33 |
| K2C8 | pY-B | P05787 | Cytokeratin 8 | -0.32 | -1.57 | -0.56 | -1.72 |
| K2C8 | pY-E8P | P05787 | Cytokeratin 8 | -0.56 | -0.76 | -1.45 | -1.69 |
| K2C8 | pY-S | P05787 | Cytokeratin 8 | -0.33 | -1.24 | -1.25 | -2.08 |
| KC1A | Mem | P48729 | Casein kinase I, alpha | -0.65 | -0.32 | -0.91 | -0.95 |
| KC1A | pY-B | P48729 | Casein kinase I, alpha | -1.96 | -1.54 | -1.80 | -1.39 |
| KC1A | pY-S | P48729 | Casein kinase I, alpha | -0.93 | -0.92 | -0.81 | -0.80 |
| KPCD | pY-B | Q05655 | Protein kinase C, delta | -0.56 | -0.83 | -0.97 | -1.26 |
| KPYM | CS | P14618 | Pyruvate kinase, isozymes M1/M2 | -1.01 | -0.47 | -0.79 | -0.08 |
| KPYM | Cyto | P14618 | Pyruvate kinase, isozymes M1/M2 | 0.25 | -0.40 | -0.18 | -1.02 |
| KPYM | Mem | P14618 | Pyruvate kinase, isozymes M1/M2 | -0.67 | -0.13 | -1.03 | -0.59 |
| LAP2 | pY-B | Q96RT1 | Erbin | -1.04 | -0.68 | -0.46 | -0.03 |
| LASP1 | Cyto | Q14847 | LIM and SH3 domain protein 1 (LASP-1) | -0.41 | -0.18 | -0.28 | -0.36 |
| LASP1 | pY-B | Q14847 | LIM and SH3 domain protein 1 (LASP-1) | -0.54 | -0.34 | -0.47 | -0.25 |
| LAT1 | CS | Q01650 | 4F2lc (CD98 light chain) | -1.50 | -1.59 | -1.46 | -1.47 |
| LAT1 | Mem | Q01650 | 4F2lc (CD98 light chain) | -2.03 | -2.18 | -0.38 | -0.52 |
| LAT1 | pY-B | Q01650 | 4F2lc (CD98 light chain) | -0.74 | -0.65 | -0.91 | -0.83 |
| LDHA | Cyto | P00338 | L-lactate dehydrogenase A chain | -0.57 | -0.91 | -0.24 | -0.75 |
| LDHA | Mem | P00338 | L-lactate dehydrogenase A chain | -1.43 | -0.92 | -0.75 | -0.20 |
| LEG3 | CS | P17931 | Galectin-3 | 0.66 | -0.30 | -2.11 | -3.07 |

Figure 7-F

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| LEG3 | Cyto | P17931 | Galectin-3 | -0.26 | -1.44 | -1.49 | -2.63 |
| LEG3 | Mem | P17931 | Galectin-3 | -0.36 | -0.78 | -1.13 | -1.50 |
| LEG3 | pY-S | P17931 | Galectin-3 | -0.23 | -0.62 | -2.06 | -2.45 |
| LG3BP | Mem | Q08380 | Galectin-3 binding protein | 0.14 | -0.69 | -1.46 | -2.23 |
| LG3BP | pY-B | Q08380 | Galectin-3 binding protein | 0.39 | -0.70 | -0.60 | -1.58 |
| LG3BP | pY-E8P | Q08380 | Galectin-3 binding protein | 1.16 | -0.33 | -1.31 | -3.19 |
| LG3BP | pY-S | Q08380 | Galectin-3 binding protein | 0.61 | -0.34 | -0.48 | -1.46 |
| LIN7C | pY-B | Q9NUP9 | LIN-7 homolog C | -0.97 | -1.21 | -0.94 | -1.17 |
| LIN7C | pY-S | Q9NUP9 | LIN-7 homolog C | -0.15 | -0.31 | -0.40 | -0.49 |
| MARE1 | Cyto | Q15691 | MAP (APC-binding protein EB1) | -0.78 | -0.50 | -0.43 | -0.14 |
| MARE1 | Mem | Q15691 | MAP (APC-binding protein EB1) | -0.55 | -0.17 | -0.45 | -0.04 |
| MASP | Cyto | P36952 | Maspin precursor (Protease inhibitor 5) | -2.02 | -1.70 | -1.78 | -1.84 |
| MET | pY-B | P08581 | Met tyrosine kinase (HGF receptor) | -1.34 | -1.39 | -0.46 | -0.50 |
| MET | pY-S | P08581 | Met tyrosine kinase (HGF receptor) | -0.57 | -0.66 | -0.42 | -0.62 |
| MLL2 | Cyto | O14686 | Mixed-lineage leukemia protein 2 | -0.11 | -0.42 | -0.14 | -0.44 |
| MLL2 | Mem | O14686 | Mixed-lineage leukemia protein 2 | -0.16 | -0.29 | -1.06 | -1.48 |
| MLL2 | pY-B | O14686 | Mixed-lineage leukemia protein 2 | -0.14 | -0.37 | -0.05 | -0.43 |
| MOT4 | Mem | O15427 | Monocarboxylate transporter 4 | -0.53 | -1.42 | -0.65 | -1.52 |
| MOT4 | pY-B | O15427 | Monocarboxylate transporter 4 | -0.24 | -0.90 | -0.63 | -1.35 |
| MOT4 | pY-S | O15427 | Monocarboxylate transporter 4 | -0.28 | -0.47 | -0.95 | -1.20 |
| MYCBP | pY-B | Q99417 | C-Myc binding protein (AMY-1) | -0.40 | -0.37 | -0.40 | -0.45 |
| MYCBP | pY-S | Q99417 | C-Myc binding protein (AMY-1) | -0.27 | 0.32 | -0.73 | -0.30 |
| MYH9 | Mem | P35579 | Myosin-9 | -0.68 | -0.05 | -0.85 | -0.23 |
| MYH9 | pY-S | P35579 | Myosin-9 | -0.94 | -0.57 | -1.23 | -0.76 |
| MYL6 | Mem | P60660 | Myosin light polypeptide 6 | -0.95 | -0.06 | -0.96 | -0.05 |
| MYL6 | pY-B | P60660 | Myosin light polypeptide 6 | -0.69 | -0.64 | -0.21 | -0.61 |
| MYL6 | pY-S | P60660 | Myosin light polypeptide 6 | -1.22 | 0.15 | -1.03 | -0.15 |
| NAMPT | Cyto | P43490 | Nicotinamide phosphoribosyltransferase | -1.30 | -0.13 | -2.80 | -1.65 |
| NAMPT | Mem | P43490 | Nicotinamide phosphoribosyltransferase | -0.82 | 0.19 | -1.23 | -0.20 |

Figure 7-G

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| NAMPT | pY-S | P43490 | Nicotinamide phosphoribosyltransferase | -0.43 | -0.69 | -0.53 | -0.85 |
| NIBL | Cyto | Q96TA1 | Niban-like protein (Meg-3) | -0.26 | -0.54 | -1.13 | -1.42 |
| NIBL | Mem | Q96TA1 | Niban-like protein (Meg-3) | -0.63 | -0.34 | -1.14 | -0.82 |
| OAT | Mem | P04181 | Ornithine aminotransferase | -1.12 | -1.39 | -0.63 | -0.94 |
| OCLN | pY-B | Q16625 | Occludin | -0.85 | -0.32 | -0.93 | -0.42 |
| OTUB1 | Cyto | Q96FW1 | Ubiquitin thiolesterase | -0.19 | -0.42 | -0.39 | -0.74 |
| PA1B2 | Cyto | P68402 | PAF acetylhydrolase IB beta subunit | -0.45 | -0.55 | -0.18 | -0.30 |
| PA1B2 | Mem | P68402 | PAF acetylhydrolase IB beta subunit | -0.52 | -0.52 | -0.52 | -0.49 |
| PARD3 | pY-B | Q8TEW0 | Partitioning-defective 3 (PAR-3) | -0.22 | -0.12 | -0.29 | -0.20 |
| PDC6I | pY-B | Q8WUM4 | Programmed cell death 6-interacting protein | -1.86 | -0.52 | -1.53 | -0.17 |
| PDCD6 | pY-B | O75340 | Programmed cell death protein 6 | -0.74 | -0.32 | -0.93 | -0.62 |
| PDCD6 | pY-E8P | O75340 | Programmed cell death protein 6 | -0.11 | -0.55 | -1.08 | -1.57 |
| PDCD6 | pY-S | O75340 | Programmed cell death protein 6 | -0.59 | -0.41 | -0.65 | -0.59 |
| PDIA1 | CS | P07237 | Protein disulfide-isomerase | -1.47 | 0.25 | -0.79 | 0.99 |
| PDIA1 | Cyto | P07237 | Protein disulfide-isomerase | -0.61 | 0.34 | -1.79 | -0.91 |
| PDIA1 | Mem | P07237 | Protein disulfide-isomerase | -0.44 | -0.57 | -1.27 | -1.40 |
| PKP2 | pY-B | Q99959 | Plakophilin-2 | -0.69 | -0.37 | -0.56 | -0.29 |
| PKP3 | pY-B | Q9Y446 | Plakophilin-3 | -0.87 | -0.99 | -0.31 | -0.47 |
| PKP3 | pY-S | Q9Y446 | Plakophilin-3 | -0.60 | -0.75 | -0.49 | -0.69 |
| PP14B | Cyto | Q96C90 | Protein phosphatase 1 | -0.49 | -1.49 | -0.08 | -1.15 |
| PP14B | Mem | Q96C90 | Protein phosphatase 1 | -1.68 | -1.26 | -1.28 | -0.84 |
| PRDX5 | Cyto | P30044 | Peroxiredoxin 5 | -1.05 | -1.13 | -0.36 | -0.51 |
| PSME1 | Cyto | Q06323 | Proteasome activator complex subunit 1 | -0.22 | -0.44 | -0.71 | -0.95 |
| PSME1 | pY-B | Q06323 | Proteasome activator complex subunit 1 | -0.48 | -0.58 | -1.01 | -1.05 |
| PTMA | Cyto | P06454 | Prothymosin alpha | -0.63 | -1.18 | 0.26 | -0.33 |
| PTMA | Mem | P06454 | Prothymosin alpha | -1.24 | -1.06 | -0.98 | -0.77 |
| RAI3 | Mem | Q8NFJ5 | Retinoic acid-induced protein 3 | -1.46 | -4.68 | 0.26 | -0.86 |
| RAI3 | pY-B | Q8NFJ5 | Retinoic acid-induced protein 3 | -1.51 | -1.54 | -0.81 | -0.74 |
| RAI3 | pY-S | Q8NFJ5 | Retinoic acid-induced protein 3 | -1.58 | -1.66 | -1.21 | -1.32 |

Figure 7-H

| Name | Fraction | Acc | Protein Name | Protein Ratios (log2) | | |
|------|----------|-----|--------------|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|------|----------|-----|--------------|---|---|---|---|
| REV1 | pY-B | Q9UBZ9 | DNA repair protein REV1 | -0.39 | -0.74 | -0.47 | -0.87 |
| REV1 | pY-S | Q9UBZ9 | DNA repair protein REV1 | -0.29 | 0.29 | -0.95 | -0.49 |
| RINI | Cyto | P13489 | Ribonuclease inhibitor | -0.81 | -0.79 | -0.54 | -0.58 |
| RINI | Mem | P13489 | Ribonuclease inhibitor | -0.95 | 0.14 | -0.93 | 0.19 |
| RUVB1 | Mem | Q9Y265 | RuvB-like 1 | -0.34 | -0.23 | -0.50 | -0.35 |
| RUVB1 | pY-B | Q9Y265 | RuvB-like 1 | -0.36 | -0.59 | -0.25 | -0.46 |
| S100P | Cyto | P25815 | S-100P | -0.39 | -0.73 | -2.41 | -2.61 |
| S100P | Mem | P25815 | S-100P | -0.70 | -0.50 | -2.72 | -2.56 |
| S100P | pY-B | P25815 | S-100P | -0.32 | -0.72 | -1.16 | -1.54 |
| S10A2 | Cyto | P29034 | S-100L | -2.08 | -2.64 | -0.33 | -0.64 |
| S10A2 | Mem | P29034 | S-100L | -1.49 | -1.55 | -0.33 | -0.42 |
| S10A2 | pY-B | P29034 | S-100L | -1.38 | -1.47 | -0.94 | -0.81 |
| S10A6 | Cyto | P06703 | Calcyclin | -0.03 | -0.82 | -1.42 | -2.13 |
| S10A6 | Mem | P06703 | Calcyclin | -0.42 | -0.51 | -0.94 | -1.14 |
| S10A6 | pY-B | P06703 | Calcyclin | -0.28 | -0.44 | -0.92 | -1.08 |
| S10AB | Cyto | P31949 | S100C | -0.36 | -1.93 | -0.75 | -2.32 |
| S10AB | Mem | P31949 | S100C | -0.46 | -1.35 | -0.72 | -1.70 |
| S10AB | pY-B | P31949 | S100C | -0.73 | 0.23 | -0.78 | 0.20 |
| SC23A | Cyto | Q15436 | Sec23A | -0.33 | -0.80 | -0.20 | -0.65 |
| SC23A | pY-S | Q15436 | Sec23A | -0.25 | -0.07 | -0.77 | -0.45 |
| SC23B | pY-B | Q15437 | Sec23B | -1.07 | -0.60 | -1.34 | -0.99 |
| SCRB2 | Mem | Q14108 | Lysosome membrane protein II (LIMP II) | -0.28 | -0.46 | -0.51 | -0.67 |
| SRC | pY-B | P12931 | p60-Src | -2.62 | | -1.87 | -1.81 |
| SRC | pY-E8P | P12931 | p60-Src | | -1.43 | -0.92 | 0.19 |
| SRC | pY-S | P12931 | p60-Src | -0.62 | -0.49 | -0.92 | -0.85 |
| SRC8 | pY-S | Q14247 | Amplaxin (EMS1) | -0.54 | -0.61 | -0.44 | -0.56 |
| STML2 | Mem | Q9UJZ1 | SLP-2 | -0.20 | -0.22 | -0.28 | -0.30 |
| SYUG | Cyto | O76070 | Gamma-synuclein | -0.66 | -0.61 | -0.75 | -0.72 |
| SYUG | Mem | O76070 | Gamma-synuclein | -0.62 | 0.06 | -0.75 | -0.04 |

Figure 7-I

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| TACD1 | Mem | P16422 | Tumor calcium signal transducer 1 | -0.57 | -0.81 | -1.12 | -1.30 |
| TACD2 | CS | P09758 | Tumor calcium signal transducer 2 | -1.30 | -0.88 | -1.32 | -0.82 |
| TACD2 | Mem | P09758 | Tumor calcium signal transducer 2 | -2.04 | -2.19 | -0.75 | -0.84 |
| TAGL2 | Cyto | P37802 | Transgelin-2 | -0.59 | -0.82 | -1.02 | -1.35 |
| TAGL2 | Mem | P37802 | Transgelin-2 | -0.71 | -0.46 | -1.14 | -0.98 |
| TAGL2 | pY-B | P37802 | Transgelin-2 | | | -1.42 | -1.53 |
| TALDO | Cyto | P37837 | Transaldolase | -0.50 | -1.06 | 0.18 | -0.40 |
| TALDO | Mem | P37837 | Transaldolase | -0.41 | -0.46 | -0.42 | -0.44 |
| TBBX | Cyto | P68371 | Tubulin beta-2 chain | -0.68 | 0.19 | -0.62 | 0.23 |
| TBBX | Mem | P68371 | Tubulin beta-2 chain | -0.41 | -0.69 | -0.27 | -0.53 |
| TBBX | pY-B | P68371 | Tubulin beta-2 chain | -0.17 | -0.66 | -0.45 | -0.72 |
| TCTP | Cyto | P13693 | Translationally controlled (TCTP) | -0.91 | -0.01 | -1.02 | -0.18 |
| TCTP | Mem | P13693 | Translationally controlled (TCTP) | -0.30 | -2.37 | -0.52 | -0.99 |
| TGM2 | Cyto | P21980 | Tissue transglutaminase | -2.81 | -2.56 | -0.76 | -0.44 |
| TGM2 | Mem | P21980 | Tissue transglutaminase | -1.42 | -1.15 | -0.41 | -0.09 |
| TGM2 | pY-B | P21980 | Tissue transglutaminase | -1.12 | -1.16 | -0.28 | -0.42 |
| TMP21 | Mem | P49755 | Transmembrane protein Tmp21 | -0.53 | -0.37 | -0.54 | -0.51 |
| UBE2N | Cyto | P61088 | Ubiquitin-conjugating enzyme E2 N | 0.36 | -0.29 | -0.31 | -0.98 |
| UBE2N | Mem | P61088 | Ubiquitin-conjugating enzyme E2 N | -0.38 | -0.39 | -0.45 | -0.43 |
| UGGG1 | Mem | Q9NYU2 | UDP-glucosyltransferase 1 | -0.29 | -0.44 | -0.82 | -0.96 |
| UGGG1 | pY-B | Q9NYU2 | UDP-glucosyltransferase 1 | -1.10 | -0.25 | -0.91 | -0.06 |
| YES | pY-B | P07947 | p61-Yes | -0.32 | -0.44 | -0.87 | -0.99 |
| YES | pY-S | P07947 | p61-Yes | -0.14 | -0.44 | -0.89 | -1.24 |
| ZO1 | pY-B | Q07157 | Tight junction protein ZO-1 | -0.45 | -0.63 | -0.54 | -0.71 |
| ZO1 | pY-S | Q07157 | Tight junction protein ZO-1 | -0.63 | -0.60 | -0.36 | -0.38 |

*Increased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| 1A01 | CS | P30443 | MHC class I antigen A*1 | 0.35 | 1.19 | 0.61 | 1.55 |

Figure 7-J

| Name | Fraction | Acc | Protein Name | Calu6 vs H292 | H1703 vs H292 | Calu6 vs H358 | H1703 vs H358 |
|---|---|---|---|---|---|---|---|
| *Increased in mesenchymal-like cells* | | | | | | | |
| 1A01 | Mem | P30443 | MHC class I antigen A*1 | 0.42 | 1.22 | 0.45 | 1.08 |
| ACOD | Mem | O00767 | Acyl-CoA desaturase | 0.9 | 0.84 | 2.12 | 2.4 |
| AN32E | Cyto | Q9BTT0 | LANP- like protein (LANP-L) | 0.68 | 1.09 | 0.47 | 0.84 |
| ANXA6 | Cyto | P08133 | Annexin A6 | 3.11 | 2.27 | 2.65 | 1.78 |
| ANXA6 | Mem | P08133 | Annexin A6 | 4.02 | 2.95 | 2.48 | 1.54 |
| ATPG | Mem | P36542 | ATP synthase gamma chain | 0.69 | 0.1 | 1.01 | 0.42 |
| BAG2 | Mem | O95816 | BAG-family molecular chaperone regulator-2 | 0.58 | 0.41 | 0.62 | 0.46 |
| BAG2 | pY-B | O95816 | BAG-family molecular chaperone regulator-2 | 0.63 | 0.24 | 0.57 | 0.49 |
| BPAEA | pY-B | O94833 | Bullous pemphigoid antigen | 0.79 | 0.81 | 1.36 | 1.46 |
| BPAEA | pY-S | O94833 | Bullous pemphigoid antigen | 0.29 | 0.47 | 0.8 | 0.89 |
| CA077 | pY-B | Q9Y3Y2 | Protein C1orf77 | 0.92 | 0.58 | 1.37 | 1.02 |
| CA077 | pY-S | Q9Y3Y2 | Protein C1orf77 | 0.79 | 0.68 | 1.2 | 1.03 |
| CDC2 | Cyto | P06493 | CDK1 (cdc2) | 0.84 | 0.33 | 1.03 | 0.5 |
| CDC2 | pY-B | P06493 | CDK1 (cdc2) | 0.6 | 0.38 | 1.28 | 1.06 |
| CDC2 | pY-S | P06493 | CDK1 (cdc2) | 0.85 | 0.06 | 1.47 | 0.67 |
| CLH1 | pY-B | Q00610 | Clathrin heavy chain 1 | 0.36 | 0.79 | 1.09 | 1.52 |
| CLH1 | pY-S | Q00610 | Clathrin heavy chain 1 | 0.1 | 0.49 | 0.86 | 1.25 |
| CND1 | Cyto | Q15021 | Condensin complex subunit 1 | 0.28 | 0.84 | 0.27 | 0.98 |
| CND1 | Mem | Q15021 | Condensin complex subunit 1 | 0.45 | 0.4 | 0.32 | 0.31 |
| D3D2 | Mem | P42126 | 3,2-trans-enoyl-CoA isomerase | 0.47 | 0.32 | 0.55 | 0.39 |
| DHX9 | Cyto | Q08211 | DEAH- box protein 9 | 0.96 | 0.7 | 0.88 | 0.62 |
| DHX9 | Mem | Q08211 | DEAH- box protein 9 | 0.14 | 0.35 | 0.27 | 0.48 |
| ERH | pY-B | P84090 | Enhancer of rudimentary homolog | 0.74 | 0.86 | 1.01 | 1.06 |
| FBRL | pY-B | P22087 | Fibrillarin | 1.29 | 0.99 | 1.19 | 0.89 |
| FBRL | pY-S | P22087 | Fibrillarin | 0.86 | 0.68 | 1.34 | 1.16 |
| G3P1 | CS | P00354 | GAPDH muscle | -0.97 | 0.33 | -0.82 | 0.6 |
| G3P1 | Mem | P00354 | GAPDH muscle | -0.53 | 0.5 | 0.34 | 1.32 |
| G3P1 | pY-S | P00354 | GAPDH muscle | 0.28 | 0.55 | 0.83 | 1.08 |
| G3P2 | CS | P04406 | GAPDH liver | -0.47 | 0.47 | -0.59 | 0.44 |

Figure 7-K

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Increased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| G3P2 | Cyto | P04406 | GAPDH liver | 0.09 | 0.32 | 0.11 | 0.33 |
| G3P2 | Mem | P04406 | GAPDH liver | -0.44 | 0.29 | -0.19 | 0.57 |
| G3P2 | pY-E8P | P04406 | GAPDH liver | 0.66 | 1.42 | 0.15 | 1.02 |
| G3P2 | pY-S | P04406 | GAPDH liver | 0.79 | 1.1 | 1.23 | 1.4 |
| GPSN2 | Mem | Q9NZ01 | Synaptic glycoprotein SC2 | 0.55 | 0.36 | 1.32 | 1.14 |
| H10 | pY-B | P07305 | Histone H1.0 | 2.38 | 0.93 | 2.01 | 0.56 |
| H10 | pY-S | P07305 | Histone H1.0 | 1.17 | 0.28 | 0.49 | -0.39 |
| H12 | pY-B | P16403 | Histone H1.2 | 2.41 | 1.94 | 2.86 | 2.41 |
| H13 | pY-B | P16402 | Histone H1.3 | 1.15 | 1.69 | 2.06 | 2.54 |
| H13 | pY-S | P16402 | Histone H1.3 | 0.66 | 1.6 | 1.57 | 2.35 |
| H14 | pY-B | P10412 | Histone H1.4 | 2.17 | 1.81 | 2.75 | 2.4 |
| H14 | pY-E8P | P10412 | Histone H1.4 | 1.16 | 1.03 | 1.86 | 1.79 |
| H14 | pY-S | P10412 | Histone H1.4 | 1.94 | 1.63 | 1.73 | 1.36 |
| H15 | pY-B | P16401 | Histone H1.5 | 2.08 | 1.92 | 2.59 | 2.46 |
| H1X | pY-B | Q92522 | Histone H1x | 0.69 | 0.35 | 0.78 | 0.31 |
| H2AFX | pY-B | P16104 | Histone H2AFX | 1.23 | 0.87 | 1.61 | 1.27 |
| H2AFX | pY-E8P | P16104 | Histone H2AFX | 2.49 | 0.35 | 2.2 | 0.33 |
| H2AFX | pY-S | P16104 | Histone H2AFX | 1.54 | 0.81 | 0.83 | 0.1 |
| H2AO | pY-B | P20670 | Histone H2A.o | 3.17 | 2.66 | 2.71 | 2.24 |
| H2AO | pY-S | P20670 | Histone H2A.o. | 2.84 | 2.5 | 2.3 | 1.93 |
| H2AQ | pY-B | Q16777 | Histone H2A.q | 2.65 | 2.27 | 2.59 | 2.12 |
| H2AQ | pY-S | Q16777 | Histone H2A.q | 2.45 | 3.14 | 1.4 | 1.25 |
| H2AZ | pY-B | P17317 | Histone H2A.z | 0.78 | 0.61 | 0.87 | 0.69 |
| H2BJ | pY-B | Q93079 | Histone H2B.j | 1.41 | 1.67 | 1.65 | 1.91 |
| H2BJ | pY-S | Q93079 | Histone H2B.j | 1.43 | 1.24 | 1.24 | 0.99 |
| H2BR | pY-B | P06899 | Histone H2B.r | 1.85 | 1.82 | 1.95 | 1.92 |
| H4 | pY-B | P62805 | Histone H4 | 1.85 | 1.92 | 2.01 | 2.07 |
| HG173 | pY-B | O00479 | HMG-17-like 3 | 1 | 1.62 | 1.2 | 1.79 |
| HMG14 | pY-B | P05114 | HMG-14 | 1.45 | 1.5 | 1.76 | 1.8 |

Figure 7-L

Increased in mesenchymal-like cells

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |
| HMG17 | pY-B | P05204 | HMG-17 | 2.75 | 2.4 | 2.76 | 2.44 |
| HMG17 | pY-S | P05204 | HMG-17 | 1.9 | 1.55 | 1.12 | 0.74 |
| HMGIC | pY-B | P52926 | HMGI-C | 2.68 | 0.78 | 2.71 | 0.89 |
| HMGIC | pY-S | P52926 | HMGI-C | 1.82 | 0.32 | 1.7 | 0.17 |
| HMGIY | pY-B | P17096 | HMG-I/HMG-Y | 1.62 | 1.68 | 1.21 | 1.3 |
| HMGN3 | pY-B | Q15651 | Thyroid receptor interacting protein 7 (TRIP7) | 0.78 | 1.09 | 1.25 | 1.08 |
| HNRH3 | pY-B | P31942 | hnRNP H3 | 0.44 | 0.27 | 0.84 | 0.66 |
| HNRH3 | pY-S | P31942 | hnRNP H3 | 0.33 | 0.5 | 0.7 | 0.86 |
| HNRPC | Mem | P07910 | hnRNP C1/C2 | 0.57 | 0.2 | 1.1 | 0.75 |
| HNRPC | pY-B | P07910 | hnRNP C1/C2 | 1.16 | 0.8 | 1.68 | 1.35 |
| HNRPC | pY-S | P07910 | hnRNP C1/C2 | 0.6 | 0.22 | 0.78 | 0.4 |
| HNRPF | Cyto | P52597 | hnRNP F | 0.47 | 0.42 | 0.82 | 0.76 |
| HNRPF | Mem | P52597 | hnRNP F | 0.01 | 0.45 | 0.31 | 0.75 |
| HNRPF | pY-S | P52597 | hnRNP F | 0.47 | 0.01 | 0.79 | 0.34 |
| HNRPG | pY-B | P38159 | hnRNP G | 1.39 | 1.3 | 1.5 | 1.47 |
| HNRPG | pY-S | P38159 | hnRNP G | 1.03 | 0.99 | 1.22 | 1.12 |
| IF5A | Cyto | P63241 | eIF-5A | 0.47 | 0.69 | 0.82 | 0.98 |
| IF5A | Mem | P63241 | eIF-5A | 0.28 | 0.32 | 0.43 | 0.48 |
| ILF2 | Cyto | Q12905 | NFAT 45 kDa | 0.4 | 0.14 | 1.03 | 0.76 |
| ILF2 | Mem | Q12905 | NFAT 45 kDa | 0.35 | 0.47 | 0.52 | 0.67 |
| ILF2 | pY-B | Q12905 | NFAT 45 kDa | 0.51 | 0.14 | 1.04 | 0.66 |
| IMB3 | Cyto | O00410 | Importin beta-3 | 1.21 | 0.32 | 1.08 | 0.19 |
| IMB3 | Mem | O00410 | Importin beta-3 | 0.55 | 0.33 | 0.4 | 0.18 |
| KAP0 | Cyto | P10644 | cAMP-dependent PK1a | 0.12 | 0.25 | 0.46 | 0.5 |
| KAP0 | Mem | P10644 | cAMP-dependent PK1a | 0.99 | 0.8 | 0.86 | 0.65 |
| LAM1 | Mem | P20700 | Lamin B1 | 1.5 | 1.19 | 1.77 | 1.2 |
| LAM1 | pY-B | P20700 | Lamin B1 | 0.9 | 0.79 | 0.83 | 0.77 |
| LAM1 | pY-S | P20700 | Lamin B1 | 0.33 | 0.45 | 0.92 | 0.89 |
| LAMA | Cyto | P02545 | Lamin A/C | 1.05 | -0.38 | 1.38 | -0.07 |

Figure 7-M

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Increased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| LAMA | pY-B | P02545 | Lamin A/C | 0.74 | 0.4 | 0.49 | 0.17 |
| LAMA | pY-S | P02545 | Lamin A/C | 0.57 | 0.27 | 0.4 | 0.09 |
| LAMA3 | pY-B | Q16787 | Laminin alpha-3 chain | 0.58 | 0.62 | 1.28 | 1.37 |
| LAMA3 | pY-S | Q16787 | Laminin alpha-3 chain | 0.19 | 0.53 | 0.84 | 1.14 |
| LDHB | Cyto | P07195 | L-lactate dehydrogenase B chain | 0.82 | 0.75 | 0.99 | 0.96 |
| LDHB | Mem | P07195 | L-lactate dehydrogenase B chain | 0.49 | 1.05 | 0.37 | 0.88 |
| LEG1 | Cyto | P09382 | Galectin-1 | 1.05 | 1.06 | 1.41 | 1.41 |
| LEG1 | Mem | P09382 | Galectin-1 | 0.69 | 0.46 | 1.48 | 1.24 |
| LZTS1 | pY-B | Q9Y250 | Fez1 | 0.59 | 0.28 | 0.93 | 0.61 |
| LZTS2 | pY-B | Q9BRK4 | Fez1 | 0.5 | 0.07 | 1.1 | 0.69 |
| MA32 | Cyto | Q07021 | Hyaluronan-binding protein 1 | 0.01 | 0.32 | 0.2 | 0.57 |
| MA32 | Mem | Q07021 | Hyaluronan-binding protein 1 | 0.81 | 0.15 | 1.35 | 0.72 |
| MA32 | pY-E8P | Q07021 | Hyaluronan-binding protein 1 | 0.71 | 0.32 | 0.32 | -0.14 |
| MA32 | pY-S | Q07021 | Hyaluronan-binding protein 1 | 0.36 | 0.47 | 0.42 | 0.53 |
| MACF4 | pY-B | Q96PK2 | Microtubule-actin crosslinking factor 1 | 0.19 | 0.38 | 0.43 | 0.61 |
| MACF4 | pY-S | Q96PK2 | Microtubule-actin crosslinking factor 1 | 0.05 | 0.36 | 0.25 | 0.5 |
| MAGA4 | Cyto | P43358 | Melanoma-associated antigen 4 | 0.74 | 2.25 | 1.48 | 2.99 |
| MAGA4 | Mem | P43358 | Melanoma-associated antigen 4 | -0.33 | 2.29 | -0.82 | 1.8 |
| MATR3 | Mem | P43243 | Matrin-3 | 1.07 | 0.52 | 1.85 | 1.25 |
| MATR3 | pY-S | P43243 | Matrin-3 | 0.08 | 0.82 | 1.06 | 1.74 |
| MPCP | Mem | Q00325 | Phosphate carrier protein | 0.4 | -0.1 | 0.68 | 0.18 |
| MPCP | pY-S | Q00325 | Phosphate carrier protein | 0.08 | 0.57 | 0.63 | 1.13 |
| MYH10 | Cyto | P35580 | Myosin-10 | 0.82 | 0.29 | 1.34 | 0.82 |
| NEUA | pY-B | Q8NFW8 | N-acylneuraminate cytidylyltransferase | 0.47 | 0.63 | 0.99 | 1.14 |
| NEUA | pY-S | Q8NFW8 | N-acylneuraminate cytidylyltransferase | 0.1 | 0.36 | 0.82 | 1.05 |
| NHPX | pY-B | P55769 | NHP2-like protein 1 | 1.58 | 1.62 | 1.65 | 1.68 |
| NHPX | pY-S | P55769 | NHP2-like protein 1 | 1.39 | 1.25 | 0.97 | 0.8 |
| NOLA1 | pY-B | Q9NY12 | H/ACA ribonucleoprotein subunit 1 | 1.55 | 1.67 | 1.36 | 1.43 |
| NOLC1 | CS | Q14978 | Nucleolar phosphoprotein p130 | 1.1 | 0.96 | 1.26 | 1.25 |

Figure 7-N

| Name | Fraction | Acc | Protein Name | Calu6 vs H292 | H1703 vs H292 | Calu6 vs H358 | H1703 vs H358 |
|---|---|---|---|---|---|---|---|
| *Increased in mesenchymal-like cells* | | | | | | | |
| NOLC1 | Mem | Q14978 | Nucleolar phosphoprotein p130 | 0.01 | 0.34 | 0.26 | 0.59 |
| NOLC1 | pY-B | Q14978 | Nucleolar phosphoprotein p130 | 0.83 | 0.62 | 1.12 | 0.93 |
| NOLC1 | pY-S | Q14978 | Nucleolar phosphoprotein p130 | 1.08 | 0.11 | 0.58 | -0.06 |
| NOVA2 | pY-B | Q9UNW9 | RNA-binding protein Nova-2 | 1.82 | 1.85 | 1.64 | 1.72 |
| NPM | CS | P06748 | Nucleophosmin (NPM) | 0.2 | 0.98 | 0.61 | 1.38 |
| NPM | Cyto | P06748 | Nucleophosmin (NPM) | 0.84 | -0.21 | 1.46 | 0.39 |
| NPM | Mem | P06748 | Nucleophosmin (NPM) | 0.26 | 0.57 | 0.52 | 0.86 |
| NPM | pY-B | P06748 | Nucleophosmin (NPM) | 0.76 | 1.07 | 0.8 | 1.1 |
| NUEM | Mem | Q16795 | NADH-ubiquinone oxidoreductase 39 kDa subunit | 0.46 | 0.4 | 0.84 | 0.88 |
| NUEM | pY-B | Q16795 | NADH-ubiquinone oxidoreductase 39 kDa subunit | 0.79 | 0.87 | 1.61 | 1.69 |
| NUFM | Mem | Q16718 | NADH-ubiquinone oxidoreductase 39 kDa subunit | 0.37 | -0.18 | 0.74 | 0.2 |
| PABP2 | pY-B | Q86U42 | Polyadenylate-binding protein 2 | 0.86 | 0.48 | 0.93 | 0.5 |
| PHB | CS | P35232 | Prohibitin | 3.35 | 0.19 | 1.61 | -0.68 |
| PHB | Mem | P35232 | Prohibitin | 0.6 | 0.92 | 0.65 | 0.95 |
| PHB | pY-B | P35232 | Prohibitin | 1.1 | 0.92 | 0.49 | 0.11 |
| PHB | pY-E8P | P35232 | Prohibitin | -0.1 | 0.38 | 1.35 | 1.83 |
| PHB2 | Mem | Q99623 | Prohibitin-2 | 0.46 | 0.72 | 0.78 | 1.04 |
| PHB2 | pY-B | Q99623 | Prohibitin-2 | 0.32 | 0.16 | 0.55 | 0.39 |
| PHB2 | pY-S | Q99623 | Prohibitin-2 | 0.61 | 0.6 | 0.56 | 0.54 |
| PRP8 | Cyto | Q6P2Q9 | Splicing factor Prp8 | 0.13 | 0.48 | 0.22 | 0.57 |
| PRP8 | Mem | Q6P2Q9 | Splicing factor Prp8 | 0.23 | 0.2 | 0.75 | 0.62 |
| PRP8 | pY-B | Q6P2Q9 | Splicing factor Prp8 | 0.48 | 0.65 | 0.82 | 1.01 |
| PTBP1 | Cyto | P26599 | Polypyrimidine tract-binding protein 1 | 1.21 | 0.23 | 1.58 | 0.58 |
| PTBP1 | Mem | P26599 | Polypyrimidine tract-binding protein 1 | 0.39 | 0.39 | 0.96 | 0.97 |
| PTMS | Cyto | P20962 | Parathymosin | 2.13 | 1.87 | 1.62 | 1.56 |
| PTMS | Mem | P20962 | Parathymosin | 1.89 | 1.23 | 1.5 | 0.82 |
| RAB2A | Mem | P61019 | Rab-2A | 1.18 | 0.51 | 1.36 | 0.69 |
| RALY | pY-B | Q9UKM9 | RNA-binding protein Raly | 1.23 | 0.67 | 1.13 | 0.8 |
| RBM3 | Mem | P98179 | Putative RNA-binding protein 3 | -0.01 | 0.64 | 0.39 | 1 |

Figure 7-O

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Increased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| RBM3 | pY-B | P98179 | Putative RNA-binding protein 3 | 0.32 | 0.37 | 0.59 | 0.64 |
| RL23 | pY-B | P62829 | 60S ribosomal protein L23 | 0.42 | 0.35 | 0.47 | 0.41 |
| RL23 | pY-S | P62829 | 60S ribosomal protein L23 | 0.26 | 0.16 | 0.28 | 0.14 |
| ROA0 | Mem | Q13151 | hnRNP A0 | 0.95 | 0.43 | 1.29 | 0.81 |
| ROA0 | pY-B | Q13151 | hnRNP A0 | 0.38 | 0 | 0.71 | 0.31 |
| ROA2 | Cyto | P22626 | hnRNP A2/B1 | 0.93 | -0.48 | 1.93 | 0.51 |
| ROA2 | Mem | P22626 | hnRNP A2/B1 | 0.55 | 0.32 | 1.32 | 1.08 |
| ROAA | Cyto | Q99729 | hnRNP A/B | 0.39 | 0.23 | 0.78 | 0.62 |
| ROAA | Mem | Q99729 | hnRNP A/B | 0.4 | 0.59 | 0.76 | 0.95 |
| ROAA | pY-B | Q99729 | hnRNP A/B | 0.35 | 0.33 | 0.4 | 0.37 |
| ROAA | pY-S | Q99729 | hnRNP A/B | 0.1 | 0.46 | 0.42 | 0.78 |
| RU2B | Mem | P08579 | U2 small nuclear ribonucleoprotein B | 0.15 | 0.24 | 0.22 | 0.34 |
| RU2B | pY-B | P08579 | U2 small nuclear ribonucleoprotein B | 0.67 | 0.46 | 0.48 | 0.22 |
| RYR3 | pY-B | Q15413 | Ryanodine receptor 3 | 0.72 | 1.01 | 1.2 | 1.53 |
| RYR3 | pY-S | Q15413 | Ryanodine receptor 3 | 0.21 | 0.41 | 0.7 | 0.87 |
| SF3A2 | pY-B | Q15428 | Splicing factor 3A subunit 2 | 1.23 | 0.35 | 1.22 | 0.36 |
| SF3A2 | pY-S | Q15428 | Splicing factor 3A subunit 2 | 1.61 | 1.7 | 2.01 | 2.05 |
| SMD2 | Mem | P62316 | snRNP core protein D2 | 0.47 | 0.56 | 1.31 | 1.28 |
| SMD3 | Mem | P62318 | snRNP core protein D3 | 0.32 | 0.35 | 0.67 | 0.68 |
| SMD3 | pY-B | P62318 | snRNP core protein D3 | 0.58 | 0.31 | 0.49 | 0.24 |
| SMD3 | pY-E8P | P62318 | snRNP core protein D3 | 1.3 | -0.04 | 0.48 | -0.85 |
| SYNE1 | Mem | Q8NF91 | Nesprin-1 | 0.27 | 0.15 | 0.43 | 0.31 |
| SYNE1 | pY-B | Q8NF91 | Nesprin-1 | 0.32 | 0.3 | 0.51 | 0.49 |
| SYNE1 | pY-S | Q8NF91 | Nesprin-1 | 0.34 | 0.54 | 0.71 | 0.91 |
| SYYM | Mem | Q9Y2Z4 | Tyrosine--tRNA ligase | 0.96 | 0.25 | 1.1 | 0.46 |
| TB182 | pY-B | Q9C0C2 | Tankyrase 1-BP | 0.53 | 0.8 | 0.73 | 0.99 |
| TB182 | pY-S | Q9C0C2 | Tankyrase 1-BP | 0.01 | 0.43 | 0.31 | 0.73 |
| TBB3 | Cyto | Q13509 | Tubulin beta-3 | 1.42 | 0.98 | 0.87 | 0.44 |
| THIC | Cyto | Q9BWD1 | Acetyl-CoA acetyltransferase | 1.19 | 0.82 | 0.9 | 0.51 |

Figure 7-P

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Increased in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| THIC | Mem | Q9BWD1 | Acetyl-CoA acetyltransferase | 1.12 | 1.21 | 0.86 | 0.3 |
| THOC4 | pY-B | Q86V81 | bZIP enhancing factor BEF (Aly/REF; Tho4) | 0.34 | 0.71 | 0.5 | 0.85 |
| UBIQ | Cyto | P62988 | Ubiquitin | 0.63 | 0.72 | 0.56 | 0.65 |
| UBIQ | Mem | P62988 | Ubiquitin | 0.03 | 0.47 | -0.11 | 0.37 |
| UBIQ | pY-B | P62988 | Ubiquitin | 0.84 | 0.9 | 1.24 | 1.31 |
| UBIQ | pY-S | P62988 | Ubiquitin | 0.52 | 0.54 | 0.54 | 0.52 |
| UBP5 | Cyto | P45974 | Ubiquitin carboxyl-terminal hydrolase 5 | 0.51 | 1.14 | 0.4 | 1.01 |
| UBP5 | Mem | P45974 | Ubiquitin carboxyl-terminal hydrolase 5 | -0.02 | 0.85 | 0.32 | 1.06 |
| UCR10 | Mem | Q9UDW1 | Ubiquinol-cytochrome c reductase | 0.43 | 0.06 | 0.43 | 0.08 |
| UCR10 | pY-B | Q9UDW1 | Ubiquinol-cytochrome c reductase | 0.6 | 1.28 | 0.41 | 1.04 |
| VIME | CS | P08670 | Vimentin | 2.3 | 2.26 | 2.71 | 2.7 |
| VIME | Mem | P08670 | Vimentin | 2.17 | 0.91 | 2.34 | 1.05 |
| VIME | pY-B | P08670 | Vimentin | 2.51 | 2.71 | 2.51 | 2.73 |
| VIME | pY-E8P | P08670 | Vimentin | 2.21 | 0.22 | 2.39 | 0.42 |
| VIME | pY-S | P08670 | Vimentin | 2.37 | 1.75 | 2.2 | 1.53 |
| VPS16 | Cyto | Q9H269 | Vacuolar protein sorting 16 | 1.2 | 1.23 | 1.42 | 1.44 |
| VPS16 | Mem | Q9H269 | Vacuolar protein sorting 16 | 0.41 | 0.47 | 0.36 | 0.44 |
| ZF64A | pY-B | Q9NPA5 | Zinc finger protein 64 | 0.94 | 1.34 | 2.62 | 2.81 |
| ZF64A | pY-S | Q9NPA5 | Zinc finger protein 64 | 0.5 | 0.99 | 2.1 | 2.8 |

*Mixed abundance in mesenchymal-like cells*

| Name | Fraction | Acc | Protein Name | Calu6 vs H292 | H1703 vs H292 | Calu6 vs H358 | H1703 vs H358 |
|---|---|---|---|---|---|---|---|
| AHNK | CS | Q09666 | AHNAK (Desmoyokin) | -0.73 | -0.34 | -0.68 | -0.34 |
| AHNK | Cyto | Q09666 | AHNAK (Desmoyokin) | -0.42 | -0.34 | -0.37 | -0.32 |
| AHNK | Mem | Q09666 | AHNAK (Desmoyokin) | -0.35 | -0.19 | -0.61 | -0.46 |
| AHNK | pY-S | Q09666 | AHNAK (Desmoyokin) | 0.27 | 0.27 | 0.38 | 0.38 |
| ATPB | pY-S | P06576 | ATP synthase beta chain | -0.4 | -0.21 | -1.24 | -1.05 |
| ATPB | Mem | P06576 | ATP synthase beta chain | 0.56 | 0.02 | 0.94 | 0.4 |
| ATPD | pY-B | P30049 | ATP synthase delta | -0.79 | -2.24 | -0.9 | -2.35 |

Figure 7-Q

| Name | Fraction | Acc | Protein Name | Protein Ratios (log2) | | | |
|---|---|---|---|---|---|---|---|
| | | | | Calu6 vs H292 | H1703 vs H292 | Calu6 vs H358 | H1703 vs H358 |
| *Mixed abundance in mesenchymal-like cells* | | | | | | | |
| ATPD | Mem | P30049 | ATP synthase delta chain | 0.9 | 0.03 | 1.45 | 0.59 |
| CSDE1 | Mem | O75534 | Cold shock domain protein E1 | -0.48 | -0.11 | -0.42 | -0.05 |
| CSDE1 | pY-B | O75534 | Cold shock domain protein E1 | 0.24 | 0.49 | 0.64 | 0.89 |
| CSDE1 | pY-S | O75534 | Cold shock domain protein E1 | 0.6 | 0.78 | 1.04 | 1.23 |
| NCKP1 | pY-B | Q9Y2A7 | Nck-associated protein 1 (NAP 1) | -0.77 | -0.74 | -0.6 | -0.55 |
| NCKP1 | pY-S | Q9Y2A7 | Nck-associated protein 1 (NAP 1) | 1.42 | 1.47 | 0.68 | 0.73 |
| PLAK | Mem | P14923 | Desmoplakin III | -0.83 | -0.97 | -0.78 | -1.3 |
| PLAK | pY-B | P14923 | Desmoplakin III | -1.15 | -1.19 | -0.71 | -0.75 |
| PLAK | pY-E8P | P14923 | Desmoplakin III | 1.33 | 0.31 | 0.8 | 0.27 |
| PLEC1 | Mem | Q15149 | Plectin 1 | -0.16 | -0.28 | -0.46 | -0.58 |
| PLEC1 | pY-B | Q15149 | Plectin 1 | 0.86 | 0.64 | 0.7 | 0.48 |
| PLEC1 | pY-S | Q15149 | Plectin 1 | 0.18 | 0.49 | 0.42 | 0.73 |
| PVR2 | pY-B | Q92692 | Nectin 2 (CD112 antigen). | -0.72 | -0.72 | -1.2 | -1.06 |
| PVR2 | Mem | Q92692 | Nectin 2 (CD112 antigen). | 0.27 | 0.35 | 0.43 | 0.57 |
| RON | pY-B | Q04912 | p185-Ron | -0.72 | -1.23 | -1.64 | -2.1 |
| RON | pY-S | Q04912 | p185-Ron | -0.33 | -0.79 | -1.91 | -2.89 |
| RON | Mem | Q04912 | p185-Ron | 2.8 | -0.2 | 2.79 | -0.21 |
| SHC1 | pY-B | P29353 | SHC1 | -1.05 | -0.5 | -0.64 | -0.16 |
| SHC1 | pY-E8P | P29353 | SHC1 | -0.8 | -0.3 | -0.56 | -0.08 |
| SHC1 | pY-S | P29353 | SHC1 | -0.38 | -0.58 | -0.93 | -0.92 |
| SHC1 | Mem | P29353 | SHC1 | 0.65 | 0.33 | 0.56 | 0.22 |
| ZO2 | pY-B | Q9UDY2 | ZO-2 | -0.44 | -0.84 | -0.28 | -0.5 |
| ZO2 | pY-S | Q9UDY2 | ZO-2 | 0.27 | 0.46 | 0.74 | 0.91 |
| *Decreased in H1703 cells* | | | | | | | |
| AT2A2 | Mem | P16615 | SERCA2 | | -0.84 | | -0.90 |
| CD44 | Mem | P16070 | CD44 antigen | | -1.33 | | -0.72 |
| ERO1A | Mem | Q96HE7 | ERO1-L alpha | | -0.54 | | -1.99 |

Figure 7-R

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

*Decreased in H1703 cells*

| Name | Fraction | Acc | Protein Name | Calu6 vs H292 | H1703 vs H292 | Calu6 vs H358 | H1703 vs H358 |
|---|---|---|---|---|---|---|---|
| GLYM | Mem | P34897 | Serine hydroxymethyltransferase | | -0.44 | | -0.68 |
| GPC5C | pY-S | Q9NQ84 | GPCR RAIG-3 | | -0.39 | | -1.62 |
| ODO2 | Mem | P36957 | Dihydrolipoyllysine succinyltransferase | | -0.47 | | -0.54 |
| PRDX2 | CS | P32119 | Peroxiredoxin 2 | | -1.22 | | -0.48 |
| PRDX2 | Cyto | P32119 | Peroxiredoxin 2 | | -1.18 | | -1.02 |
| PRDX2 | Mem | P32119 | Peroxiredoxin 2 | | -0.71 | | -0.80 |
| RCN1 | pY-S | Q15293 | Reticulocalbin-1 | | -1.41 | | -0.94 |
| RCN1 | Mem | Q15293 | Reticulocalbin-1 | | -1.04 | | -0.54 |
| RCN1 | pY-B | Q15293 | Reticulocalbin-1 | | -0.92 | | -0.73 |
| RS15 | pY-B | P62841 | 40S ribosomal protein S15 (RIG protein) | | -0.50 | | -0.68 |
| RS15 | pY-S | P62841 | 40S ribosomal protein S15 (RIG protein) | | -0.46 | | -0.65 |
| TPD54 | Cyto | O43399 | Tumor protein D54 | | -0.85 | | -1.08 |
| TPD54 | Mem | O43399 | Tumor protein D54 | | -0.71 | | -0.59 |
| TPD54 | pY-B | O43399 | Tumor protein D54 | | -0.35 | | -0.73 |

*Increased in H1703 cells*

| Name | Fraction | Acc | Protein Name | Calu6 vs H292 | H1703 vs H292 | Calu6 vs H358 | H1703 vs H358 |
|---|---|---|---|---|---|---|---|
| AINX | pY-S | Q16352 | Alpha-internexin | | 0.95 | | 1.60 |
| AINX | pY-B | Q16352 | Alpha-internexin | | 2.04 | | 2.34 |
| AL1A1 | Mem | P00352 | Retinal dehydrogenase 1 | | 2.00 | | 2.02 |
| AL1A1 | Cyto | P00352 | Retinal dehydrogenase 1 | | 2.30 | | 2.42 |
| AL3A2 | Mem | P51648 | Fatty aldehyde dehydrogenase | | 0.93 | | 0.80 |
| AL3A2 | CS | P51648 | Fatty aldehyde dehydrogenase | | 1.32 | | 1.36 |
| ASNS | Cyto | P08243 | Asparagine synthetase | | 2.66 | | 1.70 |
| BASP | Cyto | P80723 | Brain acid soluble protein 1 | | 0.26 | | 0.71 |
| BASP | Mem | P80723 | Brain acid soluble protein 1 | | 0.28 | | 0.58 |
| CAV1 | pY-S | Q03135 | Caveolin-1 | | 0.81 | | 0.92 |
| CAV1 | pY-B | Q03135 | Caveolin-1 | | 0.96 | | 1.41 |
| GIT2 | pY-B | Q14161 | ARF GTPase-activating protein | | 0.56 | | 0.94 |

Figure 7-S

| Name | Fraction | Acc | Protein Name | Calu6 vs H292 | H1703 vs H292 | Calu6 vs H358 | H1703 vs H358 |
|---|---|---|---|---|---|---|---|
| *Increased in H1703 cells* | | | | | | | |
| MGN2 | Cyto | Q96A72 | Mago nashi protein homolog 2 | | 2.09 | | 0.64 |
| MK01 | pY-B | P28482 | ERK-2 | | 0.68 | | 0.99 |
| MK14 | pY-S | Q16539 | p38alpha | | 0.50 | | 0.71 |
| MK14 | pY-B | Q16539 | p38alpha | | 0.89 | | 1.37 |
| MK14 | pY-E8P | Q16539 | p38alpha | | 1.41 | | 1.29 |
| NDKB | Mem | P22392 | Nucleoside diphosphate kinase B | | 0.59 | | 1.94 |
| NDKB | Cyto | P22392 | Nucleoside diphosphate kinase B | | 2.16 | | 0.92 |
| NQO1 | Mem | P15559 | NAD(P)H dehydrogenase | | 0.90 | | 1.25 |
| PGFRA | pY-S | P16234 | PDGF-R-alpha | | 0.56 | | 0.78 |
| PGFRA | pY-B | P16234 | PDGF-R-alpha | | 1.27 | | 1.29 |
| PGFRA | pY-E8P | P16234 | PDGF-R-alpha | | 1.70 | | 1.14 |
| PIBF1 | pY-B | Q8WXW3 | Progesterone-induced blocking factor 1 | | 0.42 | | 0.92 |
| PIBF1 | pY-S | Q8WXW3 | Progesterone-induced blocking factor 1 | | 0.49 | | 1.09 |
| PIR | Mem | O00625 | Pirin | | 2.17 | | 2.40 |
| PIR | Cyto | O00625 | Pirin | | 3.14 | | 2.09 |
| PROF1 | Cyto | P07737 | Profilin-1 | | 0.30 | | 0.86 |
| PROF1 | CS | P07737 | Profilin-1 | | 0.31 | | 1.50 |
| PROF1 | Mem | P07737 | Profilin-1 | | 0.69 | | 1.07 |
| PTN11 | pY-B | Q06124 | Tyrosine-protein phosphatase SHP-2 | | 0.78 | | 1.05 |
| PTN11 | pY-S | Q06124 | Tyrosine-protein phosphatase SHP-2 | | 0.78 | | 0.86 |
| PTN11 | pY-E8P | Q06124 | Tyrosine-protein phosphatase SHP-2 | | 2.10 | | 2.82 |
| RBP56 | pY-B | Q92804 | TAF(II)68 | | 0.56 | | 0.89 |
| RBP56 | pY-S | Q92804 | TAF(II)68 | | 0.64 | | 0.77 |
| STAT3 | Mem | P40763 | STAT3 | | 1.08 | | 1.82 |
| STAT3 | Cyto | P40763 | STAT3 | | 1.19 | | 1.84 |
| SYNC | Mem | O43776 | Asparaginyl-tRNA synthetase | | 0.27 | | 0.42 |
| SYNC | Cyto | O43776 | Asparaginyl-tRNA synthetase | | 0.60 | | 0.97 |
| TRXR1 | Mem | Q16881 | Thioredoxin reductase 1 | | 0.55 | | 0.47 |
| TRXR1 | Cyto | Q16881 | Thioredoxin reductase 1 | | 1.27 | | 0.95 |

Figure 7-T

| Name | Fraction | Acc | Protein Name | Protein Ratios (log2) | | |
|---|---|---|---|---|---|---|
| | | | | Calu6 vs H292 | H1703 vs H292 | Calu6 vs H358 | H1703 vs H358 |

| Name | Fraction | Acc | Protein Name | Calu6 vs H292 | H1703 vs H292 | Calu6 vs H358 | H1703 vs H358 |
|---|---|---|---|---|---|---|---|
| *Increased in H1703 cells* | | | | | | | |
| UAP1 | Mem | Q16222 | UDP-N-acetylhexosamine pyrophosphorylase | | 1.38 | | 1.68 |
| UAP1 | Cyto | Q16222 | UDP-N-acetylhexosamine pyrophosphorylase | | 2.21 | | 1.76 |
| UCHL1 | Cyto | P09936 | Ubiquitin carboxyl-terminal hydrolase | | 1.24 | | 2.63 |
| UCHL1 | Mem | P09936 | Ubiquitin carboxyl-terminal hydrolase | | 1.53 | | 1.91 |
| ZYX | Mem | Q15942 | Zyxin | | 0.32 | | 0.87 |
| ZYX | pY-S | Q15942 | Zyxin | | 0.56 | | 1.28 |
| ZYX | pY-B | Q15942 | Zyxin | | 0.60 | | 1.25 |
| *Decreased in Calu6 cells* | | | | | | | |
| 1433B | Cyto | P31946 | 14-3-3 beta/alpha | -0.85 | | -0.28 | |
| 1433B | Mem | P31946 | 14-3-3 beta/alpha | -0.78 | | -0.49 | |
| 1433B | pY-S | P31946 | 14-3-3 beta/alpha | -0.66 | | -0.93 | |
| ARHG7 | pY-B | Q14155 | Rho GEF-7 (p85COOL-1) | -1.40 | | -0.87 | |
| ARHG7 | pY-E8P | Q14155 | Rho GEF-7 (p85COOL-1) | -1.17 | | -0.52 | |
| ARHG7 | pY-S | Q14155 | Rho GEF-7 (p85COOL-1) | -0.64 | | -0.58 | |
| BASP | Cyto | P80723 | Brain acid soluble protein 1 | -1.41 | | -0.97 | |
| BASP | Mem | P80723 | Brain acid soluble protein 1 | -1.09 | | -0.79 | |
| CAV1 | pY-B | Q03135 | Caveolin-1 | -1.19 | | -0.55 | |
| CAV1 | pY-S | Q03135 | Caveolin-1 | -0.86 | | -0.85 | |
| FLNA | Mem | P21333 | Filamin A | -0.48 | | -0.77 | |
| FLNA | Cyto | P21333 | Filamin A | -0.28 | | -0.68 | |
| MK14 | pY-E8P | Q16539 | p38alpha | -1.35 | | -0.65 | |
| MK14 | pY-S | Q16539 | p38alpha | -0.86 | | -0.92 | |
| MK14 | pY-B | Q16539 | p38alpha | -0.73 | | -0.48 | |
| NDKB | Mem | P22392 | Nucleoside diphosphate kinase B | -1.23 | | -1.07 | |
| NDKB | Cyto | P22392 | Nucleoside diphosphate kinase B | -0.58 | | -0.35 | |
| PAXI | pY-B | P49023 | Paxillin | -0.89 | | -0.45 | |
| PAXI | pY-S | P49023 | Paxillin | -0.52 | | -0.31 | |

Figure 7-U

| Name | Fraction | Acc | Protein Name | Protein Ratios (log2) Calu6 vs H292 | H1703 vs H292 | Calu6 vs H358 | H1703 vs H358 |
|---|---|---|---|---|---|---|---|
| *Decreased in Calu6 cells* | | | | | | | |
| PTN11 | pY-B | Q06124 | Tyrosine-protein phosphatase SHP-2 | -1.20 | | -0.93 | |
| RET | Cyto | P07949 | C-ret | -0.25 | | -0.31 | |
| STAT3 | Mem | P40763 | STAT3 | -1.87 | | -1.09 | |
| SYNC | Cyto | O43776 | Asparaginyl-tRNA synthetase | -1.22 | | -0.68 | |
| UCHL1 | Cyto | P09936 | Ubiquitin carboxyl-terminal hydrolase | -1.93 | | -0.51 | |
| UCHL1 | Mem | P09936 | Ubiquitin carboxyl-terminal hydrolase | -0.82 | | -0.43 | |
| *Increased in Calu6 cells* | | | | | | | |
| AN32B | Cyto | Q92688 | Acidic leucine-rich nuclear phosphoprotein 32B | 0.93 | | 1.78 | |
| CD44 | Mem | P16070 | CD44 antigen | 0.76 | | 1.47 | |
| CMC2 | Mem | Q9UJS0 | Calcium-binding Aralar2 | 0.74 | | 0.86 | |
| DECR | Mem | Q16698 | 2,4-dienoyl-CoA reductase | 0.55 | | 1.00 | |
| ETFA | Mem | P13804 | Electron transfer flavoprotein | 1.12 | | 0.96 | |
| FABPE | Cyto | Q01469 | Fatty acid-binding protein (E-FABP) | 2.32 | | 2.76 | |
| FUS | pY-B | P35637 | RNA-binding protein FUS | 0.23 | | 0.57 | |
| FUS | Cyto | P35637 | RNA-binding protein FUS | 0.86 | | 1.51 | |
| FUS | pY-E8P | P35637 | RNA-binding protein FUS | 2.05 | | 0.48 | |
| GLSK | Mem | O94925 | K-glutaminase | 1.32 | | 1.40 | |
| KCRU | Mem | P12532 | Creatine kinase, mitochondrial | 1.97 | | 2.56 | |
| LPXN | pY-B | O60711 | Leupaxin | 2.59 | | 2.57 | |
| LPXN | pY-S | O60711 | Leupaxin | 2.80 | | 2.81 | |
| MARCS | Cyto | P29966 | Myristoylated alanine-rich C-kinase substrate | 0.45 | | 0.95 | |
| MARCS | Mem | P29966 | Myristoylated alanine-rich C-kinase substrate | 0.71 | | 0.50 | |
| RAB2A | Mem | P61019 | Ras-related protein Rab-2A | 0.99 | | 0.61 | |
| RAB7 | Mem | P51149 | Ras-related protein Rab-7 | 1.13 | | 0.95 | |
| RAP1B | Mem | P61224 | Ras-related protein Rap-1b | 0.88 | | 0.88 | |
| RET | pY-S | P07949 | C-ret | 0.96 | | 1.66 | |
| RET | pY-B | P07949 | C-ret | 1.82 | | 1.10 | |

Figure 7-V

| Name | Fraction | Acc | Protein Name | Protein Ratios (log2) | | |
|------|----------|-----|--------------|---------|---------|---------|
| | | | | Calu6 vs H292 | H1703 vs H292 | Calu6 vs H358 | H1703 vs H358 |

*Increased in Calu6 cells*

| Name | Fraction | Acc | Protein Name | Calu6 vs H292 | H1703 vs H292 | Calu6 vs H358 | H1703 vs H358 |
|------|----------|-----|--------------|---------------|---------------|---------------|---------------|
| STAT3 | pY-B | P40763 | STAT3 | 1.12 | | 1.22 | |

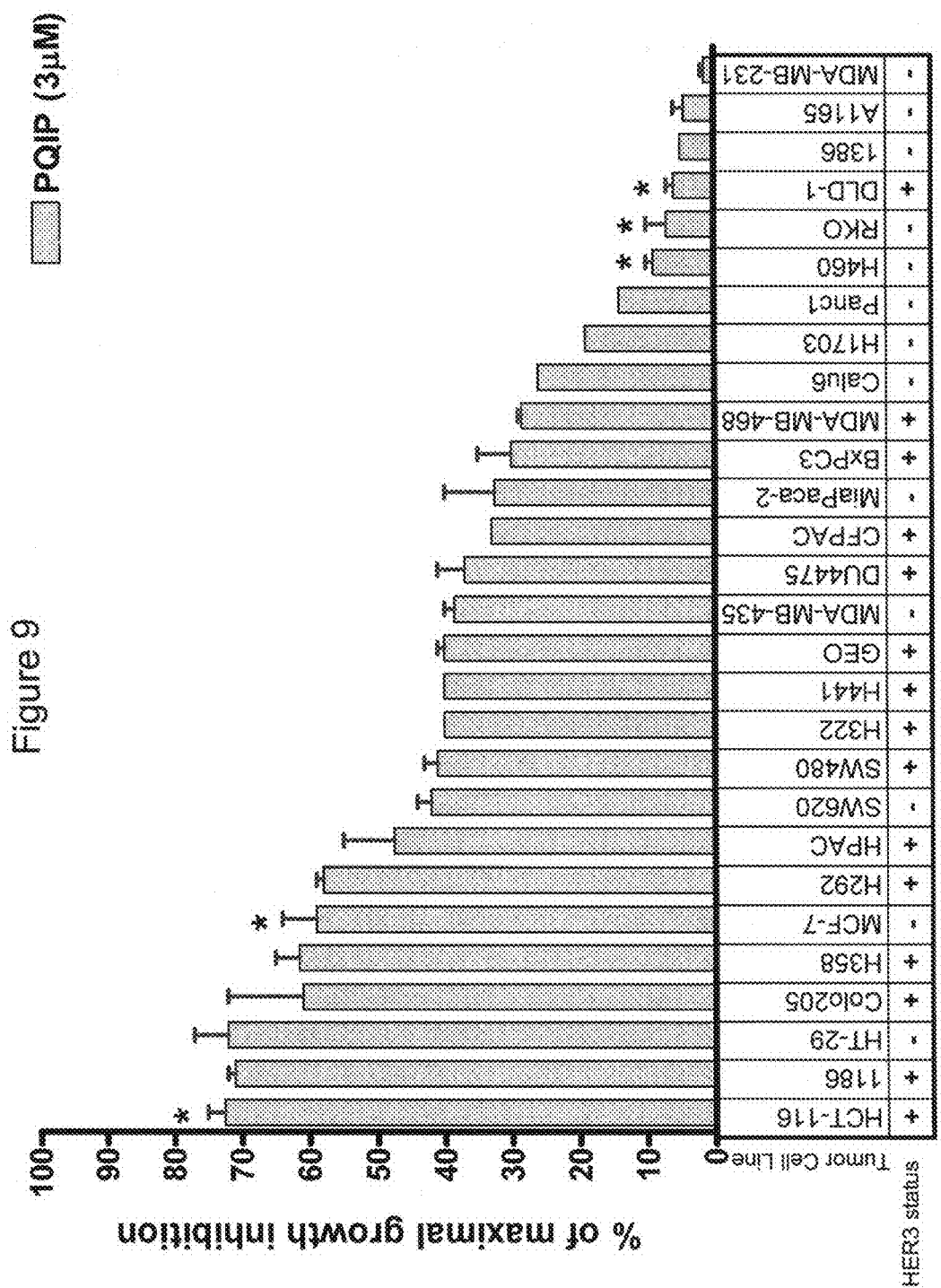

BIOLOGICAL MARKERS PREDICTIVE OF ANTI-CANCER RESPONSE TO INSULIN-LIKE GROWTH FACTOR-1 RECEPTOR KINASE INHIBITORS

CROSS-REFERENCE TO RELATED APPLICATIONS

This application claims the benefit of U.S. Provisional Application No. 60/997,514, filed Oct. 3, 2007, which is herein incorporated by reference in its entirety.

BACKGROUND OF THE INVENTION

The present invention is directed to methods for diagnosing and treating cancer patients. In particular, the present invention is directed to methods for determining which patients will most benefit from treatment with an insulin-like growth factor-1 receptor (IGF-1R) kinase inhibitor.

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth. A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

The IGF-1 pathway in human tumor development has an important role. IGF-1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF-1R is required for establishment and maintenance of the transformed phenotype in vitro and in vivo (Baserga R. Exp. Cell. Res., 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

It has been recognized that inhibitors of protein-tyrosine kinases are useful as selective inhibitors of the growth of mammalian cancer cells. For example, Gleevec™ (also known as imatinib mesylate), a 2-phenylpyrimidine tyrosine kinase inhibitor that inhibits the kinase activity of the BCR-ABL fusion gene product, has been approved by the U.S. Food and Drug Administration for the treatment of CML. The 4-anilinoquinazoline compound Tarceva™ (erlotinib HCl) has also been recently approved by the FDA, and selectively inhibits EGF receptor kinase with high potency. The development for use as anti-tumor agents of compounds that directly inhibit the kinase activity of IGF-1R, as well as antibodies that reduce IGF-1R kinase activity by blocking IGF-1R activation or antisense oligonucleotides that block IGF-1R expression, are areas of intense research effort (e.g. see Larsson, O. et al (2005) Brit. J. Cancer 92:2097-2101; Ibrahim, Y. H. and Yee, D. (2005) Clin. Cancer Res. 11:944s-950s; Mitsiades, C. S. et al. (2004) Cancer Cell 5:221-230; Camirand, A. et al. (2005) Breast Cancer Research 7:R570-R579 (DOI 10.1186/bcr1028); Camirand, A. and Pollak, M. (2004) Brit. J. Cancer 90:1825-1829; Garcia-Echeverria, C. et al. (2004) Cancer Cell 5:231-239).

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as protein-tyrosine kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone).

Target-specific therapeutic approaches are generally associated with reduced toxicity compared with conventional cytotoxic agents, and therefore lend themselves to use in combination regimens.

Several groups have investigated potential biomarkers to predict a patient's response to protein-tyrosine kinase inhibitors, for example EGFR inhibitors (see for example, PCT publications: WO 2004/063709, WO 2005/017493, WO 2004/111273, and WO 2004/071572; and US published patent applications: US 2005/0019785, and US 2004/0132097). However, no diagnostic or prognostic tests have yet emerged that can guide practicing physicians in the treatment of their patients with such inhibitors.

Thus, there remains a critical need for improved methods for determining the best mode of treatment for any given cancer patient. The present invention provides methods for determining which tumors will respond most effectively to treatment with IGF-1R kinase inhibitors based on whether the tumor cells have undergone an epithelial to mesenchymal transition ("EMT"; Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515), and for the incorporation of such determinations into more effective treatment regimens for cancer patients, whether such inhibitors are used as single agents or combined with other anti-cancer agents.

SUMMARY OF THE INVENTION

The present invention provides diagnostic and prognostic methods for predicting the effectiveness of treatment of a cancer patient with an IGF-1R kinase inhibitor. Based on the surprising discovery that the sensitivity of tumor cell growth to inhibition by IGF-1R kinase inhibitors is dependent on whether such tumor cells have undergone an EMT, methods have been devised for determining epithelial and/or mesenchymal biomarkers to predict the sensitivity of tumor cells to IGF-1R kinase inhibitors.

Accordingly, the present invention provides a method of predicting the sensitivity of tumor cell growth to inhibition by an IGF-1R kinase inhibitor, comprising: assessing the level of an epithelial biomarker expressed by a tumor cell; and predicting the sensitivity of tumor cell growth to inhibition by an IGF-1R kinase inhibitor, wherein high expression levels of tumor cell epithelial biomarkers correlate with high sensitivity to inhibition by IGF-1R kinase inhibitors.

The present invention also provides a method of predicting the sensitivity of tumor cell growth to inhibition by an IGF-1R kinase inhibitor, comprising: assessing the level of a mesenchymal biomarker expressed by a tumor cell; and predicting the sensitivity of tumor cell growth to inhibition by an IGF-1R kinase inhibitor, wherein high expression levels of tumor cell mesenchymal biomarkers correlate with low sensitivity to inhibition by IGF-1R kinase inhibitors.

Improved methods for treating cancer patients with IGF-1R kinase inhibitors that incorporate the above methodology are also provided. Thus, the present invention further provides a method for treating tumors or tumor metastases in a patient, comprising the steps of diagnosing a patient's likely responsiveness to an IGF-1R kinase inhibitor by assessing whether the tumor cells have undergone an epithelial-mesenchymal transition, and administering to said patient a therapeutically effective amount of an IGF-1R kinase inhibitor.

Additionally, methods are provided for the identification of new epithelial or mesenchymal biomarkers that are predictive of responsiveness of tumors to IGF-1R kinase inhibitors.

Thus, for example, the present invention further provides a method of identifying an epithelial biomarker that is diagnostic for more effective treatment of a neoplastic condition with an IGF-1R kinase inhibitor, comprising: measuring the level of a candidate epithelial biomarker in neoplastic cell-containing samples from patients with a neoplastic condition, and identifying a correlation between the level of said candidate epithelial biomarker in the sample from the patient with the effectiveness of treatment of the neoplastic condition with an IGF-1R kinase inhibitor, wherein a correlation of high levels of the epithelial biomarker with more effective treatment of the neoplastic condition with an IGF-1R kinase inhibitor indicates that said epithelial biomarker is diagnostic for more effective treatment of the neoplastic condition with an IGF-1R kinase inhibitor.

The present invention further provides a method of identifying a mesenchymal biomarker that is diagnostic for less effective treatment of a neoplastic condition with an IGF-1R kinase inhibitor, comprising: (a) measuring the level of a candidate mesenchymal biomarker in neoplastic cell-containing samples from patients with a neoplastic condition, and (b) identifying a correlation between the level of said candidate mesenchymal biomarker in the sample from the patient with the effectiveness of treatment of the neoplastic condition with an IGF-1R kinase inhibitor, wherein a correlation of high levels of the mesenchymal biomarker with less effective treatment of the neoplastic condition with an IGF-1R kinase inhibitor indicates that said mesenchymal biomarker is diagnostic for less effective treatment of the neoplastic condition with an IGF-1R kinase inhibitor.

Furthermore, methods for the identification of agents that restore the sensitivity of tumor cells that have undergone EMT to inhibition by IGF-1R kinase inhibitors are also provided. Thus, for example, the present invention provides a method for the identification of an agent that enhances sensitivity of the growth of a tumor cell to an IGF-1R kinase inhibitor, said tumor cell having being characterized as one that has previously undergone an epithelial-mesenchymal transition, comprising contacting a sample of said tumor cells with an IGF-1R kinase inhibitor, contacting an identical sample of said tumor cells with an IGF-1R kinase inhibitor in the presence of a test agent, comparing the IGF-1R kinase inhibitor-mediated growth inhibition in the presence and absence of the test agent, and determining whether the test agent is an agent that enhances sensitivity of the growth of the tumor cell to an IGF-1R kinase inhibitor.

The present invention also provides a method of predicting the sensitivity of tumor cell growth to inhibition by an IGF-1R kinase inhibitor, comprising: assessing the level of the biomarker pErk expressed by a tumor cell; and predicting the sensitivity of tumor cell growth to inhibition by an IGF-1R kinase inhibitor, wherein high levels of biomarker pErk expression by tumor cells correlates with low sensitivity to inhibition by IGF-1R kinase inhibitors.

The present invention also provides a method for treating tumors or tumor metastases in a patient, comprising the steps of: diagnosing a patient's likely responsiveness to an IGF-1R kinase inhibitor by assessing the level of the biomarker pErk expressed by the tumor cells of the patient, wherein high levels of biomarker pErk expression by tumor cells correlates with low sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor.

The present invention also provides a method for treating tumors or tumor metastases in a patient, comprising the steps of: diagnosing a patient's likely responsiveness to an IGF-1R kinase inhibitor by assessing the level of the biomarker HER3 expressed by the tumor cells of the patient, wherein high levels of biomarker HER3 expression by tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor.

The present invention also provides a method for treating tumors or tumor metastases in a patient, comprising the steps of: diagnosing a patient's likely responsiveness to an IGF-1R kinase inhibitor by assessing the level of the biomarker pHER3 expressed by the tumor cells of the patient, wherein high levels of biomarker pHER3 expression by tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor.

BRIEF DESCRIPTION OF THE FIGURES

FIG. 7(A-V): Proteins identified by cell fractionation and mass spectrometry that are up regulated or down regulated in epithelial (H292, H1358) or mesenchymal (Calu6, H1703) tumor cell types. Proteins are listed as being (a) decreased in cells after EMT (i.e. epithelial markers); (b) increased in cells after EMT (i.e. mesenchymal markers); (c) mixed abundance in cells after EMT; (d) decreased in H1703 mesenchymal cells; (e) increased in H1703 mesenchymal cells; (f) decreased in Calu6 mesenchymal cells; and (g) increased in Calu6 mesenchymal cells. Protein levels were assessed in the following fractions: Cytosol (Cyto); Membrane (Mem); Cell Surface (CS); and phosphotyrosine-containing fractions, basal (pY-B); after serum stimulation of cells (pY-S); and after EGF stimulation of cells (pY-E8P). "Acc" refers to the Genbank Accession number of the named protein. Protein ratios are expressed as $\log_2$ values.

FIG. 9: High levels of HER3 expression are predictive of sensitivity to the IGF-1R kinase inhibitor PQIP in a panel of 28 tumor cell lines. Her3 expression was determined by immunoblotting analysis of cell extracts using an anti-HER3 antibody. HER3-expressing cells are indicated by a (+), and cells with no detectable HER3 are indicated by a (−). Those tumor cell lines which harbor a known activating mutation in PI3K are marked by a *.

DETAILED DESCRIPTION OF THE INVENTION

Figure 1:
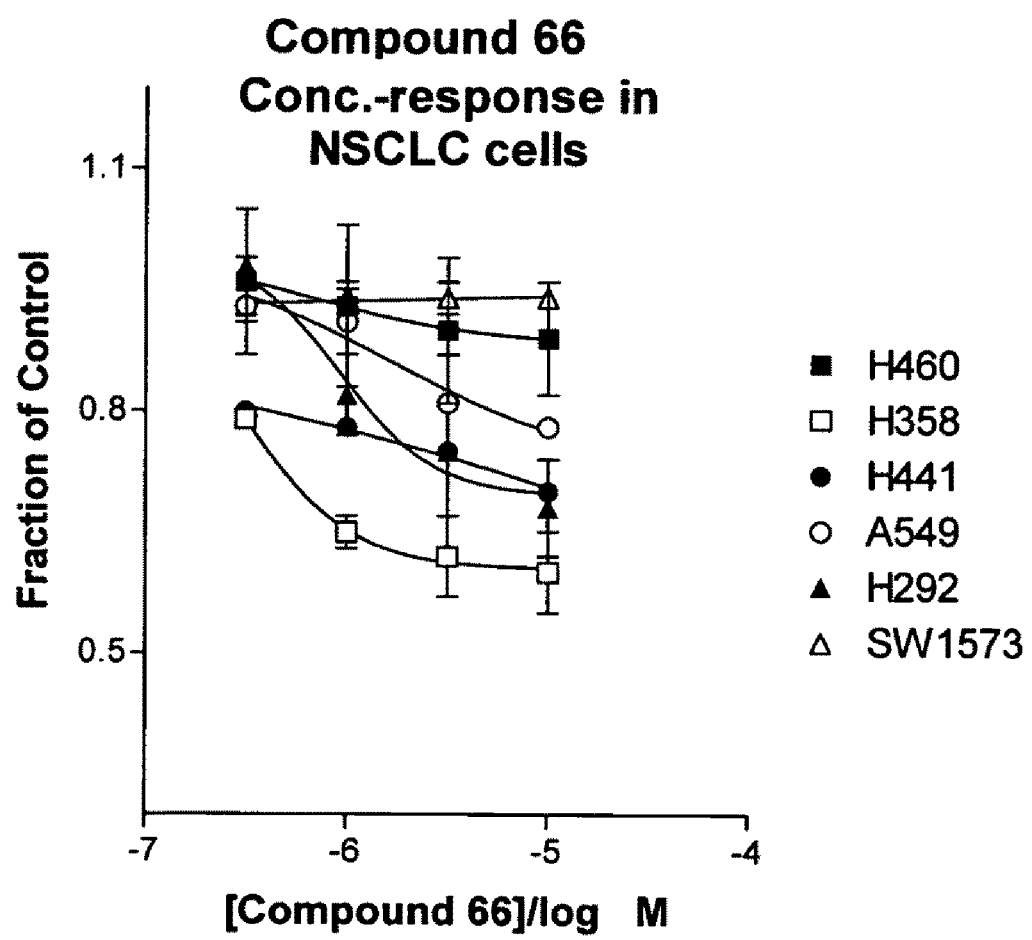
FIG. 1: Sensitivity of NSCLC cell lines to IGF-1R kinase inhibitor Compound 66.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The data presented in the Examples herein below demonstrate that tumor cells, such as NSCLC cells, grown either in cell culture or in vivo, show a range of sensitivities to inhibition by IGF-1R kinase inhibitors, dependent on whether they have undergone an epithelial to mesenchymal transition (EMT). Prior to EMT, tumor cells are very sensitive to inhibition by IGF-1R kinase inhibitors such as Compound 66, a potent (approx. 50 nM $IC_{50}$) and IGF-1R-selective low molecular weight IGF-1R kinase inhibitor, whereas tumor cells which have undergone an EMT are substantially less sensitive to inhibition by such compounds. The data indicates that the EMT may be a "general biological switch" that determines the level of sensitivity of tumors to IGF-1R kinase inhibitors. It is demonstrated that the level of sensitivity of tumors to IGF-1R kinase inhibitors can be assessed by determining the level of biomarkers expressed by a tumor cell that are characteristic for cells either prior to or subsequent to an EMT event. For example, high levels of tumor cell expression of epithelial biomarkers such as E-cadherin, indicative of a cell that has not yet undergone an EMT, correlate with high sensitivity to IGF-1R kinase inhibitors. Conversely, high levels of tumor cell expression of mesenchymal biomarkers such as vimentin, fibronectin, Snail, Zeb1, or Sip1, indicative of a cell that has undergone an EMT, correlate with low sensitivity to IGF-1R kinase inhibitors. An alternative indicator of the EMT status of cells is the methylation status of the E-cadherin gene (CDH1) promoter, which is an indicator of transcriptional repression. CDH1 promoter methylation indicates that tumor cells have undergone an EMT transition. The data herein demonstrates that the degree of sensitivity of tumor cells to IGF1R kinase inhibitors correlates with the methylation status of the CDH1 gene, with tumor cells where low or no CDH1 promoter methylation is observed demonstrating significantly greater sensitivity to IGF1R kinase inhibitors. Additionally, morphometric cell analysis can be used to provide information on epithelial or mesenchymal status of tumor cells and their subsequent sensitivity to inhibition by IGF-1R kinase inhibitors. Finally, the data presented herein demonstrate that the level of pErk in tumor cells can be used to predict sensitivity to IGF1R kinase inhibitors, with lower pErk levels predicting greater sensitivity to IGF1R kinase inhibitors, and that the level of HER3 or pHER3 in tumor cells can be used to predict sensitivity to IGF1R kinase inhibitors, with higher HER3 or pHER3 levels predicting greater sensitivity to IGF1R kinase inhibitors. Thus, these observations can form the basis of valuable new diagnostic methods for predicting the effects of IGF-1R kinase inhibitors on tumor growth, and give oncologists additional tools to assist them in choosing the most appropriate treatment for their patients.

Accordingly, the present invention provides a method of predicting the sensitivity of tumor cell growth to inhibition by an IGF-1R kinase inhibitor, comprising: assessing the level of an epithelial biomarker expressed by a tumor cell; and predicting the sensitivity of tumor cell growth to inhibition by an IGF-1R kinase inhibitor, wherein high expression levels of tumor cell epithelial biomarkers correlate with high sensitivity to inhibition by IGF-1R kinase inhibitors. Preferred examples of epithelial biomarkers include E-cadherin and Brk (i.e. PTK-6) (see Table 1). Additional examples of epithelial biomarkers that can be utilized in the method of this invention include γ-catenin (i.e. junction plakoglobin), α-catenin (i.e. α1, α2, or α3 catenin), keratin 8, and keratin 18 (see Table 1).

The present invention also provides a method of predicting the sensitivity of tumor cell growth to inhibition by an IGF-1R kinase inhibitor, comprising: assessing the level of a mesenchymal biomarker expressed by a tumor cell; and predicting the sensitivity of tumor cell growth to inhibition by an IGF-1R kinase inhibitor, wherein high expression levels of tumor cell mesenchymal biomarkers correlate with low sensitivity to inhibition by IGF-1R kinase inhibitors. Preferred examples of mesenchymal biomarkers include vimentin and fibronectin (see Table 1). Additional examples of mesenchymal biomarkers that can be utilized in the method of this invention include fibrillin-1, fibrillin-2, collagen alpha-2(IV), collagen alpha-2(V), LOXL1, nidogen, C11orf9, tenascin, N-cadherin, and embryonal $EDB^+$ fibronectin (see Table 1).

In the practice of this invention, with preferred epithelial biomarkers, the level of expression in tumor cells that are sensitive to IGF-1R kinase inhibitors will generally be at such a high level that the biomarker will be very readily detectable, using for example a specific anti-biomarker antibody for detection. With preferred epithelial biomarkers, the level of expression in tumor cells that are relatively insensitive to IGF-1R kinase inhibitors will generally be at such a low level that the biomarker will be barely detectable, if at all, using similar procedures (e.g. in the data presented in the Examples herein below, compare E-cadherin levels between sensitive and relatively insensitive tumor cells in FIGS. 2 and 3).

However, for other less preferred epithelial biomarkers, the level of biomarker expression in tumor cells that are relatively insensitive to IGF-1R kinase inhibitors may be readily detectable, but nevertheless will be at a substantially lower level of expression than in tumor cells that are sensitive to IGF-1R kinase inhibitors (e.g., in the data presented in the Examples herein below, compare α-catenin levels for the relatively insensitive tumor cell SW1573 with the sensitive tumor cells H441, H358, and H292 in FIG. 2).

Similarly, in the practice of this invention, with preferred mesenchymal biomarkers, the level of expression in tumor cells that are relatively insensitive to IGF-1R kinase inhibitors will generally be at such a high level that the biomarker will be very readily detectable, using for example a specific anti-biomarker antibody for detection. With preferred mesenchymal biomarkers, the level of expression in tumor cells that are relatively sensitive to IGF-1R kinase inhibitors will generally be at such a low level that the biomarker will be barely detectable, if at all, using similar procedures (e.g. in the data presented in the Examples herein below, compare fibronectin or vimentin levels between sensitive and relatively insensitive tumor cells in FIGS. 2 and 3).

Also, for other less preferred mesenchymal biomarkers, the level of biomarker expression in tumor cells that are relatively sensitive to IGF-1R kinase inhibitors may be readily detectable, but nevertheless will be at a substantially lower level of expression than in tumor cells that are relatively insensitive to IGF-1R kinase inhibitors.

For any given epithelial or mesenchymal biomarker, the range of expression level between tumor cells that are relatively insensitive to IGF-1R kinase inhibitors and those that are sensitive, can readily be assessed by one of skill in the art, for example by testing on a panel of tumor cells as described herein (e.g. FIG. 2), or by testing in tumor biopsies from patients whose tumors display a range of sensitivities to an IGF-1R kinase inhibitor (e.g. Compound 66).

In the context of this invention, for a relatively small percentage of tumor cells that are relatively insensitive to IGF-1R kinase inhibitors, the methods described above for predicting the sensitivity of tumor cell growth to inhibition by an IGF-1R kinase inhibitor, comprising assessing the level of an epithelial or mesenchymal biomarker expressed by a tumor cell, in circumstances where only a single biomarker level is assessed, may falsely predict that tumor cell growth is sensitive to inhibition by an IGF-1R kinase inhibitor. For example, in the data presented in the Examples herein below, the levels of the epithelial biomarkers γ-catenin and α-catenin in H460 tumor cells, or the mesenchymal biomarker vimentin in H460 cells, falsely predict high sensitivity to IGF-1R kinase inhibitors (see FIG. 2). Thus, based on such false predictions, a physician may be lead to treat a small number of patients with IGF-1R kinase inhibitors, and the tumor may not be sensitive to the inhibitor. However, for the vast majority of tumor cells (e.g. at least 90%, from the data presented in the Examples herein below), assessment of a single biomarker expression level would be expected to provide an accurate prediction of level of sensitivity to IGF-1R kinase inhibitors.

Furthermore, most importantly in the context of this invention, no tumor cells that are sensitive to IGF-1R kinase inhibitors have been found that when tested by the above methods (where only a single biomarker level is assessed) give a false prediction that tumor cell growth will be insensitive to inhibition by an IGF-1R kinase inhibitor. Thus, utilizing the testing methods described herein should never lead a physician to withhold treatment with an IGF-1R kinase inhibitor in cases where the patient may benefit from such treatment.

In addition, one of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgement of the attending physician to determine the most appropriate course of treatment for an individual patient, based upon test results, patient condition and history, and his own experience. There may even be occasions, for example, when a physician will choose to treat a patient with an IGF-1R kinase inhibitor even when a tumor is not predicted to be particularly sensitive to IGF-1R kinase inhibitors, based on data from diagnostic tests or from other criteria, particularly if all or most of the other obvious treatment options have failed, or if some synergy is anticipated when given with another treatment. The fact that the IGF-1R kinase inhibitors as a class of compounds are relatively well tolerated compared to many other anti-cancer compounds, such as more traditional chemotherapy or cytotoxic agents used in the treatment of cancer, makes this a more viable option. Also, it should be noted that while the biomarkers disclosed herein predict which patients with tumors are likely to receive the most benefit from IGF-1R kinase inhibitors, it does not necessarily mean that patients with tumors which do not possess the optimal biomarker signature will receive no benefit, just that a more modest effect is to be anticipated.

Preferred examples of suitable epithelial biomarkers for use in this invention, such as E-cadherin, do not lead to any false predictions when used in the methods described above (where only a single biomarker level is assessed).

Furthermore, this invention also provides additional methods wherein simultaneous assessment of the expression level in tumor cells of more than one biomarker level is utilized. In preferred embodiments of these methods (described below) there is no level of false prediction, as is the case for some of the methods described above where a single biomarker expression level is assessed.

Accordingly, the present invention provides a method of predicting the sensitivity of tumor cell growth to inhibition by an IGF-1R kinase inhibitor, comprising: assessing the level of one or more (or a panel of) epithelial biomarkers expressed by a tumor cell; and predicting the sensitivity of tumor cell growth to inhibition by an IGF-1R kinase inhibitor, wherein simultaneous high expression levels of all of the assessed tumor cell epithelial biomarkers correlates with high sensitivity to inhibition by IGF-1R kinase inhibitors. In one preferred embodiment of this method the epithelial biomarkers comprise E-cadherin and Brk, wherein simultaneous high expression level of the two tumor cell epithelial biomarkers correlates with high sensitivity to inhibition by IGF-1R kinase inhibitor. In another preferred embodiment of this method the epithelial biomarkers comprise E-cadherin and γ-catenin, wherein simultaneous high expression level of the two tumor cell epithelial biomarkers correlates with high sensitivity to inhibition by IGF-1R kinase inhibitor. Note that in the two latter preferred embodiments a high expression level of both biomarkers is required to indicate high sensitivity.

The present invention also provides a method of predicting the sensitivity of tumor cell growth to inhibition by an IGF-1R kinase inhibitor, comprising: assessing the level of one or more (or a panel of) mesenchymal biomarkers expressed by a tumor cell; and predicting the sensitivity of tumor cell growth to inhibition by an IGF-1R kinase inhibitor, wherein simultaneous low or undetectable expression levels of all of the assessed tumor cell mesenchymal biomarkers correlates with high sensitivity to inhibition by IGF-1R kinase inhibitors. In one preferred embodiment of this method the mesenchymal biomarkers comprise vimentin and fibronectin, wherein simultaneous low or undetectable expression level of the two tumor cell mesenchymal biomarkers correlates with high sensitivity to inhibition by IGF-1R kinase inhibitor. Note that in the latter preferred embodiment a low or undetectable expression of both biomarkers is required to indicate high sensitivity.

The present invention also provides a method of predicting the sensitivity of tumor cell growth to inhibition by an IGF-1R kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an IGF-1R kinase inhibitor, wherein a high ratio of epithelial to mesenchymal biomarker expression levels correlates with high sensitivity to inhibition by IGF-1R kinase inhibitors. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

The present invention also provides a method of predicting the sensitivity of tumor growth to inhibition by an IGF-1R kinase inhibitor, comprising: assessing the level of one or more (or a panel of) epithelial biomarkers expressed by cells of the tumor; and predicting the sensitivity of tumor growth to inhibition by an IGF-1R kinase inhibitor, wherein simultaneous high expression levels of all of the assessed tumor cell epithelial biomarkers correlates with high sensitivity to inhibition by IGF-1R kinase inhibitors. In one preferred embodiment of this method the epithelial biomarkers comprise E-cadherin and Brk, wherein simultaneous high expression level of the two tumor cell epithelial biomarkers correlates with high sensitivity to inhibition by IGF-1R kinase inhibitor. In another preferred embodiment of this method the epithelial biomarkers comprise E-cadherin and γ-catenin, wherein simultaneous high expression level of the two tumor cell epithelial biomarkers correlates with high sensitivity to inhibition by IGF-1R kinase inhibitor. Note that in the two latter preferred embodiments a high expression level of both biomarkers is required to indicate high sensitivity.

The present invention also provides a method of predicting the sensitivity of tumor growth to inhibition by an IGF-1R kinase inhibitor, comprising: assessing the level of one or more (or a panel of) mesenchymal biomarkers expressed by cells of the tumor; and predicting the sensitivity of tumor growth to inhibition by an IGF-1R kinase inhibitor, wherein simultaneous low or undetectable expression levels of all of the assessed tumor cell mesenchymal biomarkers correlates with high sensitivity to inhibition by IGF-1R kinase inhibitors. In one preferred embodiment of this method the mesenchymal biomarkers comprise vimentin and fibronectin, wherein simultaneous low or undetectable expression level of the two tumor cell mesenchymal biomarkers correlates with high sensitivity to inhibition by IGF-1R kinase inhibitor. Note that in the latter preferred embodiment a low or undetectable expression of both biomarkers is required to indicate high sensitivity.

The present invention also provides a method of predicting the sensitivity of tumor growth to inhibition by an IGF-1R kinase inhibitor, comprising: assessing the level of an epithelial biomarker expressed by cells of the tumor; assessing the level of a mesenchymal biomarker expressed by cells of the tumor; and predicting the sensitivity of tumor growth to inhibition by an IGF-1R kinase inhibitor, wherein a high ratio of epithelial to mesenchymal biomarker expression levels correlates with high sensitivity to inhibition by IGF-1R kinase inhibitors. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

The present invention also provides a method of predicting whether a cancer patient is afflicted with a tumor that will respond effectively to treatment with an IGF-1R kinase inhibitor, comprising: assessing the level of one or more (or a panel of) epithelial biomarkers expressed by cells of the tumor; and predicting if the tumor will respond effectively to treatment with an IGF-1R kinase inhibitor, wherein simultaneous high expression levels of all of the tumor cell epithelial biomarkers correlates with a tumor that will respond effectively to treatment with an IGF-1R kinase inhibitor. In one preferred embodiment of this method the epithelial biomarkers comprise E-cadherin and Brk, wherein simultaneous high expression level of the two tumor cell epithelial biomarkers correlates with a tumor that will respond effectively to treatment with an IGF-1R kinase inhibitor. In another preferred embodiment of this method the epithelial biomarkers comprise E-cadherin and γ-catenin, wherein simultaneous high expression level of the two tumor cell epithelial biomarkers correlates with a tumor that will respond effectively to treatment with an IGF-1R kinase inhibitor. Note that in the two latter preferred embodiments a high expression level of both biomarkers is required to indicate a tumor that will respond effectively to treatment with an IGF-1R kinase inhibitor.

The present invention also provides a method of predicting whether a cancer patient is afflicted with a tumor that will respond effectively to treatment with an IGF-1R kinase inhibitor, comprising: assessing the level of one or more (or a panel of) mesenchymal biomarkers expressed by cells of the tumor; and predicting if the tumor will respond effectively to treatment with an IGF-1R kinase inhibitor, wherein simultaneous low or undetectable expression levels of all of the tumor cell mesenchymal biomarkers correlates with a tumor that will respond effectively to treatment with an IGF-1R kinase inhibitor. In one preferred embodiment of this method the mesenchymal biomarkers comprise vimentin and fibronectin, wherein simultaneous low or undetectable expression level of the two tumor cell mesenchymal biomarkers correlates with a tumor that will respond effectively to treatment with an IGF-1R kinase inhibitor. Note that in the latter preferred embodiment a low or undetectable expression of both biomarkers is required to indicate a tumor that will respond effectively to treatment with an IGF-1R kinase inhibitor.

The present invention also provides a method of predicting whether a cancer patient is afflicted with a tumor that will respond effectively to treatment with an IGF-1R kinase inhibitor, comprising: assessing the level of an epithelial biomarker expressed by cells of the tumor; assessing the level of a mesenchymal biomarker expressed by cells of the tumor; and predicting if the tumor will respond effectively to treatment with an IGF-1R kinase inhibitor, wherein a high ratio of epithelial to mesenchymal biomarker expression levels correlates with a tumor that will respond effectively to treatment with an IGF-1R kinase inhibitor. In one preferred embodiment of this method the epithelial biomarker comprises E-cadherin and the mesenchymal biomarker comprises fibronectin. In another preferred embodiment of this method the epithelial biomarker comprises Brk and the mesenchymal biomarker comprises fibronectin. In another preferred embodiment of this method the epithelial biomarker comprises E-cadherin and the mesenchymal biomarker comprises vimentin. In another preferred embodiment of this method the epithelial biomarker comprises γ-catenin and the mesenchymal biomarker comprises fibronectin.

In the context of the methods of this invention, epithelial or mesenchymal biomarkers expressed by a tumor cell can include molecular and cellular markers that indicate the transition state of the tumor cell. In a preferred embodiment the biomarker is an individual marker protein, or its encoding mRNA, characteristic of the particular transition state of the tumor, i.e. a tumor exhibiting epithelial or mesenchymal characteristics. In an alternative embodiment, in certain circumstances the biomarker may be a characteristic morphological pattern produced in the tumor cell by cellular macromolecules that is characteristic of either an epithelial or mesenchymal condition. Thus, morphometric cell analysis can be used to provide information on epithelial or mesenchymal status of tumor cells and their subsequent sensitivity to inhibition by IGF-1R kinase inhibitors. In an additional preferred embodiment the biomarker that indicates the transition state of the tumor cell is methylation of the E-Cadherin gene (CDH1) promoter. CDH1 promoter methylation indicates that tumor cells have undergone an EMT transition.

TABLE 1

Molecular Biomarker Gene Identification

| Human Biomarker | NCBI GeneID[1] | NCBI RefSeq[2] |
|---|---|---|
| E-cadherin | 999 | NP_004351 |
| Brk | 5753 | NP_005966 |
| γ-catenin | 3728 | NP_002221 |
| α1-catenin | 1495 | NP_001894 |
| α2-catenin | 1496 | NP_004380 |
| α3-catenin | 29119 | NP_037398 |
| keratin 8 | 3856 | NP_002264 |
| keratin 18 | 3875 | NP_000215 |
| vimentin | 7431 | NP_003371 |
| fibronectin 1 | 2335 | NP_002017 |
| fibrillin-1 | 2200 | NP_000129 |
| fibrillin-2 | 2201 | NP_001990 |
| collagen alpha2(IV) | 1284 | NP_001837 |
| collagen alpha2(V) | 1290 | NP_000384 |
| LOXL1 | 4016 | NP_005567 |
| nidogen | 4811 | NP_002499 |
| C11orf9 | 745 | NP_037411 |
| tenascin | 3371 | NP_002151 |
| N-cadherin | 1000 | NP_001783 |

[1]The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2]The NCBI RefSeq (Reference Sequence) is an example of a sequence expressed by the biomarker gene.

Table 1 lists the genes coding for examples of epithelial or mesenchymal molecular biomarkers that can be used in the practice of the methods of the invention described herein. The epithelial or mesenchymal molecular biomarkers can include any product expressed by these genes, including variants thereof, e.g. expressed mRNA or protein, splice variants, co- and post-translationally modified proteins, polymorphic variants etc. In one embodiment the biomarker is the embryonal EDB+ fibronectin, a splice variant expressed by the fibronectin 1 gene (Kilian, O. et al. (2004) Bone 35(6): 1334-1345). A possible advantage of determining this fetal form of fibronectin is that one could readily distinguish mesenchymal-like tumors from surrounding stromal tissue. In an additional embodiment the biomarker can be an animal homologue of the human gene product (e.g. from dog, mouse, rat, rabbit, cat, monkey, ape, etc.).

In another embodiment of any of the methods of the invention described herein, the mesenchymal biomarker utilized in the method is selected from the human transcriptional repressors Snail (a.k.a. SNAI1 (Official HUGO Gene Nomenclature Committee Symbol), snail homolog 1 (Drosophila) (Official HUGO Gene Nomenclature Committee Full Name); NCBI GeneID 6615), Zeb1 (NCBI GeneID 6935), Twist (NCBI GeneID 7291), Sip1 NCBI GeneID 8487), and Slug (NCBI GeneID 6591). In an additional embodiment the transcriptional repressor biomarker can be an animal homologue of the human gene product (e.g. from dog, mouse, rat, rabbit, cat, monkey, ape, etc.).

The present invention therefore provides a method of predicting the sensitivity of tumor cell growth to inhibition by an IGF-1R kinase inhibitor, comprising: assessing the level of a mesenchymal biomarker expressed by a tumor cell; and predicting the sensitivity of tumor cell growth to inhibition by an IGF-1R kinase inhibitor, wherein high levels of mesenchymal biomarker expression by tumor cells correlates with low sensitivity to inhibition by IGF-1R kinase inhibitors, and wherein the mesenchymal biomarker is selected from Snail, Zeb1, Twist, Sip1, and Slug. In one embodiment of this method, the tumor cell is a NSCL, colon, breast, head and neck, or pancreatic tumor cell.

The present invention also provides a method of predicting the sensitivity of tumor cell growth to inhibition by an IGF-1R kinase inhibitor, comprising: assessing the level of two or more mesenchymal biomarkers expressed by a tumor cell; and predicting the sensitivity of tumor cell growth to inhibition by an IGF-1R kinase inhibitor, wherein high levels of expression of any one of the mesenchymal biomarkers by the tumor cell correlates with low sensitivity to inhibition by IGF-1R kinase inhibitors, and wherein the two or more mesenchymal biomarkers are selected from Snail, Zeb1, Twist, Sip1, and Slug. In one embodiment of this method, the tumor cell is a NSCL, colon, breast, head and neck, or pancreatic tumor cell. In this method expression of only one of Snail, Zeb1, Twist, Sip1, and Slug can indicate transition to a mesenchymal cell type and low sensitivity to inhibition by IGF-1R kinase inhibitors due to the ability of the proteins expressed by these genes to complement each other in their ability to act as transcriptional repressors (e.g. of the E-cadherin gene).

The present invention also provides a method of predicting the sensitivity of tumor cell growth to inhibition by an IGF-1R kinase inhibitor, comprising: assessing the level of one or more mesenchymal biomarkers expressed by a tumor cell; and predicting the sensitivity of tumor cell growth to inhibition by an IGF-1R kinase inhibitor, wherein simultaneous low or undetectable expression levels of all of the assessed tumor cell mesenchymal biomarkers correlates with high sensitivity to inhibition by IGF-1R kinase inhibitors, and wherein at least one of the mesenchymal biomarkers is selected from Snail, Zeb1, Twist, Sip1, and Slug. In one embodiment the "one or more mesenchymal biomarkers" comprises vimentin and a mesenchymal biomarker selected from Snail, Zeb1, Twist, Sip1, and Slug. In another embodiment the "one or more mesenchymal biomarkers" comprises fibronectin and a mesenchymal biomarker selected from Snail, Zeb1, Twist, Sip1, and Slug. In another embodiment of this method, the tumor cell is a NSCL, colon, breast, head and neck, or pancreatic tumor cell.

In an embodiment of any of the methods of the invention described herein where the biomarker Snail, Zeb1, Twist, Sip1, or Slug is determined, the level of Snail, Zeb1, Twist, Sip1, or Slug mRNA transcript level is determined in order to assess the level of the Snail, Zeb1, Twist, Sip1, or Slug biomarker.

The present invention also provides a method of predicting the sensitivity of tumor cell growth to inhibition by an IGF-1R kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an IGF-1R kinase inhibitor, wherein a high ratio of epithelial to mesenchymal biomarker expression levels correlates with high sensitivity to inhibition by IGF-1R kinase inhibitors, and wherein the mesenchymal biomarker is selected from Snail, Zeb1, Twist, Sip1, and Slug. In one embodiment of this method the epithelial biomarker comprises E-cadherin. In another embodiment of this method the epithelial biomarker comprises Brk. In another embodiment of this method the epithelial biomarker comprises γ-catenin. In another embodiment of this method, the tumor cell is a NSCL, colon, breast, head and neck, or pancreatic tumor cell.

The present invention also provides a method for treating tumors or tumor metastases in a patient, comprising the steps of: diagnosing a patient's likely responsiveness to an IGF-1R kinase inhibitor by assessing whether the tumor cells have undergone an epithelial-mesenchymal transition: and administering to said patient a therapeutically effective amount of an IGF-1R kinase inhibitor if the patient is diagnosed to be potentially responsive to an IGF-1R kinase inhibitor, wherein the step of diagnosing a patient's likely responsiveness to an IGF-1R kinase inhibitor by assessing whether the tumor cells have undergone an epithelial-mesenchymal transition is performed by utilizing a method for predicting the sensitivity of tumor cell growth to inhibition by an IGF-1R kinase inhibitor that comprises assessing the level of one or more mesenchymal biomarkers selected from Snail, Zeb1, Twist, Sip1, and Slug. In one embodiment of this method, the "method for predicting the sensitivity of tumor cell growth to inhibition by an IGF-1R kinase inhibitor" is selected from any of the methods for predicting the sensitivity of tumor cell growth to inhibition by an IGF-1R kinase inhibitor that comprises assessing the level of one or more mesenchymal biomarker selected from Snail, Zeb1, Twist, Sip1, and Slug, as described herein. In another embodiment of this method, one or more additional anti-cancer agents are co-administered simultaneously or sequentially with the IGF-1R kinase inhibitor. In another embodiment of this method, the tumor cells are NSCL, colon, breast, head and neck, or pancreatic tumor cells.

The present invention also provides a method of predicting the sensitivity of tumor cell growth to inhibition by an IGF-1R kinase inhibitor, comprising: assessing the level of a mesenchymal biomarker expressed by a tumor cell, and predicting the sensitivity of tumor cell growth to inhibition by an IGF-1R kinase inhibitor, wherein high levels of tumor cell mesenchymal biomarkers correlate with low sensitivity to inhibition by IGF-1R kinase inhibitors, and wherein the mesenchymal biomarker is methylation of the promoter of a gene whose transcription is repressed as a result of EMT in the tumor cell. In the context of this method high levels of a tumor cell mesenchymal biomarker essentially means readily detectable methylation of the promoter (e.g. a strong signal during detection of a methylation-specific PCR-amplified nucleic acid product derived from a promoter methylation site), whereas low levels of a tumor cell mesenchymal biomarker essentially means no detectable or low methylation of the promoter (e.g. no, or a comparatively weak, signal during detection of a methylation-specific PCR-amplified nucleic acid product derived from a promoter methylation site). In one embodiment of this method the gene whose transcription is repressed as a result of EMT in the tumor cell is the E-Cadherin gene (i.e. CDH1; NCBI GeneID 999). In another embodiment of this method the gene whose transcription is repressed as a result of EMT in the tumor cell is the γ-catenin gene (i.e. NCBI GeneID 3728). In another embodiment of this method the gene whose transcription is repressed as a result of EMT in the tumor cell is an α-catenin gene (e.g. NCBI GeneID 1495, 1496, or 29119). In another embodiment of this method the gene whose transcription is repressed as a result of EMT in the tumor cell is a cytokeratin gene (e.g. NCBI GeneID 3856 (keratin 8) or 3875 (keratin 18)). In another embodiment of this method, the tumor cell is a NSCL, colon, breast, head and neck, or pancreatic tumor cell.

The present invention also provides a method for treating tumors or tumor metastases in a patient, comprising the steps of: diagnosing a patient's likely responsiveness to an IGF-1R kinase inhibitor by assessing whether the tumor cells have undergone an epithelial-mesenchymal transition: and administering to said patient a therapeutically effective amount of an IGF-1R kinase inhibitor, wherein the step of diagnosing a patient's likely responsiveness to an IGF-1R kinase inhibitor by assessing whether the tumor cells have undergone an epithelial-mesenchymal transition is performed by assessing the level of a mesenchymal biomarker expressed by a tumor cell, and predicting the sensitivity of tumor cell growth to inhibition by an IGF-1R kinase inhibitor, wherein high levels of tumor cell mesenchymal biomarkers correlate with low sensitivity to inhibition by IGF-1R kinase inhibitors, and wherein the mesenchymal biomarker is methylation of the promoter of a gene whose transcription is repressed as a result of EMT in the tumor cell. In one embodiment of this method the gene whose transcription is repressed as a result of EMT in the tumor cell is the E-Cadherin gene (i.e. CDH1). In another embodiment of this method, one or more additional anti-cancer agents are co-administered simultaneously or sequentially with the IGF-1R kinase inhibitor. In another embodiment of this method, the tumor cells are NSCL, colon, breast, head and neck, or pancreatic tumor cells.

The present invention also provides for any of the methods of treatment with an IGF-1R kinase inhibitor described herein, the method as described but including prior to the step of administering to the patient an IGF-1R kinase inhibitor, an additional step of assessment of the level of IGF-1 and/or IGF-2 (i.e. insulin-like growth factors 1 and/or 2) in the tumor of the patient. Since IGF-1R has been reported to be activated only upon ligand (i.e. IGF-1 and/or IGF-2) binding, if there is no IGF-1R ligand present in a tumor, then even if one or more of the methods of the instant invention predict that it should be sensitive to inhibition by IGF-1R kinase inhibitors, the tumor cells cannot under such circumstances be relying on the IGF-1R signaling pathway for growth and survival, and thus an IGF-1R kinase inhibitor would probably not be an effective treatment. Many tumors have been found to express elevated levels of IGF-1 and/or IGF-2 (Pollack, M. N. et al. (2004) Nature Reviews Cancer 4:505-518), which could originate from the tumor cells themselves, from stromal cells present in the tumor, or via the vascular system from non-tumor cells (e.g. liver cells). Assessment of the level of IGF-1 and/or IGF-2 can be performed by any method known in the art, such as for example any of the methods described herein for assessment of biomarkers levels, e.g. immunoassay determination of IGF-1 and/or IGF-2 protein levels; determination of IGF-1 and/or IGF-2 mRNA transcript levels. In an alternative embodiment, the of step of assessment of the level of IGF-1 and/or IGF-2 (i.e. insulin-like growth factors 1 and/or 2) in the tumor of the patient can be replaced with a step of assessment of the level of IGF-1 and/or IGF-2 (i.e. insulin-like growth factors 1 and/or 2) in the blood or serum of the patient. This alternative, though not a direct measure of the level of IGF-1 and/or IGF-2 in the tumor, can give an indication of the potential availability of ligand to the IGF-1R in the tumor, and is a simpler and less expensive test. The potential disadvantage of this indirect assessment of IGF-1 and/or IGF-2 is that it may not give a true indication of the levels of ligand in the tumor if IGF-1 and/or IGF-2 is produced locally in the tumor, either by the tumor cells themselves, or by stromal cells within the tumor.

Accordingly, the invention provides a method for treating tumors or tumor metastases in a patient, comprising the steps of: diagnosing a patient's likely responsiveness to an IGF-1R kinase inhibitor, by assessing whether the tumor cells have undergone an epithelial-mesenchymal transition (EMT), by for example assessing an epithelial and/or mesenchymal biomarker expressed by a tumor cell, wherein high expression levels of an epithelial biomarker correlates with high sensitivity to inhibition by IGF-1R kinase inhibitors, and wherein a high expression levels of an mesenchymal biomarker correlates with low sensitivity to inhibition by IGF-1R kinase inhibitors; assessing the level of IGF-1 and/or IGF-2 in the tumor (or blood or serum) of the patient; and administering to said patient a therapeutically effective amount of an IGF-1R kinase inhibitor if the patient is diagnosed to be potentially responsive to an IGF-1R kinase inhibitor, and the tumor is determined to have IGF-1 and/or IGF-2 (or blood or serum levels indicate the potential availability of IGF-1 and/or IGF-2 to the tumor cells). In an additional embodiment, the step of diagnosing a patient's likely responsiveness to an IGF-1R kinase inhibitor by assessing whether the tumor cells have undergone an epithelial-mesenchymal transition, can be replaced by a step of assessing one or more other biomarkers as described herein for assessing sensitivity to IGF-1R kinase inhibitors, e.g. pErk, HER3, pHER3. Alternatively, assessment of these one or more other biomarkers for assessing sensitivity to IGF-1R kinase inhibitors can be performed in addition to the assessment of whether the tumor cells have undergone an epithelial-mesenchymal transition. In methods where more than one biomarker is assessed for predicting sensitivity to IGF-1R kinase inhibitors, the patient is diagnosed to be potentially responsive to an IGF-1R kinase inhibitor if at least one of the methods indicates potential sensitivity.

The present invention also provides a method for treating tumors or tumor metastases in a patient, comprising the steps of: diagnosing a patient's likely responsiveness to an IGF-1R kinase inhibitor, by assessing the level of a biomarker indicative of whether the tumor cells have undergone an epithelial-mesenchymal transition (EMT); assessing the level of IGF-1 and/or IGF-2 in the tumor of the patient; and administering to said patient a therapeutically effective amount of an IGF-1R kinase inhibitor if the patient is diagnosed to be potentially responsive to an IGF-1R kinase inhibitor, and the tumor is determined to have IGF-1 and/or IGF-2.

The present invention also provides a method for treating tumors or tumor metastases in a patient, comprising the steps of: diagnosing a patient's likely responsiveness to an IGF-1R kinase inhibitor, by assessing the level of a biomarker selected from pErk, HER3, and pHER3; assessing the level of IGF-1 and/or IGF-2 in the tumor of the patient; and administering to said patient a therapeutically effective amount of an IGF-1R kinase inhibitor if the patient is diagnosed to be potentially responsive to an IGF-1R kinase inhibitor, and the tumor is determined to have IGF-1 and/or IGF-2.

The present invention also provides a method of predicting whether a cancer patient is afflicted with a tumor that will respond effectively to treatment with an IGF-1R kinase inhibitor, comprising: assessing the level of an epithelial biomarker expressed by cells of the tumor; and predicting if the tumor will respond effectively to treatment with an IGF-1R kinase inhibitor, wherein high expression levels of tumor cell epithelial biomarkers correlate with a tumor that will respond effectively to treatment with an IGF-1R kinase inhibitor, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, and phospho-SHC1. Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein. In one embodiment of this method the IGF-1R kinase inhibitor comprises OSI-906.

The present invention also provides a method of predicting whether a cancer patient is afflicted with a tumor that will respond effectively to treatment with an IGF-1R kinase inhibitor, comprising: assessing the level of a mesenchymal biomarker expressed by cells of the tumor; and predicting if the tumor will respond effectively to treatment with an IGF-1R kinase inhibitor, wherein high expression levels of tumor cell mesenchymal biomarkers correlate with a tumor that will respond less effectively to treatment with an IGF-1R kinase inhibitor, wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, and SHC1. Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein. In one embodiment of this method the IGF-1R kinase inhibitor comprises OSI-906.

The present invention also provides a method of predicting the sensitivity of tumor cell growth to inhibition by an IGF-1R kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an IGF-1R kinase inhibitor, wherein a high ratio of epithelial to mesenchymal biomarker expression levels correlates with high sensitivity to inhibition by IGF-1R kinase inhibitors, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5 and ST14, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, and SHC1, or alternatively, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc (CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, and phospho-SHC1, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine—tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, vimentin, fibronectin, fibrillin-1, fibrillin-2, collagen alpha-2(IV), collagen alpha-2 (V), LOXL1, nidogen, C11orf9, tenascin, N-cadherin, embryonal EDB+ fibronectin, tubulin alpha-3 and epimorphin. In one embodiment of this method the IGF-1R kinase inhibitor comprises OSI-906.

Examples of additional epithelial markers that can be used in any of the methods of this invention include phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5 and ST14 (see Table 1 and FIG. 7). Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

Examples of additional mesenchymal markers that can be used in any of the methods of this invention include MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, vimentin, fibronectin, fibrillin-1, fibrillin-1, fibrillin-2, collagen alpha-2 (IV), collagen alpha-2(V), LOXL1, nidogen, C11orf9, tenascin, N-cadherin, embryonal EDB⁺ fibronectin, tubulin alpha-3 and epimorphin (see Table 1 and FIG. 7). Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

Additional epithelial biomarkers that can be used in any of the methods of the invention, but which appear to be restricted to use in a subset of tumor cell types (e.g. H1703 cells), include SERCA2, CD44 antigen, ERO1-L alpha, Serine hydroxymethyltransferase, phospho-GPCR RAIG-3, Dihydrolipoyllysine succinyltransferase, Peroxiredoxin 2, Reticulocalbin-1, phospho-40S ribosomal protein S15 (RIG protein), and Tumor protein D54. Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

The present invention also provides a method of predicting whether a cancer patient is afflicted with a tumor that will respond effectively to treatment with an IGF-1R kinase inhibitor, comprising: assessing the level of an epithelial biomarker expressed by cells of the tumor; and predicting if the tumor will respond effectively to treatment with an IGF-1R kinase inhibitor, wherein high expression levels of tumor cell epithelial biomarkers correlate with a tumor that will respond effectively to treatment with an IGF-1R kinase inhibitor, wherein the epithelial biomarker is selected from SERCA2, CD44 antigen, ERO1-L alpha, Serine hydroxymethyltransferase, phospho-GPCR RAIG-3, Dihydrolipoyllysine succinyltransferase, Peroxiredoxin 2, Reticulocalbin-1, phospho-40S ribosomal protein S15 (RIG protein), and Tumor protein D54.

Additional mesenchymal biomarkers that can be used in any of the methods of the invention, but which appear to be restricted to use in a subset of tumor cell types (e.g. H1703 cells), include phospho-Alpha-internexin, Retinal dehydrogenase 1, Fatty aldehyde dehydrogenase, Asparagine synthetase, Brain acid soluble protein 1, phospho-Caveolin-1, phospho-ARF, GTPase-activating protein, Mago nashi protein homolog 2, phospho-ERK-2, phospho-p38alpha, Nucleoside diphosphate kinase B, NAD(P)H dehydrogenase, phospho-PDGF-R-alpha, phospho-Progesterone-induced blocking factor 1, Pirin, Profilin-1, phospho-Tyrosine-protein phosphatase SHP-2, phospho-TAF(II)68, STAT3, Asparaginyl-tRNA synthetase, Thioredoxin reductase 1, UDP-N-acetylhexosamine pyrophosphorylase, Ubiquitin carboxyl-terminal hydrolase, and Zyxin. Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

The present invention also provides a method of predicting whether a cancer patient is afflicted with a tumor that will respond effectively to treatment with an IGF-1R kinase inhibitor, comprising: assessing the level of a mesenchymal biomarker expressed by cells of the tumor; and predicting if the tumor will respond effectively to treatment with an IGF-1R kinase inhibitor, wherein high expression levels of tumor cell mesenchymal biomarkers correlate with a tumor that will respond less effectively to treatment with an IGF-1R kinase inhibitor, wherein the mesenchymal biomarker is selected from phospho-Alpha-internexin, Retinal dehydrogenase 1, Fatty aldehyde dehydrogenase, Asparagine synthetase, Brain acid soluble protein 1, phospho-Caveolin-1, phospho-ARF, GTPase-activating protein, Mago nashi protein homolog 2, phospho-ERK-2, phospho-p38alpha, Nucleoside diphosphate kinase B, NAD(P)H dehydrogenase, phospho-PDGF-R-alpha, phospho-Progesterone-induced blocking factor 1, Pirin, Profilin-1, phospho-Tyrosine-protein phosphatase SHP-2, phospho-TAF(II)68, STAT3, Asparaginyl-tRNA synthetase, Thioredoxin reductase 1, UDP-N-acetylhexosamine pyrophosphorylase, Ubiquitin carboxyl-terminal hydrolase, and Zyxin.

Further additional epithelial biomarkers that can be used in any of the methods of the invention, but which appear to be restricted to use in different subset of tumor cell types (e.g. Calu6 cells), include 14-3-3 beta/alpha, phospho-Rho GEF-7 (p85COOL-1), Brain acid soluble protein 1, phospho-Caveolin-1, Filamin A, phospho-p38alpha, Nucleoside diphosphate kinase B, phospho-Paxillin, phospho-Tyrosine-protein phosphatase SHP-2, C-ret, STAT3, Asparaginyl-tRNA synthetase, and Ubiquitin carboxyl-terminal hydrolase. Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

The present invention also provides a method of predicting whether a cancer patient is afflicted with a tumor that will respond effectively to treatment with an IGF-1R kinase inhibitor, comprising: assessing the level of an epithelial biomarker expressed by cells of the tumor; and predicting if the tumor will respond effectively to treatment with an IGF-1R kinase inhibitor, wherein high expression levels of tumor cell epithelial biomarkers correlate with a tumor that will respond effectively to treatment with an IGF-1R kinase inhibitor, wherein the epithelial biomarker is selected from 14-3-3 beta/alpha, phospho-Rho GEF-7 (p85COOL-1), Brain acid soluble protein 1, phospho-Caveolin-1, Filamin A, phospho-p38alpha, Nucleoside diphosphate kinase B, phospho-Paxillin, phospho-Tyrosine-protein phosphatase SHP-2, C-ret, STAT3, Asparaginyl-tRNA synthetase, and Ubiquitin carboxyl-terminal hydrolase.

Further additional mesenchymal biomarkers that can be used in any of the methods of the invention, but which appear to be restricted to use in a different subset of tumor cell types (e.g. Calu6 cells), include Acidic leucine-rich nuclear phosphoprotein 32B, CD44 antigen, Calcium-binding Aralar2, 2,4-dienoyl-CoA reductase, Electron transfer flavoprotein, Fatty acid-binding protein (E-FABP), RNA-binding protein FUS, K-glutaminase, mitochondrial creatine kinase, phospho-Leupaxin, Myristoylated alanine-rich C-kinase substrate, Ras-related protein Rab-2A, Ras-related protein Rab-7, Ras-related protein Rap-1b, phospho-C-ret, and STAT3. Where the mesenchymal biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein.

The present invention also provides a method of predicting whether a cancer patient is afflicted with a tumor that will respond effectively to treatment with an IGF-1R kinase inhibitor, comprising: assessing the level of a mesenchymal biomarker expressed by cells of the tumor; and predicting if the tumor will respond effectively to treatment with an IGF-1R kinase inhibitor, wherein high expression levels of tumor cell mesenchymal biomarkers correlate with a tumor that will respond less effectively to treatment with an IGF-1R kinase inhibitor, wherein the mesenchymal biomarker is selected from Acidic leucine-rich nuclear phosphoprotein 32B, CD44 antigen, Calcium-binding Aralar2, 2,4-dienoyl-CoA reductase, Electron transfer flavoprotein, Fatty acid-binding protein (E-FABP), RNA-binding protein FUS, K-glutaminase, mitochondrial creatine kinase, phospho-Leupaxin, Myristoylated alanine-rich C-kinase substrate, Ras-related protein Rab-2A, Ras-related protein Rab-7, Ras-related protein Rap-1b, phospho-C-ret, and STAT3.

The present invention also provides a method of predicting the sensitivity of tumor cell growth to inhibition by an IGF-1R kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an IGF-1R kinase inhibitor, wherein a high ratio of epithelial to mesenchymal biomarker expression levels correlates with high sensitivity to inhibition by IGF-1R kinase inhibitors, wherein the epithelial biomarker is selected from phospho- 14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5, ST14, SERCA2, CD44 antigen, ERO1-L alpha, Serine hydroxymethyltransferase, phospho-GPCR RAIG-3, Dihydrolipoyllysine succinyltransferase, Peroxiredoxin 2, Reticulocalbin-1, phospho-40S ribosomal protein S15 (RIG protein), and Tumor protein D54, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrilarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, phospho-Alpha-internexin, Retinal dehydrogenase 1, Fatty aldehyde dehydrogenase, Asparagine synthetase, Brain acid soluble protein 1, phospho-Caveolin-1, phospho-ARF, GTPase-activating protein, Mago nashi protein homolog 2, phospho-ERK-2, phospho-p38alpha, Nucleoside diphosphate kinase B, NAD(P)H dehydrogenase, phospho-PDGF-R-alpha, phospho-Progesterone-induced blocking factor 1, Pirin, Profilin-1, phospho-Tyrosine-protein phosphatase SHP-2, phospho-TAF(II)68, STAT3, Asparaginyl-tRNA synthetase, Thioredoxin reductase 1, UDP-N-acetylhexosamine pyrophosphorylase, Ubiquitin carboxyl-terminal hydrolase, and Zyxin, or alternatively, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, SERCA2, CD44 antigen, ERO1-L alpha, Serine hydroxymethyltransferase, phospho-GPCR RAIG-3, Dihydrolipoyllysine succinyltransferase, Peroxiredoxin 2, Reticulocalbin-1, phospho-40S ribosomal protein S15 (RIG protein), and Tumor protein D54, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine—tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, vimentin, fibronectin, fibrillin-1, fibrillin-2, collagen alpha-2 (IV), collagen alpha-2(V), LOXL1, nidogen, C11orf9, tenascin, N-cadherin, embryonal EDB$^+$ fibronectin, tubulin alpha-3, epimorphin, phospho-Alpha-internexin, Retinal dehydrogenase 1, Fatty aldehyde dehydrogenase, Asparagine synthetase, Brain acid soluble protein 1, phospho-Caveolin-1, phospho-ARF, GTPase-activating protein, Mago nashi protein homolog 2, phospho-ERK-2, phospho-p38alpha, Nucleoside diphosphate kinase B, NAD(P)H dehydrogenase, phospho-PDGF-R-alpha, phospho-Progesterone-induced blocking factor 1, Pirin, Profilin-1, phospho-Tyrosine-protein phosphatase SHP-2, phospho-TAF(II)68, STAT3, Asparaginyl-tRNA synthetase, Thioredoxin reductase 1, UDP-N-acetylhexosamine pyrophosphorylase, Ubiquitin carboxyl-terminal hydrolase, and Zyxin. In one embodiment of this method the IGF-1R kinase inhibitor comprises OSI-906.

The present invention also provides a method of predicting the sensitivity of tumor cell growth to inhibition by an IGF-1R kinase inhibitor, comprising: assessing the level of an epithelial biomarker expressed by a tumor cell; assessing the level of a mesenchymal biomarker expressed by a tumor cell; and predicting the sensitivity of tumor cell growth to inhibition by an IGF-1R kinase inhibitor, wherein a high ratio of epithelial to mesenchymal biomarker expression levels correlates with high sensitivity to inhibition by IGF-1R kinase inhibitors, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5, ST14, 14-3-3 beta/alpha, phospho-Rho GEF-7 (p85COOL-1), Brain acid soluble protein 1, phospho-Caveolin-1, Filamin A, phospho-p38alpha, Nucleoside diphosphate kinase B, phospho-Paxillin, phospho-Tyrosine-protein phosphatase SHP-2, C-ret, STAT3, Asparaginyl-tRNA synthetase, and Ubiquitin carboxyl-terminal hydrolase, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyl-transferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, Acidic leucine-rich nuclear phosphoprotein 32B, CD44 antigen, Calcium-binding Aralar2, 2,4-dienoyl-CoA reductase, Electron transfer flavoprotein, Fatty acid-binding protein (E-FABP), RNA-binding protein FUS, K-glutaminase, mitochondrial creatine kinase, phospho-Leupaxin, Myristoylated alanine-rich C-kinase substrate, Ras-related protein Rab-2A, Ras-related protein Rab-7, Ras-related protein Rap-1b, phospho-C-ret, and STAT3, or alternatively, wherein the epithelial biomarker is selected from phospho-14-3-3 epsilon, 14-3-3 gamma (KCIP-1), 14-3-3 sigma (Stratifin), 14-3-3 zeta/delta, phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER), Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2, phospho-Erbin, LIM and SH3 domain protein 1 (LASP-1), 4F2lc (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, Lysosome membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, 14-3-3 beta/alpha, phospho-Rho GEF-7 (p85COOL-1), Brain acid soluble protein 1, phospho-Caveolin-1, Filamin A, phospho-p38alpha, Nucleoside diphosphate kinase B, phospho-Paxillin, phospho-Tyrosine-protein phosphatase SHP-2, C-ret, STAT3, Asparaginyl-tRNA synthetase, and Ubiquitin carboxyl-terminal hydrolase, and wherein the mesenchymal biomarker is selected from MHC class I antigen A*1, Acyl-CoA desaturase, LANP-like protein (LANP-L), Annexin A6, ATP synthase gamma chain, BAG-family molecular chaperone regulator-2, phospho-Bullous pemphigoid antigen, phospho-Protein C1orf77, CDK1 (cdc2), phospho-Clathrin heavy chain 1, Condensin complex subunit 1, 3,2-trans-enoyl-CoA isomerase, DEAH-box protein 9, phospho-Enhancer of rudimentary homolog, phospho-Fibrillarin, GAPDH muscle, GAPDH liver, Synaptic glycoprotein SC2, phospho-Histone H1.0, phospho-Histone H1.2, phospho-Histone H1.3, phospho-Histone H1.4, phospho-Histone H1.5, phospho-Histone H1x, phospho-Histone H2AFX, phospho-Histone H2A.o, phospho-Histone H2A.q, phospho-Histone H2A.z, phospho-Histone H2B.j, phospho-Histone H2B.r, phospho-Histone H4, phospho-HMG-17-like 3, phospho-HMG-14, phospho-HMG-17, phospho-HMGI-C, phospho-HMG-I/HMG-Y, phospho-Thyroid receptor interacting protein 7 (TRIP7), phospho-hnRNP H3, hnRNP C1/C2, hnRNP F, phospho-hnRNP G, eIF-5A, NFAT 45 kDa, Importin beta-3, cAMP-dependent Pk1a, Lamin B1, Lamin A/C, phospho-Laminin alpha-3 chain, L-lactate dehydrogenase B chain, Galectin-1, phospho-Fez1, Hyaluronan-binding protein 1, phospho-Microtubule-actin crosslinking factor 1, Melanoma-associated antigen 4, Matrin-3, Phosphate carrier protein, Myosin-10, phospho-N-acylneuraminate cytidylyltransferase, phospho-NHP2-like protein 1, H/ACA ribonucleoprotein subunit 1, Nucleolar phosphoprotein p130, phospho-RNA-binding protein Nova-2, Nucleophosmin (NPM), NADH-ubiquinone oxidoreductase 39 kDa subunit, phospho-Polyadenylate-binding protein 2, Prohibitin, Prohibitin-2, Splicing factor Prp8, Polypyrimidine tract-binding protein 1, Parathymosin, Rab-2A, phospho-RNA-binding protein Raly, Putative RNA-binding protein 3, phospho-60S ribosomal protein L23, hnRNP A0, hnRNP A2/B1, hnRNP A/B, U2 small nuclear ribonucleoprotein B, phospho-Ryanodine receptor 3, phospho-Splicing factor 3A subunit 2, snRNP core protein D3, Nesprin-1, Tyrosine-tRNA ligase, phospho-Tankyrase 1-BP, Tubulin beta-3, Acetyl-CoA acetyltransferase, phospho-bZIP enhancing factor BEF (Aly/REF; Tho4), Ubiquitin, Ubiquitin carboxyl-terminal hydrolase 5, Ubiquinol-cytochrome c reductase, Vacuolar protein sorting 16, phospho-Zinc finger protein 64, phospho-AHNAK (Desmoyokin), ATP synthase beta chain, ATP synthase delta chain, phospho-Cold shock domain protein E1, phospho-Plectin 1, Nectin 2 (CD112 antigen), p185-Ron, SHC1, vimentin, fibronectin, fibrillin-1, fibrillin-2, collagen alpha-2(IV), collagen alpha-2(V), LOXL1, nidogen, C11orf9, tenascin, N-cadherin, embryonal EDB+ fibronectin, tubulin alpha-3, epimorphin, Acidic leucine-rich nuclear phosphoprotein 32B, CD44 antigen, Calcium-binding Aralar2, 2,4-dienoyl-CoA reductase, Electron transfer flavoprotein, Fatty acid-binding protein (E-FABP), RNA-binding protein FUS, K-glutaminase, mitochondrial creatine kinase, phospho-Leupaxin, Myristoylated alanine-rich C-kinase substrate, Ras-related protein Rab-2A, Ras-related protein Rab-7, Ras-related protein Rap-1b, phospho-C-ret, and STAT3. In one embodiment of this method the IGF-1R kinase inhibitor comprises OSI-906.

The present invention also provides a method for treating tumors or tumor metastases in a patient, comprising the steps of diagnosing a patient's likely responsiveness to an IGF-1R kinase inhibitor by using any of the methods described herein to predict the sensitivity of tumor cell growth to inhibition by an IGF-1R kinase inhibitor, identifying the patient as one who is likely to demonstrate an effective response to treatment with an IGF-1R kinase inhibitor, and administering to said patient a therapeutically effective amount of an IGF-1R kinase inhibitor. In one embodiment the IGF-1R kinase inhibitor comprises OSI-906.

The present invention also provides a method of predicting the sensitivity of tumor cell growth to inhibition by an IGF-1R kinase inhibitor, comprising: assessing the level of the biomarker pErk expressed by a tumor cell; and predicting the sensitivity of tumor cell growth to inhibition by an IGF-1R kinase inhibitor, wherein high levels of biomarker pErk expression by tumor cells correlates with low sensitivity to inhibition by IGF-1R kinase inhibitors. In one embodiment of this method the tumor cell is a NSCL, colon, breast, ovarian, head and neck, or pancreatic tumor cell.

The present invention also provides a method for treating tumors or tumor metastases in a patient, comprising the steps of: diagnosing a patient's likely responsiveness to an IGF-1R kinase inhibitor by assessing the level of the biomarker pErk expressed by the tumor cells of the patient, wherein high levels of biomarker pErk expression by tumor cells correlates with low sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor. In one embodiment of this method, one or more additional anti-cancer agents are co-administered simultaneously or sequentially with the IGF-1R kinase inhibitor. In another embodiment of this method the tumor cells are NSCL, colon, breast, ovarian, head and neck, or pancreatic tumor cells. In an alternative embodiment of this method, the additional step of diagnosing a patient's likely responsiveness to an IGF-1R kinase inhibitor by assessing whether the tumor cells have undergone an epithelial-mesenchymal transition is performed, wherein the step of diagnosing a patient's likely responsiveness to an IGF-1R kinase inhibitor by assessing whether the tumor cells have undergone an epithelial-mesenchymal transition is performed by assessing the level of one or more biomarkers using any of the methods described herein. This alternative dual biomarker embodiment where pErk and a biomarker indicating EMT status are both assessed prior to treatment provides a method with increased potential reliability. In this embodiment if either one or both of the steps for diagnosing a patient's likely responsiveness to an IGF-1R kinase inhibitor indicated that the patient would likely be responsive to an IGF-1R kinase inhibitor, the patient would be diagnosed to be potentially responsive to an IGF-1R kinase inhibitor, and thus administered a therapeutically effective amount of an IGF-1R kinase inhibitor.

Accordingly, this invention provides a method for treating tumors or tumor metastases in a patient, comprising the steps of: diagnosing a patient's likely responsiveness to an IGF-1R kinase inhibitor, by both assessing the level of the biomarker pErk expressed by the tumor cells of the patient, wherein low levels of the biomarker pErk expression by tumor cells correlates with high sensitivity to inhibition by IGF-1R kinase inhibitors; and assessing whether the tumor cells have undergone an epithelial-mesenchymal transition, by assessing an epithelial or mesenchymal biomarker expressed by a tumor cell, wherein high expression levels of an epithelial biomarker correlates with high sensitivity to inhibition by IGF-1R kinase inhibitors, and wherein a high expression levels of an mesenchymal biomarker correlates with low sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor by any of the biomarker assessments. The epithelial or mesenchymal biomarker assessed can be any of the epithelial or mesenchymal biomarkers disclosed herein.

One example of the dual biomarker embodiment described in the preceding paragraphs is: A method for treating tumors or tumor metastases in a patient, comprising the steps of: diagnosing a patient's likely responsiveness to an IGF-1R kinase inhibitor, by both assessing the level of the biomarker pErk expressed by the tumor cells of the patient, wherein low levels of the biomarker pErk expression by tumor cells correlates with high sensitivity to inhibition by IGF-1R kinase inhibitors; and assessing the level of E-cadherin expressed by a tumor cell, wherein a high expression levels of E-cadherin correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

Another example of the dual biomarker embodiment described above is: A method for treating tumors or tumor metastases in a patient, comprising the steps of: diagnosing a patient's likely responsiveness to an IGF-1R kinase inhibitor, by both assessing the level of the biomarker pErk expressed by the tumor cells of the patient, wherein low levels of the biomarker pErk expression by tumor cells correlates with high sensitivity to inhibition by IGF-1R kinase inhibitors; and assessing the methylation status of the E-cadherin gene promoter in the tumor cell, wherein lack of E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

In any of the methods of the invention described herein, where a biomarker utilized in the method is pErk, the term "pErk" refers to "phosphorylated Erk protein", wherein "Erk" is Erk1 and/or Erk2 (e.g. the proteins encoded by the human Erk1 and Erk2 genes with NCBI GeneID numbers of 5595 and 5594), each phosphorylated at both the tyrosine and threonine amino acid residues required for Erk kinase activation (i.e. T202 and Y204 in human Erk1; and T185 and Y187 in human Erk2; the amino acid residues immediately surrounding these phosphorylation sites are identical in human Erk1 and Erk 2). Double phosphorylation of Erk has been demonstrated to be required for activation of the kinase activity of the enzyme. In human tumor cell lysates analyzed by SDS-PAGE and immunoblots probed with pErk-specific antibodies, when Erk1 and Erk 2 are both present a p42/p44 phosphorylated Erk1/Erk2 doublet is typically observed. In embodiments of any of the inventions described herein where pErk is involved and wherein the tumor cells or patient is non-human, the Erk is the corresponding animal homolog(s) of Erk, and pErk is phosphorylated at an analogous pair of amino acid residues during activation of the enzyme (N.B. the numbering of the two phosphorylated residues may vary, depending on the species, but will be readily apparent to one of skill in the art by examination of the animal sequence homolous to the amino acid sequence around the human Erk 1 or Erk2 phosphorylation sites).

In the methods of this invention, the level of pErk biomarker expressed by a tumor cell can be assessed by using any of the standard bioassay procedures known in the art for determination of the level of expression of a phosphoprotein, including immunological methods for the determination of the level of phosphoproteins, including for example ELISA, RIA, immunoprecipitation, immunoblotting, immunofluorescence microscopy, or the like, as described in more detail herein, or for example protein purification methods, or protein function or activity assays. In a preferred embodiment, for assay of human pErk, an antibody produced from a hybridoma (e.g. an IgG fraction purified by protein G affinity chromatography) elicited from an animal immunized with a synthetic phosphopeptide corresponding to residues surrounding T202/Y204 in human Erk1 (which is identical to the T185/Y187 phosphorylation site of human Erk2) is used in an immunoassay.

In the methods of this invention, pErk biomarker expression level can be assessed relative to the expression of a control molecule whose expression level remains constant (e.g. a "housekeeping" gene, such as GAPDH, β-actin, tubulin, or the like). pErk biomarker expression level can also be assessed relative to the another type of tumor cell biomarker (i.e. epithelial, mesenchymal), or to the biomarker level in non-tumor cells of the same tissue, or another cell or tissue source used as an assay reference. For example, one of the cell lines described herein in the experimental section in which pErk level was determined and correlated with sensitivity of tumor cell growth to inhibition by an IGF-1R kinase inhibitor may be used as an assay reference.

The present invention also provides a method of predicting the sensitivity of tumor cell growth to inhibition by an IGF-1R kinase inhibitor, comprising: assessing the level of the biomarker HER3 expressed by a tumor cell; and predicting the sensitivity of tumor cell growth to inhibition by an IGF-1R kinase inhibitor, wherein high levels of biomarker HER3 expression by tumor cells correlates with high sensitivity to inhibition by IGF-1R kinase inhibitors. In one embodiment of this method the tumor cell is a NSCL, colon, breast, head and neck, or pancreatic tumor cell.

The present invention also provides a method for treating tumors or tumor metastases in a patient, comprising the steps of: diagnosing a patient's likely responsiveness to an IGF-1R kinase inhibitor by assessing the level of the biomarker HER3 expressed by the tumor cells of the patient, wherein high levels of biomarker HER3 expression by tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor. In one embodiment of this method, one or more additional anti-cancer agents are co-administered simultaneously or sequentially with the IGF-1R kinase inhibitor. In another embodiment of this method the tumor cells are NSCL, colon, breast, head and neck, or pancreatic tumor cells. In an alternative embodiment of this method, the additional step of diagnosing a patient's likely responsiveness to an IGF-1R kinase inhibitor by assessing whether the tumor cells have undergone an epithelial-mesenchymal transition is performed, wherein the step of diagnosing a patient's likely responsiveness to an IGF-1R kinase inhibitor by assessing whether the tumor cells have undergone an epithelial-mesenchymal transition is performed by assessing the level of one or more biomarkers using any of the methods described herein. This alternative dual biomarker embodiment where HER3 and a biomarker indicating EMT status are both assessed prior to treatment provides a method with increased potential reliability. In this embodiment if either one or both of the steps for diagnosing a patient's likely responsiveness to an IGF-1R kinase inhibitor indicated that the patient would likely be responsive to an IGF-1R kinase inhibitor, the patient would be diagnosed to be potentially responsive to an IGF-1R kinase inhibitor, and thus administered a therapeutically effective amount of an IGF-1R kinase inhibitor.

One example of the dual biomarker embodiment described in the preceding paragraph is: A method for treating tumors or tumor metastases in a patient, comprising the steps of: diagnosing a patient's likely responsiveness to an IGF-1R kinase inhibitor, by both assessing the level of the biomarker HER3 expressed by the tumor cells of the patient, wherein high levels of the biomarker HER3 expression by tumor cells correlates with high sensitivity to inhibition by IGF-1R kinase inhibitors; and assessing the level of E-cadherin expressed by a tumor cell, wherein a high expression levels of E-cadherin correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

Another example of the dual biomarker embodiment described above is: A method for treating tumors or tumor metastases in a patient, comprising the steps of: diagnosing a patient's likely responsiveness to an IGF-1R kinase inhibitor, by both assessing the level of the biomarker HER3 expressed by the tumor cells of the patient, wherein high levels of the biomarker HER3 expression by tumor cells correlates with high sensitivity to inhibition by IGF-1R kinase inhibitors; and assessing the methylation status of the E-cadherin gene promoter in the tumor cell, wherein lack of E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

In an embodiment of any of the methods of the invention described herein where the biomarker HER3 is determined, the level of HER3 mRNA transcript level is determined in order to assess the level of the biomarker HER3.

The present invention also provides a method of predicting the sensitivity of tumor cell growth to inhibition by an IGF-1R kinase inhibitor, comprising: assessing the level of the biomarker pHER3 expressed by a tumor cell; and predicting the sensitivity of tumor cell growth to inhibition by an IGF-1R kinase inhibitor, wherein high levels of the biomarker pHER3 in tumor cells correlates with high sensitivity to inhibition by IGF-1R kinase inhibitors. In one embodiment of this method the tumor cell is a NSCL, colon, breast, head and neck, or pancreatic tumor cell.

The present invention also provides a method for treating tumors or tumor metastases in a patient, comprising the steps of: diagnosing a patient's likely responsiveness to an IGF-1R kinase inhibitor by assessing the level of the biomarker pHER3 expressed by the tumor cells of the patient, wherein high levels of biomarker pHER expression by tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor. In one embodiment of this method, one or more additional anti-cancer agents are co-administered simultaneously or sequentially with the IGF-1R kinase inhibitor. In another embodiment of this method the tumor cells are NSCL, colon, breast, head and neck, or pancreatic tumor cells. In an alternative embodiment of this method, the additional step of diagnosing a patient's likely responsiveness to an IGF-1R kinase inhibitor by assessing whether the tumor cells have undergone an epithelial-mesenchymal transition is performed, wherein the step of diagnosing a patient's likely responsiveness to an IGF-1R kinase inhibitor by assessing whether the tumor cells have undergone an epithelial-mesenchymal transition is performed by assessing the level of one or more biomarkers using any of the methods described herein. This alternative dual biomarker embodiment where pHER3 and a biomarker indicating EMT status are both assessed prior to treatment provides a method with increased potential reliability. In this embodiment if either one or both of the steps for diagnosing a patient's likely responsiveness to an IGF-1R kinase inhibitor indicated that the patient would likely be responsive to an IGF-1R kinase inhibitor, the patient would be diagnosed to be potentially responsive to an IGF-1R kinase inhibitor, and thus administered a therapeutically effective amount of an IGF-1R kinase inhibitor.

Accordingly, one example of the dual biomarker embodiment described in the preceding paragraph is: A method for treating tumors or tumor metastases in a patient, comprising the steps of: diagnosing a patient's likely responsiveness to an IGF-1R kinase inhibitor, by both assessing the level of the biomarker pHER3 expressed by the tumor cells of the patient, wherein high levels of the biomarker pHER3 expression by tumor cells correlates with high sensitivity to inhibition by IGF-1R kinase inhibitors; and assessing the level of E-cadherin expressed by a tumor cell, wherein a high expression levels of E-cadherin correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

Another example of the dual biomarker embodiment described above is: A method for treating tumors or tumor metastases in a patient, comprising the steps of: diagnosing a patient's likely responsiveness to an IGF-1R kinase inhibitor, by both assessing the level of the biomarker pHER3 expressed by the tumor cells of the patient, wherein high levels of the biomarker pHER3 expression by tumor cells correlates with high sensitivity to inhibition by IGF-1R kinase inhibitors; and assessing the methylation status of the E-cadherin gene promoter in the tumor cell, wherein lack of E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

This invention further provides a method for treating tumors or tumor metastases in a patient, comprising the steps of: diagnosing a patient's likely responsiveness to an IGF-1R kinase inhibitor, by both assessing the level of the biomarker HER3 expressed by the tumor cells of the patient, wherein high levels of the biomarker HER3 expression by tumor cells correlates with high sensitivity to inhibition by IGF-1R kinase inhibitors; and assessing the level of the biomarker pErk expressed by the tumor cells of the patient, wherein low levels of the biomarker pErk expression by tumor cells correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor by either or both biomarker assessments.

This invention further provides a method for treating tumors or tumor metastases in a patient, comprising the steps of: diagnosing a patient's likely responsiveness to an IGF-1R kinase inhibitor, by both assessing the level of the biomarker pHER3 expressed by the tumor cells of the patient, wherein high levels of the biomarker pHER3 expression by tumor cells correlates with high sensitivity to inhibition by IGF-1R kinase inhibitors; and assessing the level of the biomarker pErk expressed by the tumor cells of the patient, wherein low levels of the biomarker pErk expression by tumor cells correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor by either or both biomarker assessments.

This invention further provides a method for treating tumors or tumor metastases in a patient, comprising the steps of: diagnosing a patient's likely responsiveness to an IGF-1R kinase inhibitor, by both assessing the level of a biomarker selected from HER3 and pHER3 expressed by the tumor cells of the patient, wherein high levels of the biomarker HER3 or pHER3 expression by tumor cells correlates with high sensitivity to inhibition by IGF-1R kinase inhibitors; and assessing whether the tumor cells have undergone an epithelial-mesenchymal transition, by assessing an epithelial or mesenchymal biomarker expressed by a tumor cell, wherein high expression levels of an epithelial biomarker correlates with high sensitivity to inhibition by IGF-1R kinase inhibitors, and wherein a high expression levels of an mesenchymal biomarker correlates with low sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor by any of the biomarker assessments. The epithelial or mesenchymal biomarker assessed can be any of the epithelial or mesenchymal biomarkers disclosed herein.

In any of the methods of the invention described herein, where a biomarker utilized in the method is pHER3, the term "pHER3" refers to "phosphorylated HER3 protein", wherein "HER3" is for example the protein encoded by the human HER3 gene, with NCBI GeneID number of 2065), and HER3 is phosphorylated at the site Y1289 (in the human protein). In embodiments of any of the inventions described herein where pHER3 is involved and wherein the tumor cells or patient is non-human, the HER3 is the corresponding animal homolog(s) of HER3, and pHER3 is phosphorylated at an analogous amino acid residue (N.B. the numbering of the phosphorylated residue may vary, depending on the species, but will be readily apparent to one of skill in the art by examination of the animal sequence homolous to the amino acid sequence around the human HER3 phosphorylation site).

In the methods of this invention, the level of Her3 and pHER3 biomarker expressed by a tumor cell can be assessed by using any of the standard bioassay procedures known in the art for determination of the level of expression of a protein or a phosphoprotein, including immunological methods for the determination of the level of phosphoproteins, including for example ELISA, RIA, immunoprecipitation, immunoblotting, immunofluorescence microscopy, or the like, as described in more detail herein, or for example protein purification methods, or protein function or activity assays. In a preferred embodiment, for assay of human pHER3, an antibody produced from a hybridoma (e.g. an IgG fraction purified by protein G affinity chromatography) elicited from an animal immunized with a synthetic phosphopeptide corresponding to residues surrounding Y1289 in human pHER3 is used in an immunoassay.

In the methods of this invention, Her3 or pHER3 biomarker expression level can be assessed relative to the expression of a control molecule whose expression level remains constant (e.g. a "housekeeping" gene, such as GAPDH, β-actin, tubulin, or the like). Her3 or pHER3 biomarker expression level can also be assessed relative to the another type of tumor cell biomarker (i.e. epithelial, mesenchymal), or to the biomarker level in non-tumor cells of the same tissue, or another cell or tissue source used as an assay reference. For example, one of the cell lines described herein in the experimental section in which Her3 or pHER3 level was determined and correlated with sensitivity of tumor cell growth to inhibition by an IGF-1R kinase inhibitor may be used as an assay reference.

As described herein, this invention provides methods using different biomarkers to predict tumor sensitivity to inhibition by IGF-1R kinase inhibitors. Each of these methods have potential advantages and disadvantages, and while the preferred method will ultimately depend on individual patient circumstances, the use of multiple diagnostic methods will likely improve one's ability to predict the likely outcome of a therapeutic regimen comprising use of an IGF-1R kinase inhibitor. Therefore, this invention provides the method for treating tumors or tumor metastases in a patient comprising the initial use, either simultaneously or sequentially, of two or more of any of the diagnostic methods as described hereinfor for predicting sensitivity to inhibition by IGF-1R kinase inhibitors, followed by administering to said patient a therapeutically effective amount of an IGF-1R kinase inhibitor if one or more of the diagnostic methods indicate that the patient is potentially responsive to an IGF-1R kinase inhibitor.

Factors to be considered in determining the preferred diagnostic method for predicting tumor sensitivity to inhibition by IGF-1R kinase inhibitors include both inherent characteristics of each of the methods and technical considerations affecting the use of the methods. For example, a small number of tumor cells have been described to harbor mutations in the gene encoding E-cadherin (e.g. HCT-116, Colo205, and DU4475 tumor cells; Buck, E., et al. (2007) Mol Cancer Ther 6:532-541). Although E-cadherin in these cell lines is not transcriptionally repressed, cells fail to form homotypic cell adhesion due to this mutation. Therefore these tumor cells are phenotypically mesenchymal-like but have not undergone EMT, and thus retain the sensitivity to IGF-1R kinase inhibitors expected of an epithelial tumor cell. Thus, a morphometric cell analysis would wrongly predict relatively poor sensitivity to IGF-1R kinase inhibitors for this type of tumor cell. However, a morphometric cell analysis would still accurately predict sensitivity for the majority of tumor cells, and is a relatively simple and inexpensive analysis. Also, as described above, certain epithelial or mesenchymal biomarkers are preferred over others in diagnostic methods using a single biomarker. An improved ability to correctly predict sensitivity to IGF-1R kinase inhibitors can often be achieved by employing two or more biomarker determinations in the diagnostic method. In general, assessing the methylation status of E-cadherin gene promoter expressed by a tumor cell, wherein lack of E-cadherin gene promoter methylation correlates with high sensitivity to inhibition by IGF-1R kinase inhibitors, appears to be very reliable biomarker for predicting sensitivity to IGF-1R kinase inhibitors. Assessing the level of tumor pErk also seems to be a particularly reliable biomarker for predicting sensitivity to IGF-1R kinase inhibitors, in that no examples of tumor cells with high pErk have yet to be identified that are not relatively insensitive to IGF-1R kinase inhibitors.

Determination of epithelial or mesenchymal biomarker level can be assessed by a number of different approaches, including direct analysis of proteins that segregate as epithelial related (e.g. E-cadherin) or mesenchymal related (e.g. vimentin, Zeb1) biomarkers. An advantage of this approach is that EMT markers are read directly. However, this approach also requires sufficient quantities of tissue in order to perform an analysis (e.g. immunohistochemistry). Sufficient quantities of tissue may be difficult to obtain from certain procedures such as FNA (fine needle aspiration). Core biopsies provide larger amounts of tissue, but are sometimes not routinely performed during diagnoses. Alternatively, these EMT biomarkers could be evaluated based upon the expression level of their encoding RNA transcripts using a quantitative PCR based approach. An advantage of this approach is that very few tumor cells are required for this measurement, and it is very likely that sufficient material may be obtained via an FNA. However, here the transcript levels for a given biomarker may be derived from both tumor cells as well as infiltrating stromal cells from the tumor. Given that stromal cells also express mesenchymal cell markers, this may obscure detection of the EMT status for tumor cells. Use of in situ hybridization (e.g. FISH) or tissue microdisection may be useful here to overcome this potential limitation.

Given that the expression level of E-cadherin is a hallmark of the EMT status for a tumor cell, EMT may also be evaluated based upon the methylation status of the E-cadherin promoter, and be used predict sensitivity to IGF-1R kinase inhibitors, as described herein. Methylation silences transcription, and so a high level of methylation correlates with a mesenchymal-like state. A potential benefit of this approach is that, like measurement of transcript levels, measuring the methylation status of DNA would likely require very little material. Sufficient material could likely be obtained from an FNA and would not require a core biopsy. Additionally, since this approach involves evaluation of DNA and not RNA, it is likely to be a more stable read-out over time, such as during medium or long term storage of a sample.

The data described herein indicates that perk is a biomarker predictive of relative insensitivity to IGF-1R kinase inhibitors. High levels of pErk are observed in mesenchymal tumor cells, as might be expected given that mesenchymal biomarkers are also a predictor of relative insensitivity to IGF-1R kinase inhibitors, as also described herein. As indicated herein, the level of tumor pErk seems to be a particularly reliable biomarker for predicting sensitivity to IGF-1R kinase inhibitors. However, one potential disadvantage of this biomarker is that levels of pErk are potentially unstable over time if tumor samples are not handled appropriately. Thus, application of this biomarker as a diagnostic would require that tumor material be prepared in a way that preserves the phosphorylation state of the Erk protein (i.e. inhibits dephosphorylation of the protein), such as for example by being snap-frozen upon biopsy, or being rapidly fixed using a protein denaturant. Such methods are however well known in the art, and routinely employed to preserve tissue samples.

In the methods described herein the tumor cell will typically be from a patient diagnosed with cancer, a precancerous condition, or another form of abnormal cell growth, and in need of treatment. The cancer may be lung cancer (e.g. non-small cell lung cancer (NSCLC)), pancreatic cancer, head and neck cancer, gastric cancer, breast cancer, colon cancer, ovarian cancer, or any of a variety of other cancers described herein below. The cancer is preferably one known to be potentially treatable with an IGF-1R kinase inhibitor.

In the methods of this invention, epithelial or mesenchymal biomarker expression level can be assessed relative to a control molecule whose expression level remains constant throughout EMT, or when comparing tumor cells expressing either epithelial or mesenchymal transition states as indicated by molecular biomarkers (e.g. a "housekeeping" gene, such as GAPDH, β-actin, tubulin, or the like). Biomarker expression level can also be assessed relative to the other type of tumor cell biomarker (i.e. epithelial compared to mesenchymal), or to the biomarker level in non-tumor cells of the same tissue, or another cell or tissue source used as an assay reference.

In the methods of this invention, the level of an epithelial or mesenchymal biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, RT-PCR, in situ hybridization, cDNA microarray, or the like, as described in more detail below.

In the methods of this invention, the expression level of a tumor cell epithelial or mesenchymal biomarker is preferably assessed by assaying a tumor biopsy. However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

In the methods of this invention, the tumor cell can be a lung cancer tumor cell (e.g. non-small cell lung cancer (NSCLC)), a pancreatic cancer tumor cell, a breast cancer tumor cell, a head and neck cancer tumor cell, a gastric cancer tumor cell, a colon cancer tumor cell, an ovarian cancer tumor cell, or a tumor cell from any of a variety of other cancers as described herein below. The tumor cell is preferably of a type known to or expected to express IGF-1R kinase, as do all tumor cells from solid tumors. The IGF-1R kinase can be wild type or a mutant form.

In the methods of this invention, the IGF-1R kinase inhibitor can be any IGF-1R kinase inhibitor as described herein below, including pharmacologically acceptable salts or polymorphs thereof.

The following methods represent additional specific embodiments of the method of the invention.

The present invention provides a method of predicting the sensitivity of tumor growth to inhibition by an IGF-1R kinase inhibitor, comprising: assessing the level of an epithelial biomarker expressed by cells of the tumor; and predicting the sensitivity of tumor growth to inhibition by an IGF-1R kinase inhibitor, wherein high expression levels of tumor cell epithelial biomarkers correlate with high sensitivity of tumor growth to inhibition by IGF-1R kinase inhibitors.

The present invention provides a method of predicting the sensitivity of tumor growth to inhibition by an IGF-1R kinase inhibitor, comprising: assessing the level of a mesenchymal biomarker expressed by cells of the tumor; and predicting the sensitivity of tumor growth to inhibition by an IGF-1R kinase inhibitor, wherein high expression levels of tumor cell mesenchymal biomarkers correlate with low sensitivity of tumor growth to inhibition by IGF-1R kinase inhibitors.

The present invention provides a method of predicting whether a cancer patient is afflicted with a tumor that will respond effectively to treatment with an IGF-1R kinase inhibitor, comprising: assessing the level of an epithelial biomarker expressed by cells of the tumor; and predicting if the tumor will respond effectively to treatment with an IGF-1R kinase inhibitor, wherein high expression levels of tumor cell epithelial biomarkers correlate with a tumor that will respond effectively to treatment with an IGF-1R kinase inhibitor.

In the methods of this invention, the tumor can be a lung cancer tumor (e.g. non-small cell lung cancer (NSCLC)), a pancreatic cancer tumor, a breast cancer tumor, a head and neck cancer tumor, a gastric cancer tumor, a colon cancer tumor, an ovarian cancer tumor, or a tumor from any of a variety of other cancers as described herein below. The tumor is preferably of a type whose cells are known to or expected to express IGF-1R kinase, as do all solid tumors. The IGF-1R kinase can be wild type or a mutant form.

The present invention provides a method of predicting whether a cancer patient is afflicted with a tumor that will respond effectively to treatment with an IGF-1R kinase inhibitor, comprising: assessing the level of a mesenchymal biomarker expressed by cells of the tumor; and predicting if the tumor will respond effectively to treatment with an IGF-1R kinase inhibitor, wherein high expression levels of tumor cell mesenchymal biomarkers correlate with a tumor that will respond less effectively to treatment with an IGF-1R kinase inhibitor.

The present invention provides a method of predicting the sensitivity of tumor cell growth to inhibition by an IGF-1R kinase inhibitor comprising: determining the tumor cell level of at least one epithelial biomarker polypeptide; determining the tumor cell level of at least one control polypeptide; comparing the tumor cell level of at least one epithelial biomarker polypeptide to the tumor cell level of at least one control polypeptide; wherein a high ratio of tumor cell biomarker polypeptide to tumor cell control polypeptide indicates a high predicted sensitivity of tumor cell growth to inhibition by an IGF-1R kinase inhibitor. For this method, examples of useful epithelial biomarker polypeptides include E-cadherin, γ-catenin, keratin 8, keratin 18, and Brk.

The present invention provides a method of predicting the sensitivity of tumor cell growth to inhibition by an IGF-1R kinase inhibitor comprising: determining the tumor cell level of at least one epithelial biomarker polynucleotide that encodes a polypeptide; determining the tumor cell level of at least one control polynucleotide; comparing the tumor cell level of at least one epithelial biomarker polynucleotide that encodes a polypeptide to the tumor cell level of at least one control polynucleotide; wherein a high ratio of tumor cell biomarker polynucleotide to tumor cell control polynucleotide indicates a high predicted sensitivity of tumor cell growth to inhibition by an IGF-1R kinase inhibitor. For this method examples of polypeptides encoded by the epithelial biomarker polynucleotide include E-cadherin, γ-catenin, keratin 8, keratin 18, and Brk.

The present invention provides a method of predicting the sensitivity of tumor cell growth to inhibition by an IGF-1R kinase inhibitor comprising: determining the tumor cell level of at least one mesenchymal biomarker polypeptide; determining the tumor cell level of at least one control polypeptide; comparing the tumor cell level of at least one mesenchymal biomarker polypeptide to the tumor cell level of at least one control polypeptide; wherein a low ratio of tumor cell biomarker polypeptide to tumor cell control polypeptide indicates a high predicted sensitivity of tumor cell growth to inhibition by an IGF-1R kinase inhibitor. For this method, examples of useful mesenchymal biomarker polypeptides include vimentin and fibronectin.

The present invention provides a method of predicting the sensitivity of tumor cell growth to inhibition by an IGF-1R kinase inhibitor comprising: determining the tumor cell level of at least one mesenchymal biomarker polynucleotide that encodes an polypeptide; determining the tumor cell level of at least one control polynucleotide; comparing the tumor cell level of at least one mesenchymal biomarker polynucleotide that encodes an polypeptide to the tumor cell level of at least one control polynucleotide; wherein a low ratio of tumor cell biomarker polynucleotide to tumor cell control polynucleotide indicates a high predicted sensitivity of tumor cell growth to inhibition by an IGF-1R kinase inhibitor. For this method, examples of useful polypeptides encoded by the biomarker polynucleotide include vimentin and fibronectin.

The present invention provides a method of predicting the sensitivity of tumor cell growth to inhibition by an IGF-1R kinase inhibitor comprising: determining the tumor cell level of at least one epithelial biomarker polypeptide; determining a non-tumor cell level of at least one epithelial biomarker polypeptide; comparing the tumor cell level of at least one epithelial biomarker polypeptide to the non-tumor cell level of at least one epithelial biomarker polypeptide; wherein a high ratio of tumor cell biomarker polypeptide to non-tumor cell biomarker polypeptide indicates a high predicted sensitivity of tumor cell growth to inhibition by an IGF-1R kinase inhibitor. For this method, examples of useful epithelial biomarker polypeptide include E-cadherin, γ-catenin, keratin 8, keratin 18, and Brk.

The present invention provides a method of predicting the sensitivity of tumor cell growth to inhibition by an IGF-1R kinase inhibitor comprising: determining the tumor cell level of at least one epithelial biomarker polynucleotide that encodes an polypeptide; determining a non-tumor cell level of at least one epithelial biomarker polynucleotide that encodes an polypeptide; comparing the tumor cell level of at least one epithelial biomarker polynucleotide that encodes an polypeptide to the non-tumor cell level of at least one epithelial biomarker polynucleotide that encodes an polypeptide; wherein a high ratio of tumor cell biomarker polynucleotide to non-tumor cell biomarker polynucleotide indicates a high predicted sensitivity of tumor cell growth to inhibition by an IGF-1R kinase inhibitor. For this method, examples of useful polypeptides encoded by the epithelial biomarker polynucleotide include E-cadherin, γ-catenin, keratin 8, keratin 18, and Brk.

The present invention provides a method of predicting the sensitivity of tumor cell growth to inhibition by an IGF-1R kinase inhibitor comprising: determining the tumor cell level of at least one mesenchymal biomarker polypeptide; determining a non-tumor cell level of at least one mesenchymal biomarker polypeptide; comparing the tumor cell level of at least one mesenchymal biomarker polypeptide to the non-tumor cell level of at least one mesenchymal biomarker polypeptide; wherein a low ratio of tumor cell biomarker polypeptide to non-tumor cell biomarker polypeptide indicates a high predicted sensitivity of tumor cell growth to inhibition by an IGF-1R kinase inhibitor. For this method, examples of useful mesenchymal biomarker polypeptides include vimentin and fibronectin.

The present invention provides a method of predicting the sensitivity of tumor cell growth to inhibition by an IGF-1R kinase inhibitor comprising: determining the tumor cell level of at least one mesenchymal biomarker polynucleotide that encodes an polypeptide; determining a non-tumor cell level of at least one mesenchymal biomarker polynucleotide that encodes an polypeptide; comparing the tumor cell level of at least one mesenchymal biomarker polynucleotide that encodes an polypeptide to the non-tumor cell level of at least one mesenchymal biomarker polynucleotide that encodes an polypeptide; wherein a low ratio of tumor cell biomarker polynucleotide to non-tumor cell biomarker polynucleotide indicates a high predicted sensitivity of tumor cell growth to inhibition by an IGF-1R kinase inhibitor. For this method, examples of useful polypeptides encoded by the biomarker polynucleotide include vimentin and fibronectin.

The present invention provides a method of predicting the sensitivity of tumor cell growth to inhibition by an IGF-1R kinase inhibitor comprising: determining the tumor cell level of at least one epithelial biomarker polypeptide; determining the tumor cell level of at least one mesenchymal biomarker polypeptide; comparing the level of at least one epithelial biomarker polypeptide to the level of at least one mesenchymal biomarker polypeptide; wherein a high ratio of epithelial biomarker polypeptide to mesenchymal biomarker polypeptide indicates a high predicted sensitivity of tumor cell growth to inhibition by an IGF-1R kinase inhibitor. For this method, examples of useful epithelial biomarker polypeptides include E-cadherin, γ-catenin, keratin 8, keratin 18, and Brk. For this method, examples of useful mesenchymal biomarker polypeptides include vimentin and fibronectin.

The present invention provides a method of predicting the sensitivity of tumor cell growth to inhibition by an IGF-1R kinase inhibitor comprising: determining the tumor cell level of at least one epithelial biomarker polynucleotide that encodes a polypeptide; determining the tumor cell level of at least one mesenchymal biomarker polynucleotide that encodes a polypeptide; (c) comparing the level of at least one epithelial biomarker polynucleotide to the level of at least one mesenchymal biomarker polynucleotide; wherein a high ratio of epithelial biomarker polynucleotide to mesenchymal biomarker polynucleotide indicates a predicted high sensitivity of tumor cell growth to inhibition by an IGF-1R kinase inhibitor. For this method, examples of useful polypeptides encoded by the epithelial biomarker polynucleotide include E-cadherin, γ-catenin, keratin 8, keratin 18, and Brk. For this method, examples of useful polypeptides encoded by the mesenchymal biomarker polynucleotide include vimentin and fibronectin.

The present invention provides a method of assessing whether a cancer patient is afflicted with a cancer that will respond effectively to treatment with an IGF-1R kinase inhibitor, the method comprising comparing: the level of expression of a mesenchymal biomarker in a patient sample; and the normal level of expression of the biomarker in a control non-cancer sample, wherein a significant increase in the level of expression of the mesenchymal biomarker in the patient sample over the normal level is an indication that the patient is afflicted with a cancer which is less likely to respond effectively to treatment with an IGF-1R kinase inhibitor. For this method, examples of useful mesenchymal biomarkers include vimentin and fibronectin, and nucleic acids encoding for these proteins.

The present invention provides a method of assessing whether a cancer patient is afflicted with a cancer that will respond effectively to treatment with an IGF-1R kinase inhibitor, the method comprising comparing: the level of expression of an epithelial biomarker in a patient sample; and the normal level of expression of the biomarker in a control non-cancer sample, wherein a significant decrease in the level of expression of the epithelial biomarker in the patient sample over the normal level is an indication that the patient is afflicted with a cancer which is less likely to respond effectively to treatment with an IGF-1R kinase inhibitor. For this method, examples of useful epithelial biomarkers include E-cadherin, γ-catenin, keratin 8, keratin 18, and Brk, and nucleic acids encoding for these proteins.

The present invention provides a method of assessing whether a cancer patient is afflicted with a cancer that will respond effectively to treatment with an IGF-1R kinase inhibitor, the method comprising comparing: the level of expression of an epithelial biomarker in a patient sample; and the level of expression of a mesenchymal biomarker in a patient sample, wherein a high ratio of the level of expression of the epithelial biomarker to the level of expression of the mesenchymal biomarker is an indication that the patient is afflicted with a cancer which is likely to respond effectively to treatment with an IGF-1R kinase inhibitor. For this method, examples of useful epithelial biomarkers include E-cadherin, γ-catenin, keratin 8, keratin 18, and Brk, and nucleic acids encoding for these proteins. For this method, examples of useful mesenchymal biomarkers include vimentin and fibronectin, and nucleic acids encoding for these proteins.

In any of the above methods referring to a patient sample, an example of such a sample can be a tumor biopsy.

The present invention provides a method of determining whether in a human subject a tumor will be responsive to treatment with an IGF-1R kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for one or more epithelial cell biomarker proteins or one or more epithelial cell biomarker protein-specific mRNAs; and (c) comparing the expression level in (b) to the level of biomarker expression in a normal control, or to the level of a control polypeptide or nucleic acid in the sample, wherein reduced expression of one or more epithelial cell biomarker proteins or one or more epithelial cell biomarker protein-specific mRNAs, with respect to the control level, indicates the presence in the human subject of a tumor which is less likely to respond effectively to treatment with an IGF-1R kinase inhibitor.

The present invention provides a method of determining whether in a human subject a tumor will be responsive to treatment with an IGF-1R kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for one or more mesenchymal cell biomarker proteins or one or more mesenchymal cell biomarker protein-specific mRNAs; and (c) comparing the expression level in (b) to the level of biomarker expression in a normal control, or to the level of a control polypeptide or nucleic acid in the sample, wherein increased expression of one or more mesenchymal cell biomarker proteins or one or more mesenchymal cell biomarker protein-specific mRNAs, with respect to the control level, indicates the presence in the human subject of a tumor which is less likely to respond effectively to treatment with an IGF-1R kinase inhibitor.

The present invention provides a method of determining the likelihood that a patient with a tumor will show relatively long survival benefit from therapy with an IGF-1R kinase inhibitor, comprising determining the level of one or more epithelial biomarkers in the cells of the tumor, comparing said level with the level of epithelial biomarker expression in a non-tumor control, or to the level of a control polypeptide or nucleic acid in the tumor sample, and determining whether the cells of the tumor contain a relatively high level of one or more epithelial biomarkers, a high level being indicative that a patient with a tumor will show relatively long survival benefit from therapy with an IGF-1R kinase inhibitor.

The present invention provides a method of determining the likelihood that a patient with a tumor will show relatively long survival benefit from therapy with an IGF-1R kinase inhibitor, comprising determining the level of one or more mesenchymal biomarkers in the cells of the tumor, comparing said level with the level of mesenchymal biomarker expression in a non-tumor control, or to the level of a control polypeptide or nucleic acid in the tumor sample, and determining whether the cells of the tumor contain a relatively low level of one or more mesenchymal biomarkers, a low level being indicative that a patient with a tumor will show relatively long survival benefit from therapy with an IGF-1R kinase inhibitor.

The present invention provides a method for determining for a patient with a tumor the likelihood that said patient will show relatively long survival benefit from therapy with an IGF-1R kinase inhibitor, comprising: determining the level of one or more epithelial biomarkers in the cells of the tumor, comparing said level with the level of epithelial biomarker expression in a non-tumor control, or to the level of a control polypeptide or nucleic acid in the tumor sample, and determining whether the cells of the tumor contain a relatively high level of one or more epithelial biomarkers; determining the level of one or more mesenchymal biomarkers in the cells of the tumor, comparing said level with the level of mesenchymal biomarker expression in a non-tumor control, or to the level of a control polypeptide or nucleic acid in the tumor sample, and determining whether the cells of the tumor contain a relatively low level of one or more mesenchymal biomarkers, wherein a high level of one or more epithelial biomarkers and a low level of one or more mesenchymal biomarkers is indicative that a patient with a tumor will show relatively long survival benefit from therapy with an IGF-1R kinase inhibitor.

The present invention provides a method of determining a prognosis for survival for a patient with a neoplastic condition in response to therapy with an IGF-1R kinase inhibitor, comprising: measuring the level of an epithelial biomarker associated with neoplastic cells, and comparing said level of epithelial biomarker to a non-neoplastic epithelial biomarker reference level, or to the level of a control polypeptide or nucleic acid associated with the neoplastic cells, wherein a decreased level of epithelial biomarker associated with the neoplastic cells correlates with decreased survival of said patient.

The present invention provides a method of determining a prognosis for survival for a patient with a neoplastic condition in response to therapy with an IGF-1R kinase inhibitor, comprising: measuring the level of an mesenchymal biomarker associated with neoplastic cells, and comparing said level of mesenchymal biomarker to a non-neoplastic mesenchymal biomarker reference level, or to the level of a control polypeptide or nucleic acid associated with the neoplastic cells, wherein an increased level of mesenchymal biomarker associated with the neoplastic cells correlates with decreased survival of said patient.

For assessment of tumor cell epithelial or mesenchymal biomarker expression, patient samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from a patient, or other patient sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g., fixation.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e. using reagents, such as different fluorescent probes, for each biomarker) or in individual reaction mixtures corresponding to one or more of the biomarkers.

The level of expression of a biomarker in normal (i.e. non-cancerous) human tissue can be assessed in a variety of ways. In one embodiment, this normal level of expression is assessed by assessing the level of expression of the biomarker in a portion of cells which appears to be non-cancerous, and then comparing this normal level of expression with the level of expression in a portion of the tumor cells. Alternately, and particularly as further information becomes available as a result of routine performance of the methods described herein, population-average values for normal expression of the biomarkers of the invention may be used. In other embodiments, the 'normal' level of expression of a biomarker may be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g. a tumor-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S. and Urbanic-zky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J. Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g. a mesenchymal biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials.

Two commonly used radioactive isotopes are $^{125}I$ and $^3H$. Standard radioactive isotopic labeling procedures include the chloramine T, lactoperoxidase and Bolton-Hunter methods for $^{125}I$ and reductive methylation for $^3H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

The invention also encompasses kits for detecting the presence of a biomarker protein or nucleic acid in a biological sample. Such kits can be used to determine if a subject is suffering from or is at increased risk of developing a tumor that is less susceptible to inhibition by IGF-1R kinase inhibitors. For example, the kit can comprise a labeled compound or agent capable of detecting a biomarker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a biomarker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

The present invention further provides a method for treating tumors or tumor metastases in a patient, comprising the steps of diagnosing a patient's likely responsiveness to an IGF-1R kinase inhibitor by assessing whether the tumor cells have undergone an epithelial-mesenchymal transition, by for example any of the methods described herein for determining the expression level of tumor cell epithelial and/or mesenchymal biomarkers, and administering to said patient a therapeutically effective amount of an IGF-1R kinase inhibitor. For this method, an example of a preferred IGF-1R kinase inhibitor would be one with similar characteristics (e.g. selectivity, potency) to Compound 66, including pharmacologically acceptable salts or polymorphs thereof. In this method one or more additional anti-cancer agents or treatments can be co-administered simultaneously or sequentially with the IGF-1R kinase inhibitor, as judged to be appropriate by the administering physician given the prediction of the likely responsiveness of the patient to an IGF-1R kinase inhibitor, in combination with any additional circumstances pertaining to the individual patient.

The present invention further provides a method for treating tumors or tumor metastases in a patient with an IGF-1R kinase inhibitor, with or without other anti-cancer compounds, comprising the initial step of diagnosing a patient's likely responsiveness to an IGF-1R kinase inhibitor by utilizing E-cadherin gene promoter methylation as a predicter of a patient's likely responsiveness to an IGF-1R kinase inhibitor, wherein no or low CDH1 promoter methylation is indicative of greater sensitivity to IGF1R kinase inhibitors, with or without other biomarker determination methods for predicting responsiveness to an IGF-1R kinase inhibitor. In this context, when multiple methods for diagnosing responsiveness to IGF1-R kinase are employed, if at least one of the methods for diagnosing a patient's likely responsiveness to an IGF-1R kinase inhibitor indicates that the patient would likely be responsive to an IGF-1R kinase inhibitor, the patient is diagnosed to be potentially responsive to an IGF-1R kinase inhibitor, and thus administered a therapeutically effective amount of an IGF-1R kinase inhibitor.

The present invention thus provides a method for treating tumors or tumor metastases in a patient, comprising the steps of: diagnosing a patient's likely responsiveness to an IGF-1R kinase inhibitor, by assessing the methylation status of E-cadherin gene promoter in a tumor cell, wherein low or no E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

The present invention also provides a method for treating tumors or tumor metastases in a patient, comprising the steps of: diagnosing a patient's likely responsiveness to an IGF-1R kinase inhibitor, by both assessing the level of the biomarker perk expressed by the tumor cells of the patient, wherein low levels of the biomarker pErk expression by tumor cells correlates with high sensitivity to inhibition by IGF-1R kinase inhibitors; and assessing the methylation status of E-cadherin gene promoter in a tumor cell, wherein low or no E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor.

The present invention also provides a method for treating tumors or tumor metastases in a patient, comprising the steps of: diagnosing a patient's likely responsiveness to an IGF-1R kinase inhibitor, by assessing the gene expression level of an epithelial or mesenchymal biomarker expressed by the tumor cells of the patient, wherein low levels of mesenchymal biomarker expression or high levels of epithelial biomarker expression by tumor cells correlates with high sensitivity to inhibition by IGF-1R kinase inhibitors; and also assessing the methylation status of E-cadherin gene promoter in a tumor cell, wherein no or low E-cadherin gene promoter methylation correlates with high sensitivity to inhibition by IGF-1R kinase inhibitors; and administering to said patient a therapeutically effective amount of an IGF-1R kinase inhibitor if the patient is diagnosed to be potentially responsive to an IGF-1R kinase inhibitor. Assessment of the gene expression level of an epithelial or mesenchymal biomarker can for example be determined by measuring biomarker protein or mRNA transcript levels.

It will be appreciated by one of skill in the medical arts that the exact manner of administering to said patient of a therapeutically effective amount of an IGF-1R kinase inhibitor following a diagnosis of a patient's likely responsiveness to an IGF-1R kinase inhibitor will be at the discretion of the attending physician. The mode of administration, including dosage, combination with other anti-cancer agents, timing and frequency of administration, and the like, may be affected by the diagnosis of a patient's likely responsiveness to an IGF-1R kinase inhibitor, as well as the patient's condition and history. Thus, even patients diagnosed with tumors predicted to be relatively insensitive to IGF-1R kinase inhibitors may still benefit from treatment with such inhibitors, particularly in combination with other anti-cancer agents, or agents that may alter a tumor's sensitivity to IGF-1R kinase inhibitors.

The present invention further provides a method for treating tumors or tumor metastases in a patient, comprising the steps of diagnosing a patient's likely responsiveness to an IGF-1R kinase inhibitor by assessing whether the tumor cells have undergone an epithelial-mesenchymal transition, by for example any of the methods described herein for determining the expression level of tumor cell epithelial and/or mesenchymal biomarkers, identifying the patient as one who is likely to demonstrate an effective response to treatment with an IGF-1R kinase inhibitor, and administering to said patient a therapeutically effective amount of an IGF-1R kinase inhibitor.

The present invention further provides a method for treating tumors or tumor metastases in a patient, comprising the steps of diagnosing a patient's likely responsiveness to an IGF-1R kinase inhibitor by assessing whether the tumor cells have undergone an epithelial-mesenchymal transition, by for example any of the methods described herein for determining the expression level of tumor cell epithelial and/or mesenchymal biomarkers, identifying the patient as one who is less likely or not likely to demonstrate an effective response to treatment with an IGF-1R kinase inhibitor, and treating said patient with an anti-cancer therapy other than an IGF-1R kinase inhibitor.

The present invention further provides a method of identifying an epithelial biomarker whose expression level is predictive of the sensitivity of tumor cell growth to inhibition by an IGF-1R kinase inhibitor, comprising: (a) measuring the expression level of a candidate epithelial biomarker in a panel of tumor cells that displays a range of sensitivities to an IGF-1R kinase inhibitor, and (b) identifying a correlation between the expression level of said candidate epithelial biomarker in the tumor cells and the sensitivity of tumor cell growth to inhibition by the IGF-1R kinase inhibitor, wherein a correlation of high levels of the epithelial biomarker with high sensitivity of tumor cell growth to inhibition by the IGF-1R kinase inhibitor indicates that the expression level of said epithelial biomarker is predictive of the sensitivity of tumor cell growth to inhibition by an IGF-1R kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying a mesenchymal biomarker whose expression level is predictive of the sensitivity of tumor cell growth to inhibition by an IGF-1R kinase inhibitor, comprising: (a) measuring the expression level of a candidate mesenchymal biomarker in a panel of tumor cells that displays a range of sensitivities to an IGF-1R kinase inhibitor, and (b) identifying a correlation between the expression level of said candidate mesenchymal biomarker in the tumor cells and the sensitivity of tumor cell growth to inhibition by the IGF-1R kinase inhibitor, wherein a correlation of high levels of the mesenchymal biomarker with low sensitivity of tumor cell growth to inhibition by the IGF-1R kinase inhibitor indicates that the expression level of said mesenchymal biomarker is predictive of the lack of sensitivity of tumor cell growth to inhibition by an IGF-1R kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying an epithelial biomarker that is diagnostic for more effective treatment of a neoplastic condition with an IGF-1R kinase inhibitor, comprising: (a) measuring the level of a candidate epithelial biomarker in neoplastic cell-containing samples from patients with a neoplastic condition, and (b) identifying a correlation between the level of said candidate epithelial biomarker in the sample from the patient with the effectiveness of treatment of the neoplastic condition with an IGF-1R kinase inhibitor, wherein a correlation of high levels of the epithelial biomarker with more effective treatment of the neoplastic condition with an IGF-1R kinase inhibitor indicates that said epithelial biomarker is diagnostic for more effective treatment of the neoplastic condition with an IGF-1R kinase inhibitor.

The present invention further provides a method of identifying a mesenchymal biomarker that is diagnostic for less effective treatment of a neoplastic condition with an IGF-1R kinase inhibitor, comprising: (a) measuring the level of a candidate mesenchymal biomarker in neoplastic cell-containing samples from patients with a neoplastic condition, and (b) identifying a correlation between the level of said candidate mesenchymal biomarker in the sample from the patient with the effectiveness of treatment of the neoplastic condition with an IGF-1R kinase inhibitor, wherein a correlation of high levels of the mesenchymal biomarker with less effective treatment of the neoplastic condition with an IGF-1R kinase inhibitor indicates that said mesenchymal biomarker is diagnostic for less effective treatment of the neoplastic condition with an IGF-1R kinase inhibitor.

The effectiveness of treatment in the preceding methods can for example be determined by measuring the decrease in size of tumors present in the patients with the neoplastic condition, or by assaying a molecular determinant of the degree of proliferation of the tumor cells.

The present invention provides a method of identifying an epithelial biomarker that is diagnostic for increased survival of a patient with a neoplastic condition when treated with an IGF-1R kinase inhibitor, comprising: (a) measuring the level of the candidate epithelial biomarker in neoplastic cell-containing samples from patients with a neoplastic condition, and (b) identifying a correlation between the level of said candidate epithelial biomarker in the sample from the patient with the survival of that patient when treated with an IGF-1R kinase inhibitor, wherein the correlation of an epithelial biomarker with survival in said patients indicates said epithelial biomarker is diagnostic for increased survival of a patient with said neoplastic condition when treated with an IGF-1R kinase inhibitor.

The present invention provides a method of identifying a mesenchymal biomarker that is diagnostic for decreased survival of a patient with a neoplastic condition when treated with an IGF-1R kinase inhibitor, comprising: (a) measuring the level of the candidate mesenchymal biomarker in neoplastic cell-containing samples from patients with a neoplastic condition, and (b) identifying an inverse correlation between the level of said candidate mesenchymal biomarker in the sample from the patient with the survival of that patient when treated with an IGF-1R kinase inhibitor, wherein the inverse correlation of a mesenchymal biomarker with survival in said patients indicates said mesenchymal biomarker is diagnostic for decreased survival of a patient with said neoplastic condition when treated with an IGF-1R kinase inhibitor.

The present invention provides a method for the identification of an agent that enhances sensitivity of the growth of a tumor cell to an IGF-1R kinase inhibitor, said tumor cell having being characterized as one that has previously undergone an epithelial-mesenchymal transition, comprising contacting a sample of said tumor cells with an IGF-1R kinase inhibitor, contacting an identical sample of said tumor cells with an IGF-1R kinase inhibitor in the presence of a test agent, comparing the IGF-1R kinase inhibitor-mediated growth inhibition in the presence and absence of the test agent, and determining whether the test agent is an agent that enhances sensitivity of the growth of the tumor cell to an IGF-1R kinase inhibitor. For this method, an example of a preferred IGF-1R kinase inhibitor would be a compound with similar characteristics to Compound 66, including pharmacologically acceptable salts or polymorphs thereof. In one embodiment of this method the sample of tumor cells can be cells in vitro, such as a tumor cell line or a primary tumor cell culture. In an alternative embodiment the sample of tumor cells can be cells in vivo, such as tumor cells in a mouse xenograft. In the latter embodiment, tumor cell growth can for example be determined by monitoring a molecular marker of growth or a gross measurement of tumor growth, e.g. tumor dimensions or weight.

Suitable test agents which can be tested in the preceding method include combinatorial libraries, defined chemical entities, peptide and peptide mimetics, oligonucleotides and natural product libraries, such as display (e.g. phage display libraries) and antibody products. Test agents may be used in an initial screen of, for example, 10 substances per reaction, and the substances of these batches which show inhibition or activation tested individually. Test agents may be used at a concentration of from 1 nM to 1000 µM, preferably from 1 µM to 100 µM, more preferably from 1 µM to 10 µM.

Agents which enhances sensitivity of the growth of a tumor cell to an IGF-1R kinase inhibitor which have been identified by the preceding methods can be used in the treatment of patients with cancers which are predicted to be less responsive to inhibition by IGF-1R kinase inhibitors (including lung cancer or any of the other cancer types described herein), and are an additional embodiment of this invention. Thus the present invention further provides a composition of matter comprising such an agent, which may be formulated and administered by any of the methods known in the art, including those described herein in relation to IGF-1R kinase inhibitors. Such agents that enhances sensitivity of the growth of a tumor cell to an IGF-1R kinase inhibitor may for example be agents that induce a mesenchymal-to-epithelial transition (MET), or that inhibit a specific cellular activity responsible for reduced sensitivity to IGF-1R kinase inhibitors, or induce a specific cellular activity that enhances sensitivity to IGF-1R kinase inhibitors. Examples of suitable agents include antagonists of EMT inducing agents.

The present invention further provides the preceding methods for treating tumors or tumor metastases in a patient, comprising administering to the patient a therapeutically effective amount of an IGF-1R kinase inhibitor and in addition, simultaneously or sequentially, one or more other cytotoxic, chemotherapeutic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides the preceding methods for treating tumors or tumor metastases in a patient, comprising administering to the patient a therapeutically effective amount of an IGF-1R kinase inhibitor and in addition, simultaneously or sequentially, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N-6-(3-pyridinylcarbonyl)-L-lysyl-N-6-(3-pyridinylcarbonyl)-D-lysyl-L-leucyl-N-6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl) phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides the preceding methods for treating tumors or tumor metastases in a patient, comprising administering to the patient a therapeutically effective amount of an IGF-1R kinase inhibitor and in addition, simultaneously or sequentially, one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 4,1530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606, 046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides the preceding methods for treating tumors or tumor metastases in a patient, comprising administering to the patient a therapeutically effective amount of an IGF-1R kinase inhibitor and in addition, simultaneously or sequentially, one or more tumor cell pro-apoptotic or apoptosis-stimulating agents.

The present invention further provides the preceding methods for treating tumors or tumor metastases in a patient, comprising administering to the patient a therapeutically effective amount of an IGF-1R kinase inhibitor and in addition, simultaneously or sequentially, one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); EGFR kinase inhibitors (see herein below); ras inhibitors; raf inhibitors; MEK inhibitors; mTOR inhibitors, including mTOR inhibitors that bind to and directly inhibits both mTORC1 and mTORC2 kinases; mTOR inhibitors that are dual PI3K/mTOR kinase inhibitors, such as for example the compound PI-103 as described in Fan, Q-W et al (2006) Cancer Cell 9:341-349 and Knight, Z. A. et al. (2006) Cell 125:733-747; mTOR inhibitors that are dual inhibitors of mTOR kinase and one or more other PIKK (or PIK-related) kinase family members. Such members include MEC1, TEL1, RAD3, MEI-41, DNA-PK, ATM, ATR, TRRAP, PI3K, and PI4K kinases; cyclin dependent kinase inhibitors; protein kinase C inhibitors; PI-3 kinase inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

EGFR inhibitors include, for example: [6,7-bis(2-methoxyethoxy)-4-quinazolin-4-yl]-(3-ethynylphenyl) amine (also known as OSI-774, erlotinib, or TARCEVA™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); gefitinib (also known as ZD1839 or IRESSA™; Astrazeneca) (Woodburn et al., 1997, Proc. Am. Assoc. Cancer Res. 38:633); and antibody-based EGFR kinase inhibitors. A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, TARCEVA™), or other salt forms (e.g. erlotinib mesylate). Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

EGFR kinase inhibitors also include, for example multi-kinase inhibitors that have activity on EGFR kinase, i.e. inhibitors that inhibit EGFR kinase and one or more additional kinases. Examples of such compounds include the EGFR and HER2 inhibitor CI-1033 (formerly known as PD183805; Pfizer); the EGFR and HER2 inhibitor GW-2016 (also known as GW-572016 or lapatinib ditosylate; GSK); the EGFR and JAK 2/3 inhibitor AG490 (a tyrphostin); the EGFR and HER2 inhibitor ARRY-334543 (Array BioPharma); BIBW-2992, an irreversible dual EGFR/HER2 kinase inhibitor (Boehringer Ingelheim Corp.); the EGFR and HER2 inhibitor EKB-569 (Wyeth); the VEGF-R2 and EGFR inhibitor ZD6474 (also known as ZACTNA™; AstraZeneca Pharmaceuticals), and the EGFR and HER2 inhibitor BMS-599626 (Bristol-Myers Squibb).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further provides the preceding methods for treating tumors or tumor metastases in a patient, comprising administering to the patient a therapeutically effective amount of an IGF-1R kinase inhibitor and in addition, simultaneously or sequentially, an anti-HER2 antibody or an immunotherapeutically active fragment thereof.

The present invention further provides the preceding methods for treating tumors or tumor metastases in a patient, comprising administering to the patient a therapeutically effective amount of an IGF-1R kinase inhibitor and in addition, simultaneously or sequentially, one or more additional anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080, 769, 6,194,438, 6,258,824, 6,586,447, 6,071,935, 6,495,564, 6,150,377, 6,596,735 and 6,479,513, and International Patent Publication WO 01/40217, and FGFR kinase inhibitors.

Examples of PDGFR kinase inhibitors that can be used according to the present invention include Imatinib (GLEEVEC®; Novartis); SU-12248 (sunitib malate, SUTENT®; Pfizer); Dasatinib (SPRYCEL®; BMS; also known as BMS-354825); Sorafenib (NEXAVAR®; Bayer; also known as Bay-43-9006); AG-13736 (Axitinib; Pfizer); RPR127963 (Sanofi-Aventis); CP-868596 (Pfizer/OSI Pharmaceuticals); MLN-518 (tandutinib; Millennium Pharmaceuticals); AMG-706 (Motesanib; Amgen); ARAVA® (leflunomide; Sanofi-Aventis; also known as SU101), and OSI-930 (OSI Pharmaceuticals); Additional preferred examples of low molecular weight PDGFR kinase inhibitors that are also FGFR kinase inhibitors that can be used according to the present invention include XL-999 (Exelixis);

SU6668 (Pfizer); CHIR-258/TKI-258 (Chiron); RO4383596 (Hoffmann-La Roche) and BIBF-1120 (Boehringer Ingelheim).

Examples of FGFR kinase inhibitors that can be used according to the present invention include RO-4396686 (Hoffmann-La Roche); CHIR-258 (Chiron; also known as TKI-258); PD 173074 (Pfizer); PD 166866 (Pfizer); ENK-834 and ENK-835 (both Enkam Pharmaceuticals A/S); and SU5402 (Pfizer). Additional preferred examples of low molecular weight FGFR kinase inhibitors that are also PDGFR kinase inhibitors that can be used according to the present invention include XL-999 (Exelixis); SU6668 (Pfizer); CHIR-258/TKI-258 (Chiron); RO4383596 (Hoffmann-La Roche), and BIBF-1120 (Boehringer Ingelheim).

The present invention further provides the preceding methods for treating tumors or tumor metastases in a patient, comprising administering to the patient a therapeutically effective amount of an IGF-1R kinase inhibitor and in addition, simultaneously or sequentially, a COX II (cyclooxygenase II) inhibitor. Examples of useful COX-II inhibitors include alecoxib (e.g. CELEBREX™), valdecoxib, and rofecoxib.

The present invention further provides the preceding methods for treating tumors or tumor metastases in a patient, comprising administering to the patient a therapeutically effective amount of an IGF-1R kinase inhibitor and in addition, simultaneously or sequentially, treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the IGF-1R kinase inhibitor according to this invention is an antibody, it is also possible to label the antibody with such radioactive isotopes.

Radiation therapy is a standard treatment for controlling unrespectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides the preceding methods for treating tumors or tumor metastases in a patient, comprising administering to the patient a therapeutically effective amount of an IGF-1R kinase inhibitor and in addition, simultaneously or sequentially, treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

As used herein, the term "patient" preferably refers to a human in need of treatment with an IGF-1R kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an IGF-1R kinase inhibitor.

In a preferred embodiment, the patient is a human in need of treatment for cancer, a precancerous condition or lesion, or other forms of abnormal cell growth. The cancer is preferably any cancer treatable, either partially or completely, by administration of an IGF-1R kinase inhibitor. The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

For purposes of the present invention, "co-administration of" and "co-administering" an IGF-1R kinase inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the IGF-1R kinase inhibitor, or in some combination thereof. Where the IGF-1R kinase inhibitor is administered to the patient at repeated intervals, e.g., during a standard course of treatment, the additional agent can be administered prior to, at the same time as, or subsequent to, each administration of the IGF-1R kinase inhibitor, or some combination thereof, or at different intervals in relation to the IGF-1R kinase inhibitor treatment, or in a single dose prior to, at any time during, or subsequent to the course of treatment with the IGF-1R kinase inhibitor.

The IGF-1R kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the IGF-1R kinase inhibitor can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of IGF-1R kinase inhibitor being used (for example, small molecule, antibody, RNAi, ribozyme or antisense construct), and the medical judgement of the prescribing physician as based, e.g., on the results of published clinical studies.

The amount of IGF-1R kinase inhibitor administered and the timing of IGF-1R kinase inhibitor administration will depend on the type (species, gender, age, weight, etc.) and condition of the patient being treated, the severity of the disease or condition being treated, and on the route of administration. For example, small molecule IGF-1R kinase inhibitors can be administered to a patient in doses ranging from 0.001 to 100 mg/kg of body weight per day or per week in single or divided doses, or by continuous infusion (see for example, International Patent Publication No. WO 01/34574). In particular, compounds such as Compound 66, or similar compounds, can be administered to a patient in doses ranging from 5-200 mg per day, or 100-1600 mg per week, in single or divided doses, or by continuous infusion. A preferred dose is 150 mg/day. Antibody-based IGF-1R kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The IGF-1R kinase inhibitors and other additional agents can be administered either separately or together by the same or different routes, and in a wide variety of different dosage forms. For example, the IGF-1R kinase inhibitor is preferably administered orally or parenterally. Where the IGF-1R kinase inhibitor is Compound 66, or a similar such compound, oral administration is preferable. Both the IGF-1R kinase inhibitor and other additional agents can be administered in single or multiple doses.

The IGF-1R kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The IGF-1R kinase inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous IGF-1R kinase inhibitors should be selected so as to avoid denaturation and/or degradation and loss of biological activity of the inhibitor.

Methods of preparing pharmaceutical compositions comprising an IGF-1R kinase inhibitor are known in the art, and are described, e.g. in International Patent Publication No. WO 01/34574. In view of the teaching of the present invention, methods of preparing pharmaceutical compositions comprising an IGF-1R kinase inhibitor will be apparent from the above-cited publications and from other known references, such as Remington's Pharmaceutical Sciences, Mack Publishing Company, Easton, Pa., $18^{th}$ edition (1990).

For oral administration of IGF-1R kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the IGF-1R kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous IGF-1R kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an IGF-1R kinase inhibitor in about 0.1% (w/v) to about 5% (w/v) concentration can be prepared.

For veterinary purposes, the active agents can be administered separately or together to animals using any of the forms and by any of the routes described above. In a preferred embodiment, the IGF-1R kinase inhibitor is administered in the form of a capsule, bolus, tablet, liquid drench, by injection or as an implant. As an alternative, the IGF-1R kinase inhibitor can be administered with the animal feedstuff, and for this purpose a concentrated feed additive or premix may be prepared for a normal animal feed. Such formulations are prepared in a conventional manner in accordance with standard veterinary practice.

As used herein, the term "IGF-1R kinase inhibitor" refers to any IGF-1R kinase inhibitor that is currently known in the art or that will be identified in the future, and includes any chemical entity that, upon administration to a patient, results in inhibition of a biological activity associated with activation of the IGF-1 receptor in the patient, including any of the downstream biological effects otherwise resulting from the binding to IGF-1R of its natural ligand. Such IGF-1R kinase inhibitors include any agent that can block IGF-1R activation or any of the downstream biological effects of IGF-1R activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF-1R polypeptides, or interaction of IGF-1R polypeptide with other proteins, or enhance ubiquitination and endocytotic degradation of IGF-1R. An IGF-1R kinase inhibitor can also act by reducing the amount of IGF-1 available to activate IGF-1R, by for example antagonizing the binding of IGF-1 to its receptor, by reducing the level of IGF-1, or by promoting the association of IGF-1 with proteins other than IGF-1R such as IGF binding proteins (e.g. IGFBP3). IGF-1R kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the IGF-1R kinase inhibitor is a small organic molecule or an antibody that binds specifically to the human IGF-1R.

IGF-1R kinase inhibitors include, for example imidazopyrazine IGF-1R kinase inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Additional examples of IGF-1R kinase inhibitors include those in International Patent Publication No. WO 05/037836, that describes imidazopyrazine IGF-1R kinase inhibitors, International Patent Publication Nos. WO 03/018021 and WO 03/018022, that describe pyrimidines for treating IGF-1R related disorders, International Patent Publication Nos. WO 02/102804 and WO 02/102805, that describe cyclolignans and cyclolignans as IGF-1R inhibitors, International Patent Publication No. WO 02/092599, that describes pyrrolopyrimidines for the treatment of a disease which responds to an inhibition of the IGF-1R tyrosine kinase, International Patent Publication No. WO 01/72751, that describes pyrrolopyrimidines as tyrosine kinase inhibitors, and in International Patent Publication No. WO 00/71129, that describes pyrrolotriazine inhibitors of kinases, and in International Patent Publication No. WO 97/28161, that describes pyrrolo[2,3-d]pyrimidines and their use as tyrosine kinase inhibitors, Parrizas, et al., which describes tyrphostins with in vitro and in vivo IGF-1R inhibitory activity (Endocrinology, 138: 1427-1433 (1997)), International Patent Publication No. WO 00/35455, that describes heteroaryl-aryl ureas as IGF-1R inhibitors, International Patent Publication No. WO 03/048133, that describes pyrimidine derivatives as modulators of IGF-1R, International Patent Publication No. WO 03/024967, WO 03/035614, WO 03/035615, WO 03/035616, and WO 03/035619, that describe chemical compounds with inhibitory effects towards kinase proteins, International Patent Publication No. WO 03/068265, that describes methods and compositions for treating hyperproliferative conditions, International Patent Publication No. WO 00/17203, that describes pyrrolopyrimidines as protein kinase inhibitors, Japanese Patent Publication No. JP 07/133,280, that describes a cephem compound, its production and antimicrobial composition, Albert, A. et al., *Journal of the Chemical Society*, 11: 1540-1547 (1970), which describes pteridine studies and pteridines unsubstituted in the 4-position, and A. Albert et al., *Chem. Biol. Pteridines Proc. Int. Symp., 4th*, 4: 1-5 (1969) which describes a synthesis of pteridines (unsubstituted in the 4-position) from pyrazines, via 3-4-dihydropteridines.

Additional IGF-1R kinase inhibitors useful in this invention include compounds represented by Formula (I) as described in US Published Patent Application US 2006/0235031 or published International patent application number WO 2005/097800 A1. OSI-906 represents an IGF-1R kinase inhibitor according to Formula (I), with the specific formula cis-3-[8-amino-1-(2-phenyl-quinolin-7-yl)-imidazo[1,5-a]pyrazin-3-yl]-1-methyl-cyclobutanol), and structure as follows:

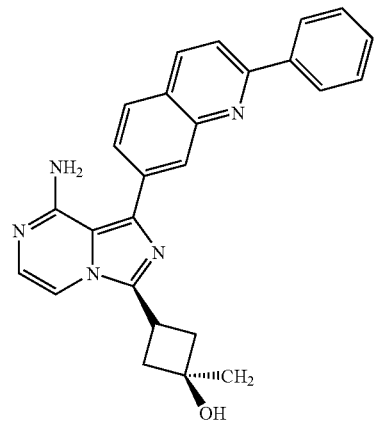

Additional, specific examples of IGF-1R kinase inhibitors that can be used according to the present invention include h7C10 (Centre de Recherche Pierre Fabre), an IGF-1 antagonist; EM-164 (ImmunoGen Inc.), an IGF-1R modulator; CP-751871 (Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g. NVP-AEW541, Garcia-Echeverria, C. et al. (2004) Cancer Cell 5:231-239; or NVP-ADW742, Mitsiades, C. S. et al. (2004) Cancer Cell 5:221-230); IGF-1R protein-tyrosine kinase inhibitors (Ontogen Corp); OSI-906 (OSI Pharmaceuticals); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and I-OMe-AG 538; BMS-536924, a small molecule inhibitor of IGF-1R; PNU-145156E (Pharmacia & Upjohn SpA), an IGF-1 antagonist; BMS 536924, a dual IGF-1R and IR kinase inhibitor (Bristol-Myers Squibb); AEW541 (Novartis); GSK621659A (Glaxo Smith-Kline); INSM-18 (Insmed); and XL-228 (Exelixis).

Antibody-based IGF-1R kinase inhibitors include any anti-IGF-1R antibody or antibody fragment that can partially or completely block IGF-1R activation by its natural ligand. Antibody-based IGF-1R kinase inhibitors also include any anti-IGF-1 antibody or antibody fragment that can partially or completely block IGF-1R activation. Non-limiting examples of antibody-based IGF-1R kinase inhibitors include those described in Larsson, O. et al (2005) Brit. J. Cancer 92:2097-2101 and Ibrahim, Y. H. and Yee, D. (2005) Clin. Cancer Res. 11:944s-950s, or being developed by Imclone (e.g. A12) or Schering-Plough Research Institute (e.g. 19D12; or as described in US Patent Application Publication Nos. US 2005/0136063 A1 and US 2004/0018191 A1). The IGF-1R kinase inhibitor can be a monoclonal antibody, or an antibody or antibody fragment having the binding specificity thereof.

Additional antibody-based IGF-1R kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against IGF-1R can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-IGF-1R single chain antibodies. Antibody-based IGF-1R kinase inhibitors useful in practicing the present invention also include anti-IGF-1R antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to IGF-1R.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-IGF-1R antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

IGF-1R kinase inhibitors for use in the present invention can alternatively be based on antisense oligonucleotide constructs. Anti-sense oligonucleotides, including anti-sense RNA molecules and anti-sense DNA molecules, would act to directly block the translation of IGF-1R mRNA by binding thereto and thus preventing protein translation or increasing mRNA degradation, thus decreasing the level of IGF-1R kinase protein, and thus activity, in a cell. For example, antisense oligonucleotides of at least about 15 bases and complementary to unique regions of the mRNA transcript sequence encoding IGF-1R can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as IGF-1R kinase inhibitors for use in the present invention. IGF-1R gene expression can be reduced by contacting the tumor, subject or cell with a small double stranded RNA (dsRNA), or a vector or construct causing the production of a small double stranded RNA, such that expression of IGF-1R is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as IGF-1R kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IGF-1R mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as IGF-1R kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

In the context of the methods of treatment of this invention, IGF-1R kinase inhibitors are used as a composition comprised of a pharmaceutically acceptable carrier and a non-toxic therapeutically effective amount of an IGF-1R kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an IGF-1R kinase inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the IGF-1R kinase inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an IGF-1R kinase inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An IGF-1R kinase inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise an IGF-1R kinase inhibitor compound in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical sue such as, for example, an aerosol, cream, ointment, lotion, dusting powder, or the like. Further, the compositions can be in a form suitable for use in transdermal devices. These formulations may be prepared, utilizing an IGF-1R kinase inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an IGF-1R kinase inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thomer. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Acedemic Press, Inc. (e.g. ISBN 0-12-213585-7)), or as described in the many university and commercial websites devoted to describing experimental methods in molecular biology.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experimental Details:

Introduction

Inhibitors of IGF-1 receptor function have shown clinical utility and the definition of key IGF-1 receptor signaling pathways which describe patient subsets most likely to benefit from therapy has become an important area of investigation. The ability of tumor cells to maintain growth and survival signals in the absence of adhesion to extracellular matrix or cell-cell contacts is important not only in the context of cell migration and metastasis but also in maintaining cell proliferation and survival in wound-like tumor environments where extracellular matrix is being remodeled and cell contact inhibition is diminished. Here we demonstrate that sensitivity of NSCLC and other tumor cells to IGF-1 receptor inhibition is conferred by an E-cadherin epithelial cell phenotype. Conversely insensitivity to IGF-1 receptor inhibition was mediated through an epithelial-mesenchymal transition (EMT) associated with the expression of vimentin and/or fibronectin. pERK, HER3 and pHER are also demonstrated to be biomarkers capable of predicting tumor cell sensitivity to IGF-1R kinase inhibitors.

Materials and Methods

Cell Culture and Preparation of Cell Extracts

The NSCLC lines with IGF-1R, H292, H358, H322, H441, A549, Calu6, H460, H1703 and SW1573 were cultured in the appropriate ATCC recommended supplemented media. Cell extracts were prepared by detergent lysis ((50 mM Tris-HCl, pH8, 150 mM NaCl, 1% NP-40, 0.5% NaDeoxycholate, 0.1% SDS) containing protease and phosphatase inhibitors. The soluble protein concentration was determined by micro-BSA assay (Pierce, Rockford Ill.).

The cell lines HCT-116, HT-29, GEO, Colo205, SW480, SW620, BxPC3, HPAC, CFPAC-1, MiaPaca-2, Panc1, A1165, MDA-MB-231, MDA-MB-435, DU4475, and MDA-MB-468 were routinely cultured in media as prescribed by the ATCC containing 10% FCS. With the exception of GEO tumor cells (obtained from Roswell Park Cancer Institute (RPCI)), and A1165 (obtained from FCRF (NCI-Frederick Cancer Research Facility)) all tumor cells were obtained from the ATCC.

Preparation of Cell Fractions

Membrane and cytosol fractions were prepared using ProteoExtract® reagent (EMD Biosciences, San Diego, Calif.; #444810). Afterwards, proteins were precipitated using trichloroacetic acid/deoxycholate coprecipitation where 2% deoxycholate was added to membrane or cytosol samples, incubated for 30 min on ice after which 100% TCA was added to samples in a 1:1 ratio (vol/vol). Samples were vortexed and incubated overnight (10° C.), centrifuged at 15,000×g for 10 minutes (4° C.), the precipitate washed with 5 ml cold acetone, vortexed, reprecipitated twice and air dried. Precipitated samples were resuspended in 8 M urea, reduced with 5 mM tributylphosphine (Sigma-Aldrich, St. Louis, Mo.; #T7567; 1 hour at RT), alkylated with iodoacetamide (15 mM for 1.5 hours at RT), diluted to 1M urea and subject to proteolysis with 20 ug trypsin (Sigma-Aldrich, St. Louis, Mo.; #T6567; 37° C., 18 hours). Peptides were acidified with trifluoroacetic acid (TFA) and desalted using C18 Sep-Pak Plus Cartridges (Waters Corporation, Milford, Mass.; #WAT020515). Protein concentration was determined using bicinchoninic acid (MicroBCA; Pierce, Rockford, Ill.;) was preformed and 200 ug of material was used for iTRAQ labeling for each cell line sample.

Cell surface capture was performed by crosslinking cell surface proteins to biotin, solubilization of the membrane lipids and recovery of the crosslinked proteins on streptavadin solid-phase resin. Captured proteins were released from the solid support by reduction of the thiol bond within the biotin linker. Samples were adjusted to 8 M urea, reduced with 5 mM tributylphosphine (Sigma-Aldrich, St. Louis, Mo.; #T7567; 1 hour at RT), alkylated with iodoacetamide (15 mM for 1.5 hours at RT), diluted to 1M urea and subject to proteolysis with 20 ug trypsin (Sigma-Aldrich, St. Louis, Mo.; #T6567; 37° C., 18 hours). Peptides were acidified with trifluoroacetic acid (TFA) and desalted using C18 Sep-Pak Plus Cartridges (Waters Corporation, Milford, Mass.; #WAT020515). Protein concentration was determined using bicinchoninic acid (MicroBCA; Pierce, Rockford, Ill.;) was preformed and 200 μg of material was used for iTRAQ labeling for each cell line sample.

Protein Identification and Quantitation by LC-MS/MS Peptide Sequencing

Anti-phosphotyrosine immunoaffinity resins were prepared by covalent coupling to a solid support by standard methods. Freshly prepared immunoaffinity resins were used for each biological experiment to maximize binding and reduce carryover. Briefly, anti-phosphotyrosine antibodies were crosslinked to solid-support and non-covalently bound IgG removed by low pH elution. Fresh affinity resins were prepared for each biological experiment to avoid cross-contamination. Proteins isolated by anti-phosphotyrosine affinity selection were measured by iTRAQ labeling of tryptic peptides as previously described (Ross et al, (2004) Mol Cell Proteomics 3(12) 1154-1169; Haley et al., 2004). Peptide masses and sequence information were determined by electrospray LC-MS/MS and database searching. Peptides with confidence levels of >=90% with scores of >=20 were considered, after which spectra were inspected manually. Peptide expression ratios were converted to $\log_2$ values and averaged to yield a single protein expression value for each time point (1, 4 and 24 hours) after erlotinib exposure (1 μM). Proteins were clustered by temporal $\log_2$ protein expression ratios using Euclidian hierarchical methods and self-organizing maps.

IGF-1R Inhibitor Compound Stock Solutions

IGF-1R inhibitor Compound 66 (i.e. 3-(3-Azetidin-1-ylmethyl-cyclobutyl)-1-(2-phenyl-quinolin-7-yl)-imidazo[1,5-a]pyrazin-8-ylamine; see structure below) stock concentration was 10 mM in 100% DMSO (dimethyl sulfoxide). Serial dilutions (1:3 or 1:4) were used to establish the 50% inhibitory dose of IGF-1R inhibitor. Before dosing, inhibitor was diluted in 100% DMSO, and then added to the cells at desired final concentrations in duplicates. The final DMSO concentration was between 0.3-0.5%. Compound 66 was synthesized by the methods described in published International patent application number WO 2005/097800 A1.

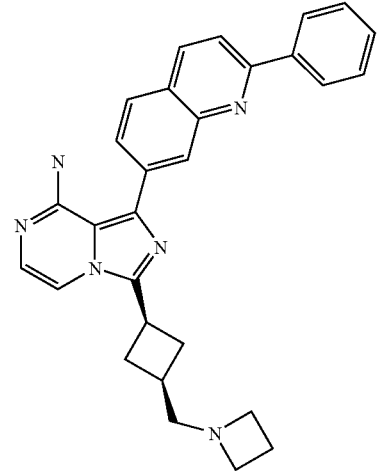

Compound 66

IGF-1R inhibitor Compound PQIP: Synthesis of PQIP: cis-3-[3-(4-Methyl-piperazin-1-yl)-cyclobutyl]1-(2-phenyl-quinolin-7-yl)-imidazo[1,5-a]pyrazin-8-ylamine (PQIP; see structure below), is a 1,3-disubstituted-8-amino-imidazopyrazine derivative synthesized by the methods described in patent application number WO 2005/097800 A1. Compound identity and purity (>99%) was verified by $^1$H and $^{13}$C nuclear magnetic resonance, mass spectrometry (MS), and high-performance liquid chromatography using Bruker Advance 400, WatersMicromass ZQ, and Waters LC Module I Plus instruments, respectively, as well as by elemental analysis. PQIP was dissolved in DMSO at 10 mmol/L for use in biochemical or cellular assays done in vitro. For in vivo studies, PQIP was dissolved in 25 mmol/L tartaric acid at an appropriate concentration to deliver the desired dose at 20 mL/kg by oral gavage.

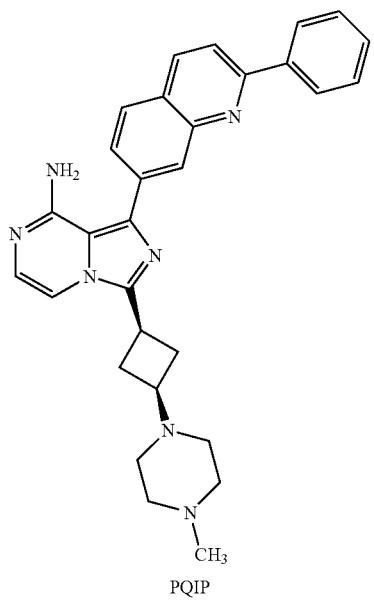

PQIP

Immunoblot and RNA Analysis of Cell Extracts

Protein immunodetection was performed by electrophoretic transfer of SDS-PAGE separated proteins to nitrocellulose, incubation with antibody and chemiluminescent second step detection (PicoWest; Pierce, Rockford, Ill.). The antibodies included: E-Cadherin (Santa Cruz Biotechnology, Santa Cruz, Calif.; sc21791), α-catenin (sc9988), β-catenin (sc7963), γ-catenin (sc8415) and Brk (sc 1188); Vimentin (BD Biosciences, San Jose, Calif.; BD550513) and Fibronectin (BD610077); GAPDH (AbCam, Cambridge, UK); Phospho-Akt (Cell Signaling (CS), Beverly, Mass. #9271), Akt (CS, #9272), Phospho-p44/42 Map kinase$^{T202/Y204}$ (Erk1/2; CS #9101), Phospho-Src family$^{Y416}$ (CS #2101), Phospho-STAT3$^{Y705}$ (CS, #9131) and Phospho-S6$^{S235/236}$ (CS, #2211); β-actin (Sigma, Saint Louis, Mo. #A5441). Antibodies further included: Phospho-Shc (Cell Signaling, #2434, Beverly, Mass.), Phospho-Paxillin (Cell Signaling, #2541), Phospho-Akt (Ser473 and Thr308) (Cell Signaling, #9271 and 9275), Phospho-HER2/ErbB2 (Cell Signaling, #2245), Phospho-Her3 (Tyr1289) (Cell Signaling #4791), Phospho-p44/42 Map kinase (Cell Signaling, #9101), Phospho-EGFR (Tyr845) (Cell Signaling, #2231), Phospho-EGFR (Tyr992) (Cell Signaling, #2235), Phospho-EGFR (Tyr1045) (Cell Signaling, #2237), EGFR (Cell Signaling, #2232), Phospho-p70 S6 kinase (Cell Signaling, #9205), Phospho-GSK-3alpha/beta (Cell Signaling, #9331), Phospho-EGFR (Tyr1068) (Cell Signaling, #2236), Phospho-Src family (Tyr416) (Cell Signaling #2101), phospho-SAPK/JNK (Thr183/Tyr185) (Cell Signaling #9251), phospho-STAT3 (Tyr705) (Cell Signaling #9131), ErbB2 (Cell Signaling #2242); ErbB4 (Cell Signaling 4795), PY20 (Exalpha Biologicals Inc.), Brk (Santa Cruz Biochemicals).

Cell extracts were prepared by detergent lysis (50 mM Tris-HCl, pH8.0, 150 mM NaCl, 1% NP-40, 0.5% NaDeoxycholate, 0.1% SDS, containing protease (P8340, Sigma, St. Louis, Mo.) and phosphatase (P5726, Sigma, St. Louis, Mo.) inhibitor cocktails. The soluble protein concentration was determined by micro-BSA assay (Pierce, Rockford Ill.).

For analysis of IGF-1R inhibitor (e.g. PQIP) effects on the phosphorylation of downstream signaling proteins, cell lines were grown to approximately 70% confluency, at which time compound was added at the indicated concentration, and cells were incubated at 37° C. for either two or 24 hours, as indicated. Where indicated, 40 ng/ml IGF ligands were added for 5 minutes. The media was removed, cells were washed 2× with PBS, and cells were lysed as previously described.

Snail, Sip1 and Zeb1 RNA transcript levels were determined by RT-PCR as follows: Taqman probe and primer sets for zeb1, snail, and Sip1 were obtained from Applied Biosystems (Foster City, Calif.). Quantitation of relative gene expression was conducted as described by the manufacturer using 30 ng of template. In order to determine relative expression across cell lines, amplification of the specific genes was normalized to amplification of the gene for GAPDH. Slug and Twist RNA transcript levels are similarly determined by RT-PCR.

In Vitro Pharmacology

For measuring cell viability, Cell-Titer Glo assay was used, which is available as a kit from Promega. The basis of the assay is a luminescent quantitation of ATP present in a cell culture plate well. In essence, the greater the number of viable cells in the well, the greater the level of ATP present. The assay utilizes a substrate that binds ATP to produce a luminescent signal, which can be read on a luminometer. Unless otherwise noted, the manufacturer's instructions were followed exactly. Briefly, on Day 1, cells were plated in 120 µl of 10% serum-containing growth media at a density of 4000 cells/well in a white polystyrene 96 well assay plate. On day 2, cells were treated with 15 µl of 10× concentration of the IGF-1R inhibitor (e.g. Compound 66, PQIP) or DMSO alone for a final well volume of 150 µl. After 72 h incubation with the inhibitor, the cells were assayed. Results were calculated as a fraction of the DMSO controlled cells.

Determination of CDH1 Promoter Methylation Status in Tumor Cells.

CDH1 promoter methylation status in tumor cells is determined by any of the methods known in the art (e.g. see Lombaerts, M. et al. (2006) British Journal of Cancer. 94:661-671; Yoshiura, K. et al. (1995) Proc. Natl. Acad. Sci. 92:7416-7419; Lind, G. E. et al. (2004) Molecular Cancer 3:28; Kumagai, T. et al. (2007) Int. J. Cancer. 121:656-665; Hennig, G. et al. (1996) J. Biol. Chem. 271(1):595-602; Marchevsky, A. M. et al. (2004). Journal of Molecular Diagnostics 6:28-36; Reinhold, W. C. et al. (2007). Mol. Cancer. Ther. 6:391-403; Hu, X-C. et al. (2002) Life Sciences 71:1397-1404; or Nakata, S. et al. (2006) Cancer 106(10): 2190-2199). Commercial kits are also available for determination of promoter methylation status in tumor cells (e.g. Promoter Methylation PCR kit, from Panomics, Redwood City, Calif.). CDH1 promoter methylation status can be determined by a methylation-specific PCR method. For example, typical steps would comprise digestion of genomic DNA with a restriction enzyme, incubation of the DNA fragments with a methylation binding protein (e.g. MeCP2) to form DNA/protein complexes, isolation of the complexes by affinity chromatography and elution of the DNA fragments, PCR amplification of the DNA fragments, and analysis of the PCR products by agarose gel electrophoresis. Alternatively, bisulfite modification of the genomic DNA prior to PCR can be used differentiate between methylated and unmethylated DNA (Herman, J. G. et al. (1996) Proc. Natl. Acad. Sci. 93:9821-9826).

In Vivo Pharmacology

Female CD-1 nu/nu mice (Charles River Laboratories) were implanted with harvested NSCLC tumor cells in a single subcutaneous site on the flank of the mice in the axillary region. Tumors were allowed to grow to 200±50 mm$^3$. Tumor volumes and body weights were determined twice weekly. The tumor volume was determined by measuring in two directions with vernier calipers and calculated using the formula: Tumor volume=(length×width$^2$)/2. Tumors from animals were harvested and snap frozen in liquid nitrogen.

Results

NSCLC Lines Containing wt IGF-1 Receptor Display a Range of Sensitivities to Compound 66

Analysis of Compound 66 sensitivity in a range of human NSCLC cell lines indicated a wide range of sensitivity. We have thus broadly classified these cell lines into those that are relatively insensitive (SW1573, and H460), those which show an intermediate sensitivity (A549) and those which are sensitive (H441, H358, and H292) to Compound 66-mediated growth inhibition. Thus, a range of sensitivities of the cells to Compound 66 was observed, ranging from the most sensitive (H358) through the least sensitive (SW1573).

Changes in Epithelial and Mesenchymal Cell Markers Correlate with Sensitivity of NSCLC Cell Lines to Compound 66

Figure 2:
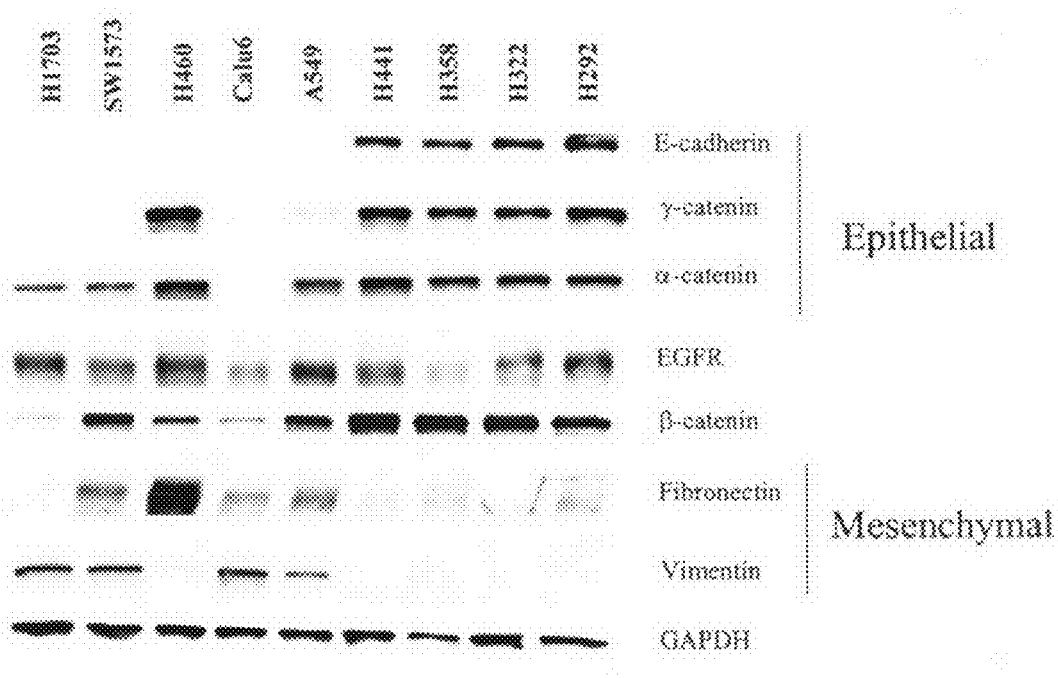
FIG. 2: NSCLC lines sensitive to IGF-1 receptor inhibition express elevated levels of E-cadherin, with trends observed for γ- and α-catenins. E-cadherin immunoblots were performed with two distinct antibodies with similar results (data not shown). NSCLC lines relatively insensitive to growth inhibition by Compound 66 expressed the mesenchymal proteins vimentin and/or fibronectin.

We observed a striking difference between the Compound 66 sensitive and relatively insensitive NSCLC lines in the abnormal expression vimentin and or fibronectin (FIG. 2). Typically vimentin and fibronectin expression are characteristic of mesenchymal cells and are only weakly or unexpressed in epithelial cell lineages. Vimentin expression was primarily found in SW1573, H1703 and Calu6, while fibronectin expression was observed in H460 cells. SW1573 cells were relatively insensitive to growth inhibition by Compound 66 in vitro, with less than 10% inhibition at 10 µM inhibitor. Little or no vimentin or fibronectin expression was found in the Compound 66 sensitive NSCLC lines H292, H441 and H358, or the intermediately sensitive line A549.

Based on the expression of mesenchymal proteins in NSCLC lines relatively insensitive to Compound 66, we analyzed protein extracts from the same panel of relatively insensitive and sensitive NSCLC cell lines for the presence or absence of markers characteristic of either epithelial or mesenchymal phenotypes (FIG. 2). Strikingly, E-cadherin was detected in the sensitive cell lines (H441, H358 and H292) but was absent in the relatively insensitive cell lines (SW1573 and H460). The intermediately sensitive cell line A549 showed low but detectable expression. A similar loss of γ-catenin was observed in cells relatively insensitive to Compound 66, with the exception of H460. Therefore, the relatively insensitive cell lines appear to have lost expression of epithelial cell marker proteins. Next we asked whether these cell lines expressed the mesenchymal markers fibronectin and/or vimentin. The relatively insensitive cell lines clearly expressed either one or both of fibronectin and vimentin (FIG. 2), whereas neither protein was detectable in cell lines sensitive to Compound 66. Interestingly the intermediately sensitive cell line A549 again showed low but detectable levels of both proteins. However, confocal microcopy experiments (results not shown) using immunostaining with antibodies specific for E-cadherin and vimentin indicated that the A549 cell culture used appears to be a mixed population of cells since no dual staining of cells was observed. This could also explain the somewhat variable results obtained with this cell line, and is consistent with its intermediate sensitivity to Compound 66.

Figure 3:
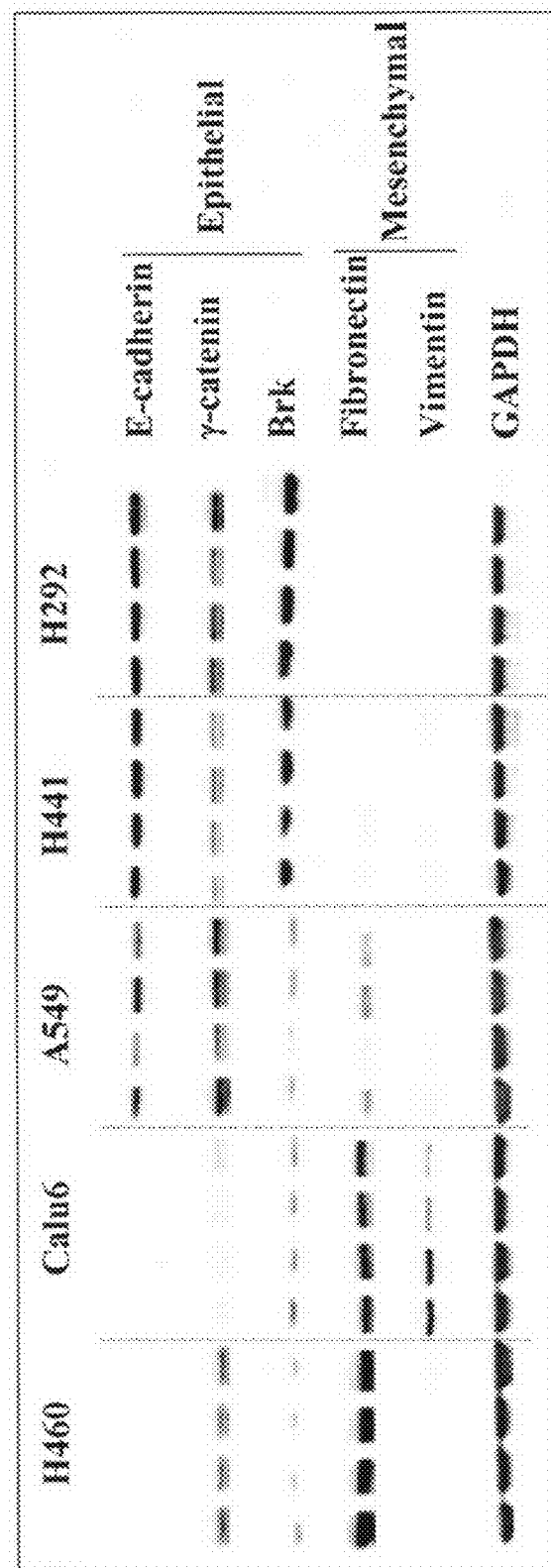
FIG. 3: NSCLC lines were grown as subcutaneous xenografts in SCID mice to a volume of ~500 mm³, excised and flash frozen in liquid nitrogen (4 animals per cell line). Tumor tissue was pulverized while frozen, subjected to detergent lysis and SDS-PAGE as described and immunoblots probed with antibodies to E-cadherin, γ-catenin, Brk, fibronectin, vimentin, and GAPDH. Consistent with in vitro results, E-cadherin expression was restricted to Compound 66 sensitive lines and fibronectin to relatively insensitive lines.
Figure 4:
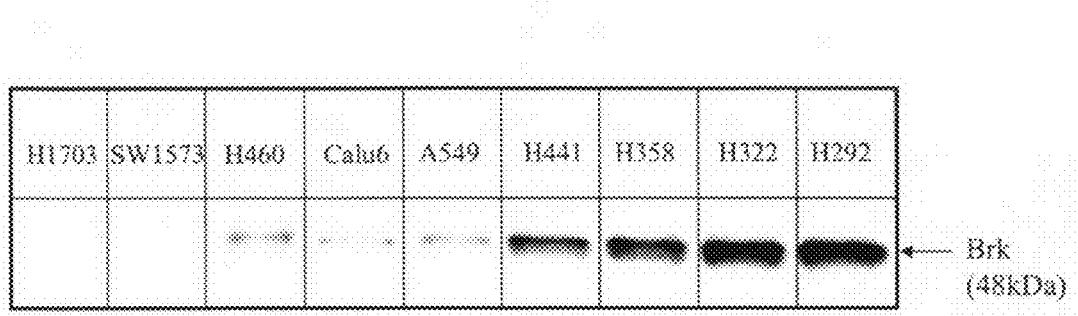
FIG. 4: Immunoblot showing higher Brk expression levels in NSCLC cell lines that are most sensitive to IGF-1R kinase inhibition.

Compound 66 Sensitivity Correlates with Maintenance of Epithelial Markers During Tumor Growth In Vivo We wished to examine whether the protein markers predictive of Compound 66 sensitivity identified in vitro were also observable in vivo. Protein extracts were prepared from 3 independent tumor xenografts grown from H460, Calu6, A549, H441 and H292 cells. Immunoblotting of extracts indicated that E-cadherin was not detectably expressed in the xenografts derived from the H460 cells that are relatively insensitive to Compound 66, was expressed at low levels in xenografts derived from the A549 cells of intermediate sensitivity and expressed at high levels in the H441 and H292 cell lines that are sensitive to Compound 66 (FIG. 3). A similar result was observed on analysis of γ-catenin levels. In contrast xenograft samples derived from H460 expressed fibronectin alone, a result consistent with that obtained from in vitro cell cultures (FIG. 2). H441 and H292 derived xenograft extracts showed little or no expression of either fibronectin or vimentin. These in vivo results further support the in vitro data and indicate that the presence of these protein markers is not an artifact of cell culture. Further, they support the hypothesis that Compound 66 sensitivity may be restricted to cells with an epithelial phenotype and that cells which have undergone EMT become less dependent upon IGF-1R signaling for cell proliferation and survival.

Expression of Brk in NSCLC Cell Lines that are Relatively Insensitive or Sensitive to IGF-1 Receptor Inhibition Interestingly there is a very good correlation between Brk levels and Compound 66 sensitivity in so far as high Brk expression equates to higher Compound 66 sensitivity and absence, or lower expression, of Brk tends to characterize insensitive lines.

Multiple Tumor Types Respond to IGF-1R Inhibition by PQIP

Figure 5:
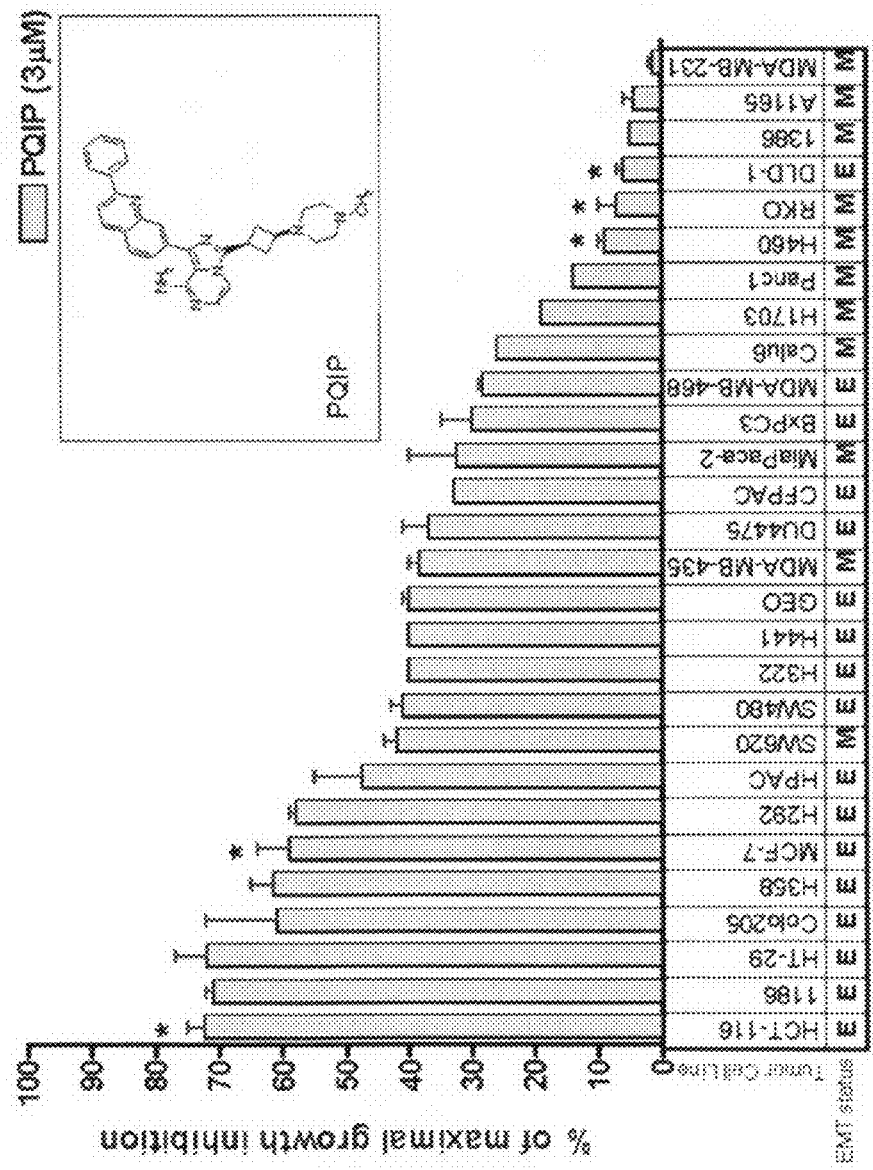
FIG. 5: The IGF-1R kinase inhibitor PQIP exhibits broad spectrum activity for inhibition of tumor cell growth. The effect of 3 μM PQIP on cell growth for a panel of 26 tumor cell lines is shown. The EMT status for the cell lines is indicated, and those tumor cell lines which harbor a known activating mutation in PI3K are marked by a *. EMT status is defined here according to the transcriptional activity of CDH1, the gene encoding E-Cadherin, indicated by either the methylation status of the CDH1 promoter or the presence of CDH1 gene transcriptional repressor proteins (e.g. Snail, Zeb1). Methylation or high levels of transcriptional repressors is associated with silencing of CDH1, and is thus an indicator of a mesenchymal cell. Cell growth was measured using Cell Titer Glo (Promega), and measurements were taken 72 hours after dosing. Data are expressed as % of maximal tumor growth inhibition and are representative of three or more independent experiments.

The sensitivity to growth inhibition by a selective low molecular weight inhibitor of the IGF-1R (PQIP; Mulvihill, M. J. et al. (2007) Bioorganic & Medicinal Chemistry Letters 17:1091-1097) was determined for a panel comprised of 28 tumor cell lines derived from colorectal (DLD-1, GEO, SW480, SW620, RKO, Colo205, HCT-116, and HT-29), breast (MCF-7, MDA-MB-468, DU4475, MDA-MB-231, and MDA-MB-435), pancreatic (BxPC3, HPAC, CFPAC, A1165, MiaPaca-2, and Panc1), NSCLC (NCI-H292, H358, Calu6, H322, NCI-H441, H1703, and NCI-H460), and head and neck tumors (1386 and 1186) (FIG. 5). Cells treated with 3 µM PQIP exhibited a range of sensitivities as shown by % maximal growth inhibition (2%-72%), and the median growth inhibition for the panel was 37%, denoted by the dashed red bar in FIG. 5. The effects of varying concentrations of PQIP on cell proliferation was determined for all cell lines (data not shown). This demonstrated that growth inhibition by PQIP is dose-dependent. Five tumor cell lines (HCT-116, MCF-7, DLD-1, NCI-H460, and RKO) included in this panel harbor known activating mutations in PI3K, indicated by a * in FIG. 5, suggesting that their proliferation and survival might be growth factor independent. However, although the growth for DLD-1, RKO, and NCI-H460 cells was inhibited by less than 20% by PQIP, HCT-116 and MCF-7 cells, which also harbor an activating mutation in PI3K, exhibited greater than 70% growth inhibition, indicating that mutations in PI3K are not uniformly predictive of insensitivity to IGF-1R antagonism. This result is consistent with our previous observations for sensitivity to EGFR inhibition, where the mutational status for PI3K also did not necessarily correlate with sensitivity.

It has been reported that epithelial tumor cells are more sensitive to EGFR inhibition than tumor cells that have undergone an EMT-like transition (Buck, E., et al. (2007) Mol Cancer Ther 6:532-541; Thomson et al. (2005) Cancer Res 65:9455-9462; Yauch, R. L., et al. (2005) Clin Cancer Res 11: 8686-8698). For this study (see FIG. 5), tumor cells were defined as epithelial (E) or mesenchymal (M) based upon based upon the transcriptional activity for E-cadherin gene (CDH1). Transcriptional repression of the E-cadherin gene has been previously defined as a hallmark for the EMT process (Thiery et al. (2003) Curr Opin Cell Biol 15:740-746). EMT is accompanied by a gain in the expression of a variety of transcription factors (e.g. Snail, Zeb1, Twist, Sip1, or Slug) that act to transcriptionally repress the CDH1 gene (De Craene, B. et al. (2005) Cancer Res. 65(14):6237-6244; Aigner, K. et al. (2007) Oncogene, advance online publication doi:10.1038/sj.onc.1210508, pages 1-10), and this is accompanied by promoter methylation. The CDH1 promoter methylation status for 19 of the 28 tumor cell lines within this panel (HCT-116, HT-29, Colo205, H358, MCF-7, SW620, SW480, H322, H441, MDA-MB-435, DU4475, MiaPaca-2, MDA-MB-486, H1703, Panc1, H460, RKO, DLD1, and MDA-MB-231) has been previously described (e.g. see Lombaerts, M. et al. (2006) British Journal of Cancer. 94:661-671; Yoshiura, K. et al. (1995) Proc. Natl. Acad. Sci. 92:7416-7419; Lind, G. E. et al. (2004) Molecular Cancer 3:28; Kumagai, T. et al. (2007) Int. J. Cancer. 121:656-665; Hennig, G. et al. (1996) J. Biol. Chem. 271(1):595-602; Marchevsky, A. M. et al. (2004). Journal of Molecular Diagnostics 6:28-36; Reinhold, W. C. et al. (2007). Mol. Cancer Ther. 6:391-403), and correlates with the expression of transcriptional repressors of E-cadherin including zeb1 and snail (Buck, E., et al. (2007) Mol Cancer Ther 6:532-541; Thomson et al. (2005) Cancer Res 65:9455-9462). For the other tumor cell lines within the panel, the promoter methylation status for CDH1 has not been described, however, tumor cell lines 1186, H292, HPAC, GEO, CFPAC, and BxPC3 have been previously reported to not express transcriptional repressors, whereas tumor cell lines Calu6, 1386, and A1165 have been reported to express transcriptional repressors (Buck, E., et al. (2007) Mol Cancer Ther 6:532-541; Thomson et al. (2005) Cancer Res 65:9455-9462). Although several tumor cell lines included in this panel are described to harbor mutations in the gene encoding E-cadherin (HCT-116, Colo205, and DU4475) (Buck, E., et al. (2007) Mol. Cancer Ther. 6:532-541) causing these cells to gain a mesenchymal-like morphology, E-cadherin in these cell lines is not transcriptionally repressed. Thus, EMT status, but not necessarily mesenchymal-like morphology, correlates with sensitivity to IGF-1R kinase inhibition such that epithelial tumor cells are substantially more sensitive than tumor cells that have undergone EMT. It should be noted however that the majority of tumor cells with mesenchymal-like morphology do appear to have undergone an EMT, and thus a morphometric analysis should be a useful predictor of sensitivity to IGF-1R kinase inhibition, although probably not the most preferred method. 70% of epithelial tumor cells achieved growth inhibition greater than the median growth inhibition (37%) of the panel, and inhibition above 50% was not observed with any mesenchymal tumor cell line in the panel. These data suggest that EMT biomarkers should be useful to identify patients most likely to respond to an IGF-1R kinase inhibitor. Biomarkers that can be used to differentiate epithelial from mesenchymal tumors include epithelial markers such as E-cadherin, as well as mesenchymal markers such as vimentin, Snail, Zeb1, Twist, Sip1, and Slug.

Additional Biomarkers Identified in NSCL Tumor Cells.

Reduced phospho-cytokeratins-7, -8 and -18 were observed in Calu6 (relative to the epithelial lines H292 and H358) and were completely absent in H11703, consistent with the mesenchymal-like phenotype of Calu6 and H1703. Similarly phosphocapture of α- and β-catenins was restricted to and δ-catenin markedly elevated in, the tumor cells with an epithelial state (H292 and H358). Phosphotyrosine capture of plakophilins-2, -3, 4, Desmoplakin-3 and Integrin-β4 were observed only NSCLC cells with an epithelial phenotype. Phospho E-cadherin was only observed in H292 with an epithelial phenotype. In summary proteins regulating cell adhesion were prominently expressed in tumor cells with an epithelial phenotype but were reduced or absent in tumor cells with a more mesenchymal-like phenotype. Differential expression and/or regulation of the p130CAS/paxillin containing cytoskeletal organizing complex or the heat shock protein complexes containing Hsp90, Hsp70, Hsp71, Hsp60, Hsp B1, Grp78 or Grp94 between epithelial and mesenchymal-like lines was not apparent. This is consistent with the observation that the vast majority of proteins were relatively unchanged in abundance between epithelial or mesenchymal phenotypes.

Altered Cell Survival Signaling Between Epithelial and Mesenchymal NSCLC Phenotypes The expression and/or regulation of multiple phosphoproteins were restricted to a particular cell type in a biologically interesting manner. For example the high phospho-PDGF receptor expression was only observed in H1703 cells, with lower abundance Fer and Fgr also observed. This was accompanied by elevated phosphocapture of SOS-1, SHP-2, Intersectin-2, tyrosine-protein kinase JAK1, GRB2-associated binding protein GAB1, Phospholipase C-γ1, PI3-kinase p110 subunits-α and -β, and PI3-kinase p85-α and -β subunits.

The hyaluronan motility receptor RHAMM was only detectable in the phosphotyrosine fraction of mesenchymal-like lines and may contribute to the increased migratory and invasive character associated with the mesenchymal phenotype. This may be particularly important since the mesenchymal NSCLC lines have reduced levels of Basigin (CD147).

In conclusion, the proteins and phosphoproteins listed above and in FIG. 7 provide additional biomarkers that can be used for assessing the EMT status and thus sensitivity to IGF-1R kinase inhibitors of tumor cells. Those protein biomarkers listed in a specific cellular compartment (i.e. cytosolic, membrane, or cell surface fractions), and perhaps also one or more phosphoprotein fractions, are proteins whose expression levels are altered as a result of EMT. Those proteins listed only in one or more phosphoprotein fractions have an altered phosphorylation level, but not protein expression level, in response to EMT. Thus, in the latter case the phospho-protein per se is the biomarker. Those tumor biomarkers listed in FIG. 7 as being decreased in mesenchymal-like cells are epithelial biomarkers, high expression levels of which correlate with high sensitivity to inhibition by IGF-1R kinase inhibitors. Those biomarkers listed in FIG. 7 as being increased in mesenchymal-like cells are mesenchymal biomarkers, high expression levels of which correlate with low sensitivity to inhibition by IGF-1R kinase inhibitors. Consequently, for the biomarkers listed in FIG. 7 a high ratio of epithelial to mesenchymal biomarker expression levels correlates with high sensitivity to inhibition by IGF-1R kinase inhibitors.

The biomarkers listed in FIG. 7 as of "mixed abundance in mesenchymal-like cells" are those for which an alteration in expression level of the protein and an altered phosphorylation state of the protein are predictive of different outcomes. For example, the protein "p185-Ron" is a mesenchymal marker that is increased in expression after EMT, and for which high expression levels correlate with low sensitivity to inhibition by IGF-1R kinase inhibitors, whereas "phospho-p185-Ron" is an epithelial marker that is decreased after EMT (i.e. there is a decrease in the phosphorylation level of p185-Ron after EMT), and for which high phosphorylation levels correlate with high sensitivity to inhibition by IGF-1R kinase inhibitors.

The biomarkers listed in FIG. 7 as being increased or decreased in the mesenchymal cell lines H1703 or Calu6 are biomarkers that appear to be altered in a cell-specific manner, unlike the other biomarkers listed above them in FIG. 7, which appear to be similarly altered in all tumor cells examined. Thus, the mesenchymal cell lines H1703 or Calu6 are probably each representative of a subset of tumor cell types in which these cell-specific biomarkers are altered in EMT and thus predictive of sensitivity to inhibition by IGF-1R kinase inhibitors in these tumor types.

The Biomarker pErk is Predictive of Insensitivity to the IGF-1R Kinase Inhibitor PQIP in NSCLC, Pancreatic, Colorectal, Breast and Ovarian Tumor Cells.

Figure 6:
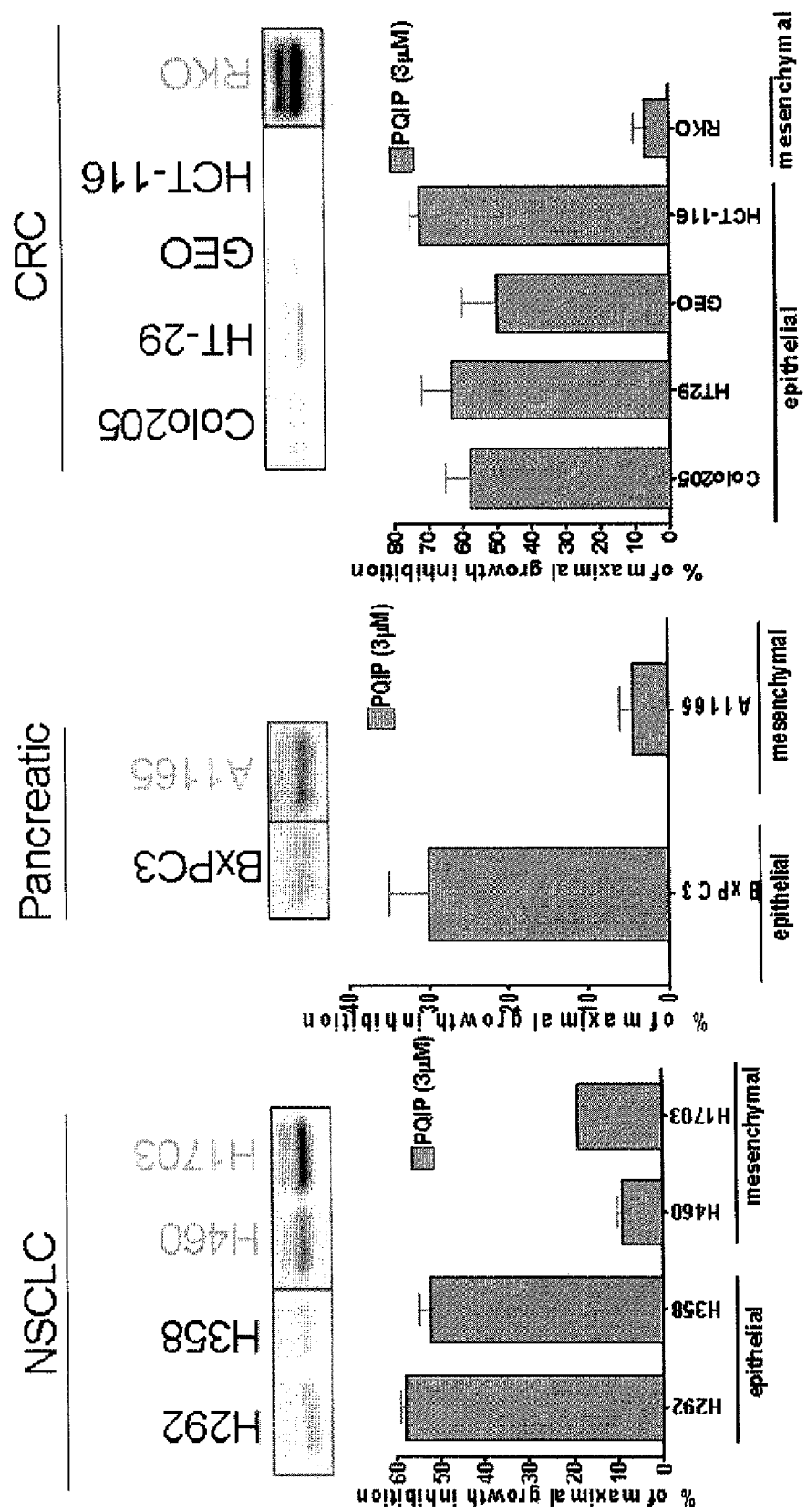
FIG. 6: pErk is predictive of insensitivity to the IGF-1R kinase inhibitor PQIP in NSCLC, pancreatic, and colorectal tumor cells. Shown is a western blot for pErk1/2, where pErk signal is captured using an antibody toward pT202/pY204 of Erk. Also shown is the maximal growth inhibition achieved by 3 μM PQIP. The shading of the cell line name is indicative of the EMT status of the CDH1 gene in that cell type, as defined above for FIG. 5, with dark text indicating an epithelial tumor cell and light text indicating a mesenchymal-like tumor cell.

For human NSCLC, pancreatic, and colorectal tumor cells (FIG. 6), it was found that the phosphorylation level of Erk correlated with both a decrease in sensitivity to the IGF-1R kinase inhibitor PQIP, and the transition of tumor cells to the mesenchymal state. Similar results were obtained for ovarian tumor cells (data not shown). Thus pErk is a biomarker that can effectively predict decreased sensitivity of tumor cells to IGF-1R kinase inhibitors, and should thus serve as a diagnostic to predict which patients are likely to benefit from IGF-1 receptor kinase inhibitor therapies, including anti-IGF-1 receptor antibody therapies.

Figure 8:
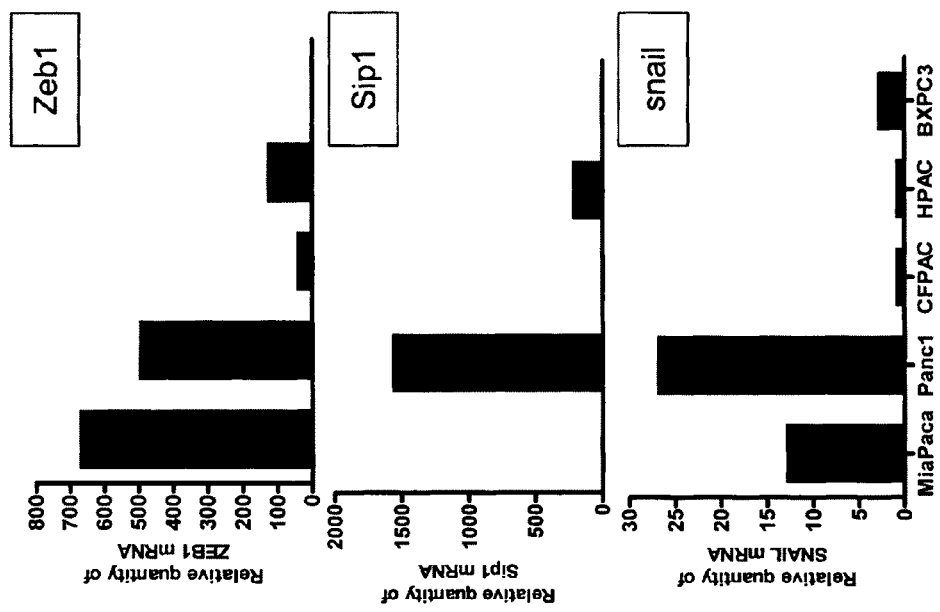
FIG. 8: E-cadherin gene repressor proteins are upregulated in mesenchymal tumor cells: Snail, Sip1 and Zeb1 RNA transcript levels were determined by RT-PCR in the mesenchymal pancreatic tumor cells Miapaca-2 and Panc1, and the epithelial pancreatic tumor cells CFPAC, HPAC and BXPC3.

The Mesenchymal Biomarkers Zeb1, Snail and Sip1 are Predictive of Insensitivity to the IGF-1R Kinase Inhibitor PQIP in NSCLC, Pancreatic, Colorectal, and Breast Tumor Cells.

mRNA transcript levels for Zeb1, Snail and Sip1 were measured for a representative panel of human cell lines (NSCLC, pancreatic, colorectal, and breast tumor cells) sensitive or relatively resistant to growth inhibition by an IGF-1R kinase inhibitor. Those cell lines that expressed higher levels of Zeb1, Snail or Sip1 (e.g. MiaPaca-2, Panc1, RKO) were among those that were relatively insensitive to IGF-1R inhibition. Those tumor cell lines that expressed comparatively lower levels of Zeb1, or Snail (e.g. CFPAC, HPAC, BxPC3, DLD1, GEO, HT-29, and Colo205) were all relatively sensitive to IGF-1R inhibition. Representative data are shown in FIG. 8 for pancreatic tumor cells lines, where those that expressed comparatively lower levels of Zeb1, Sip1 or Snail (i.e. CFPAC, HPAC, BxPC3) were all relatively sensitive to IGF-1R kinase inhibition, whereas those that expressed high levels of any of Zeb1, Sip1 or Snail were relatively insensitive to IGF-1R kinase inhibition. Thus, high levels of the mesenchymal biomarkers Zeb1, Snail and Sip1 are predictive of insensitivity to the IGF-1R kinase inhibitor PQIP in NSCLC, pancreatic, colorectal, and breast tumor cells.

CDH1 Promoter Methylation is Predictive of Insensitivity to the IGF-1R Kinase Inhibitor PQIP Human Tumor Cells.

An alternative indicator of the EMT status of cells is the methylation status of the E-cadherin gene (CDH1) promoter, which is an indicator of transcriptional repression. The CDH1 promoter methylation status for 19 of the 28 tumor cell lines described in FIG. 5 has been previously determined (e.g. see Lombaerts, M. et al. (2006) British Journal of Cancer. 94:661-671; Yoshiura, K. et al. (1995) Proc. Natl. Acad. Sci. 92:7416-7419; Lind, G. E. et al. (2004) Molecular Cancer 3:28; Kumagai, T. et al. (2007) Int. J. Cancer. 121:656-665; Hennig, G. et al. (1996) J. Biol. Chem. 271(1):595-602; Marchevsky, A. M. et al. (2004). Journal of Molecular Diagnostics 6:28-36; Reinhold, W. C. et al. (2007). Mol. Cancer Ther. 6:391-403), and correlates with the expression of transcriptional repressors of E-cadherin, including zeb1 and snail (Buck, E., et al. (2007) Mol Cancer Ther 6:532-541; Thomson et al. (2005) Cancer Res 65:9455-9462). Of these tumor cells, SW620, MDA-MB-435, MiaPaca-2, H1703, Panc1, H460, RKO, and MDA-MB-231 were determined to have CHD1 promoter methylation, whereas for HCT-116, HT-29, Colo205, H358, MCF-7, SW480, H322, H441, DU4475, MDA-MB-486, and DLD1, no CHD1 promoter methylation was detected (i.e. the promoter methylation level was low or zero). Comparison of this data with the sensitivity to IGF1R kinase inhibitors of these tumor cells (see FIG. 5) demonstrates that the degree of sensitivity of tumor cells to IGF1R kinase inhibitors correlates with the methylation status of the CDH1 gene, with tumor cells where no or low CDH1 promoter methylation is observed demonstrating significantly greater sensitivity to IGF1R kinase inhibitors. Thus, CDH1 promoter methylation is an effective biomarker that is predictive of insensitivity to the IGF-1R kinase inhibitors in tumor cells.

The Biomarker HER3 or pHER3 is Predictive of Sensitivity to the IGF-1R kinase inhibitor PQIP in Tumor Cells.

For a panel of 28 human tumor cells (FIG. 9; derived from colorectal (DLD-1, GEO, SW480, SW620, RKO, Colo205, HCT-116, and HT-29), breast (MCF-7, MDA-MB-468, DU4475, MDA-MB-231, and MDA-MB-435), pancreatic (BxPC3, HPAC, CFPAC, A1165, MiaPaca-2, and Panc1), NSCLC (NCI-H292, H358, Calu6, H322, NCI-H441, H1703, and NCI-H460), and head and neck tumors (1386 and 1186)), it was found that the expression of HER3 correlated with a higher sensitivity to inhibition by the IGF-1R kinase inhibitor PQIP. Similar results were obtained by analyzing levels of pHER3 (by immunoblotting analysis using antibodies specific to the phosphorylation site Y1289) rather than the expression of HER3 protein, for a subset of cell lines that were examined by this method (data not shown). Thus HER3 and pHER3 are biomarkers that can effectively predict high sensitivity of tumor cells to IGF-1R kinase inhibitors, and should thus serve as diagnostics to predict which patients are most likely to benefit from IGF-1 receptor kinase inhibitor therapies, including anti-IGF-1 receptor antibody therapies.

CONCLUSION

The loss of E-cadherin expression and the acquisition of a more mesenchymal phenotype has been shown to correlate with poor prognosis in multiple epithelial-derived solid tumors. The loss of E-cadherin and to a lesser extent γ-catenin and Brk correlated with cellular insensitivity to IGF-1 receptor kinase inhibition. Conversely the cellular acquisition of mesenchymal markers, vimentin, fibronectin or fibrillin correlates with a loss of sensitivity to IGF-1 receptor kinase inhibitors. We clearly show that a partial or complete epithelial to mesenchymal transition negatively impacts cellular responses to IGF-1 receptor kinase inhibitors and serves as a diagnostic for patients most likely to benefit from IGF-1 receptor kinase inhibitor therapies, including anti-IGF-1 receptor antibody therapies. Biomarkers associated with E-cadherin gene transcription repression, such as methylation of the E-cadherin gene promoter, or the presence of transcriptional repressor proteins (or mRNA transcripts) such as Snail, Zeb1, Twist, Sip1, or Slug, are effective predictors of insensitivity to IGF-1 receptor kinase inhibitors. Furthermore, the presence of the biomarker pErk appears to be a particularly effective diagnostic for identifying patients who might not benefit from IGF-1 receptor kinase inhibitor therapies, including anti-IGF-1 receptor antibody therapies. By contrast, the presence of the biomarker HER3 or pHER3 appears to be a particularly effective diagnostic for identifying patients who might benefit from IGF-1 receptor kinase inhibitor therapies, including anti-IGF-1 receptor antibody therapies.

ABBREVIATIONS

EGF, epidermal growth factor; EMT, epithelial to mesenchymal transition; NSCLC, non-small cell lung carcinoma; HNSCC, head and neck squamous cell carcinoma; CRC, colorectal cancer; MBC, metastatic breast cancer; EGFR, epidermal growth factor receptor; ErbB3, "v-erb-b2 erythroblastic leukemia viral oncogene homolog 3", also known as HER-3; pHER3, phosphorylated HER3; Erk kinase, Extracellular signal-regulated protein kinase, also known as mitogen-activated protein kinase; pErk, phosphorylated Erk; Brk, Breast tumor kinase (also known as protein tyrosine kinase 6 (PTK6)); LC, liquid chromatography; MS, mass spectrometry; IGF-1, insulin-like growth factor-1; IGF-1R or IGFR, insulin-like growth factor-1 receptor; TGFα, transforming growth factor alpha; HB-EGF, heparin-binding epidermal growth factor; LPA, lysophosphatidic acid; TGFα, transforming growth factor alpha; $IC_{50}$, half maximal inhibitory concentration; RT, room temperature; pY, phosphotyrosine; pPROTEIN, phospho-PROTEIN, "PROTEIN" can be any protein that can be phosphorylated, e.g. EGFR, ERK, HER3, S6 etc; wt, wild-type; PI3K, phosphatidyl inositol-3 kinase; GAPDH, Glyceraldehyde 3-phosphate dehydrogenase.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of predicting the sensitivity of pancreatic tumor cell growth to inhibition by an IGF-1R kinase inhibitor, comprising:
    assessing the level of the mesenchymal biomarker SNAI1 expressed by a pancreatic tumor cell; and
    predicting the sensitivity of pancreatic tumor cell growth to inhibition by an IGF-1R kinase inhibitor, wherein, relative to the expression level of SNAI1 in non-tumor cells of the same tissue, high levels of SNAI1 expression by pancreatic tumor cells correlates with low sensitivity to inhibition by IGF-1R kinase inhibitors.

2. The method of claim 1, wherein the IGF-1R kinase inhibitor is cis-3-[8-amino-1-(2-phenyl-quinolin-7-yl)-imidazo [1,5-α]pyrazin-3-yl]-1-methyl-cyclobutanol (OSI-906).

* * * * *